(12) United States Patent
Lin et al.

(10) Patent No.: US 11,884,613 B2
(45) Date of Patent: Jan. 30, 2024

(54) PROCESSES AND INTERMEDIATES FOR THE PREPARATION OF CARBAPROSTACYCLIN ANALOGUES

(71) Applicant: CHIROGATE INTERNATIONAL INC., Yangmei (TW)

(72) Inventors: Chun-Yu Lin, Yangmei (TW); Tzyh-Mann Wei, Yangmei (TW); Shih-Yi Wei, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 17/737,273

(22) Filed: May 5, 2022

(65) Prior Publication Data
US 2023/0357118 A1 Nov. 9, 2023

(51) Int. Cl.
C07C 59/62 (2006.01)
C07C 49/743 (2006.01)
C12P 7/38 (2006.01)
C07C 33/12 (2006.01)
C07D 307/42 (2006.01)
C12P 7/62 (2022.01)

(52) U.S. Cl.
CPC ............ *C07C 49/743* (2013.01); *C07C 33/12* (2013.01); *C07C 59/62* (2013.01); *C07D 307/42* (2013.01); *C12P 7/38* (2013.01); *C12P 7/62* (2013.01)

(58) Field of Classification Search
CPC .................................................. C07C 59/62
See application file for complete search history.

(56) References Cited

FOREIGN PATENT DOCUMENTS

EP 0 312 055 A2 4/1989
WO 2019/202345 A2 10/2019

OTHER PUBLICATIONS

Kramp, Guirdo, et al. "Fully Stereocontrolled Total Syntheses of the Prostacyclin Analogues 16S-Iloprost and 16S-3-Oxa-Iloprost by a Common Route, Using Alkenylcopper-Azoalkene Conjugate Addition, Asymmetric Olefination, and Allylic Alkylation." J. Am. Chem. Soc. (2005), vol. 127, pp. 17910-17920. (Year: 2005).*
Kazuhiko Takai, et al.: "Wittig-type Reactionof Dimetallated Carbodianion Species as Produced by Zinc Reduction of gem-Polyhalogen Compounds in the Presence of Lewis Acids": The Chemical Society of Japan: Bull. Chem. Soc. Jpn.: vol. 53, No. 6, pp. 1698-1702, 1980.
Sow-Mei L. Chen, et al.: "Prostaglandins and Congeners. 19. Vinylstannanes: Useful Organometallic Reagents for the Synthesis of Prostaglandins and Prostaglandin Intermediates": J. Org. Chem., vol. 43, No. 18, pp. 3450-3454, 1978.
Paul A. Aristoff: "Practical Synthesis of 6a-Carbaprostaglandin": J. Org. Chem. 1981, 46, pp. 1954-1957.
Paul A. Aristoff, et al.: "Synthesis of 9-Substituted Carbacyclin Analogues": J. Org. Chem. 1983, 48, pp. 5341-5348.
JACS_1973_95_6462.pdf.
Guido J. Kramp, et al.: "Fully Stereocontrolled Total Syntheses of the Prostacyclin Analogues 16S-Iloprost and 16S-3-Oxa-Iloprost by a Common Route, Using Alkenylcopper-Azoalkene Conjugate Addition, Asymmetric Olefination, and Allylic Alkylation": J. Am. Chem. Soc. 2005. 127, pp. 17910-17920.
Extended European Search Report for corresponding EP Patent Application No. 23165427.8 dated Aug. 21, 2023.

* cited by examiner

*Primary Examiner* — John S Kenyon
(74) *Attorney, Agent, or Firm* — Ladas & Parry LLP

(57) ABSTRACT

The invention relates to processes for preparing carbaprostacyclin analogues and intermediates prepared from the processes. The invention also relates to cyclopentenone intermediates in racemic or optically active form.

9 Claims, No Drawings

PROCESSES AND INTERMEDIATES FOR THE PREPARATION OF CARBAPROSTACYCLIN ANALOGUES

FIELD OF THE INVENTION

The present invention relates to novel processes and intermediates for the preparations of carbaprostacyclin analogues.

BACKGROUND OF THE INVENTION

Since the discovery of prostacyclins, a number of chemically and meta-bolically stable prostacyclin analogues have been developed as clinically effective antithrombotic agents. Among these, carbaprostacyclin analogues are some of the most attractive compounds. For example, Iloprost and 16S-Iloprost are effective for the treatment of pulmonary hypertension and vascular diseases.

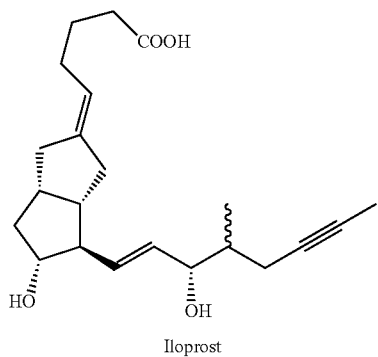

Iloprost

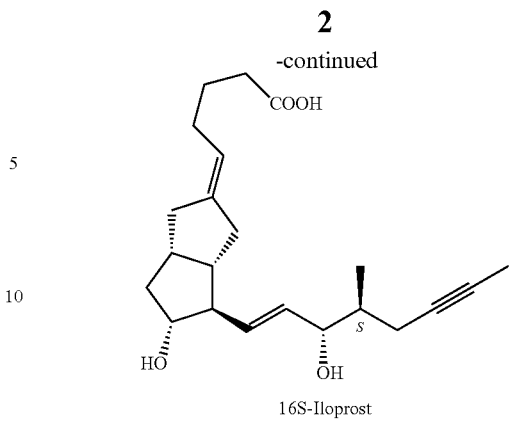

16S-Iloprost

Most current methods for mass production of carbaprostacyclin analogues in industry, such as that disclosed in *Journal of Organic Chemistry*, 1981, 46, 1954; *Journal of Organic Chemistry*, 1983, 48, 5341; and WO 2019/202345, as shown in Scheme 1, use expensive Prostaglandin intermediates, Corey Lactone, as the starting material, and use a four-step reaction to convert bicyclic Lactone A to bicyclic Ketone B,

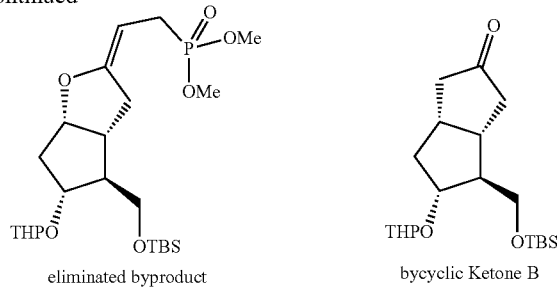

eliminated byproduct bycyclic Ketone B

However, almost none of the four steps can be regarded as an efficient reaction. For example, *Journal of Organic Chemistry*, 1981, 46, 1954 discloses that in the first alkylation reaction, about 20% starting material cannot be completely reacted; in the second oxidization reaction, up to 29% eliminated byproducts would be generated; and in the third intramolecular Homer Wadsworth Emmons (HWE) reaction, a large amount of intermolecular byproducts would be generated. Moreover, WO 2019/202345 discloses that the fourth hydrogenation step only has a yield of 23%. Therefore, the overall yield of the four-step reaction in the methods of JOC publica-tions or WO 2019/202345 is very low.

Moreover, the synthesis procedure from bicyclic Ketone B to carbaprostacyclin analogues, C5~C6 (E)-olefin, is established by Wittig reaction of bicyclic Ketone B as shown in Scheme 2. However, the Wittig reaction disclosed in *Journal of Organic Chemistry*, 1983, 48, 5341 has very poor selectivity and would generate about 35% Z-form byproduct (Z-isomer impurity). WO 2019/202345 uses the same Wittig reaction to establish the C5-C6 (E)-olefin, which also generates about 40% Z-form byproduct (Z-isomer impurity), and the generated Z-form byproduct is very difficult to be removed. WO 2019/202345 discloses that preparative HPLC may be used to reduce the amount of Z-form byproduct to less than 0.2 to 0.5%. Although WO 2019/202345 also discloses that the undesired Z-isomer can form a mixture of Z-isomer and E-isomer with a ratio of 1:1 by isomerization, still only a few amount of desired E-isomer can be recycled from such mixture via preparative HPLC. This method is time-consuming, expensive, and difficult for mass production, Scheme 2

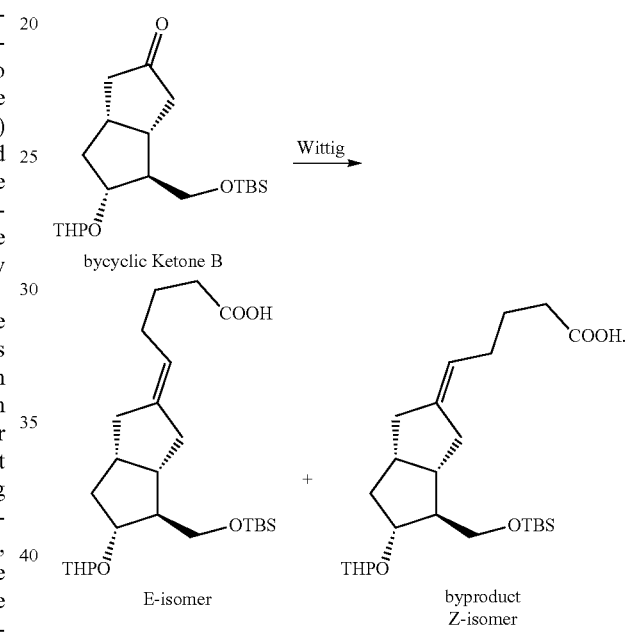

bycyclic Ketone B

E-isomer byproduct Z-isomer

In addition, as shown in Scheme 3, *Journal of the American Chemical Society*, 2005, 127, 17910-17920 uses a short-chain chiral phosphonate of Formula C to inhibit the generation of Z-form byproduct, but the chiral phosphonate of Formula C is expensive, and several additional required reactions significantly increase production costs, Scheme 3

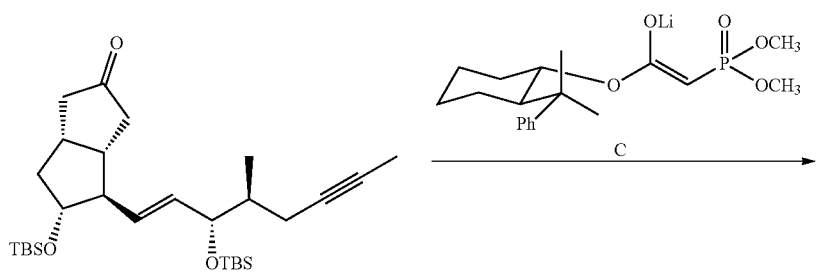

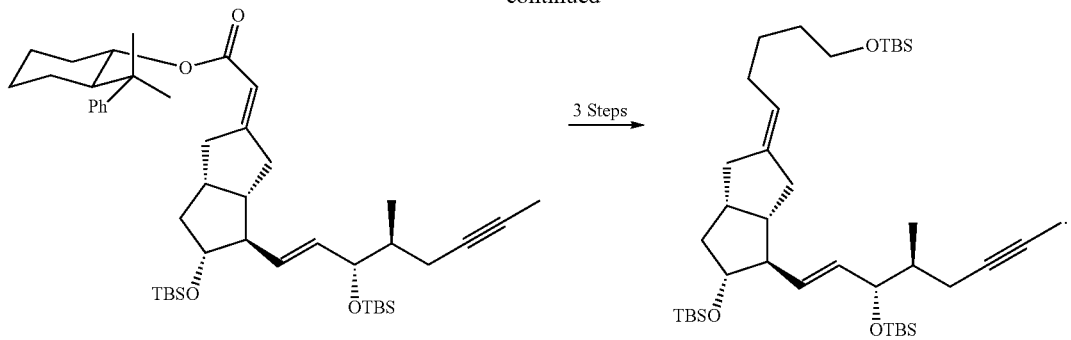

3 Steps →

SUMMARY OF THE INVENTION

Given the above, for reducing production costs, the present invention provides more efficient and selectivity approaches for producing carbacyclic prostacyclin such as Iloprost and 16(S)-Iloprost.

In one aspect, the present invention provides a racemic or optically active cyclopentenone of Formula 1:

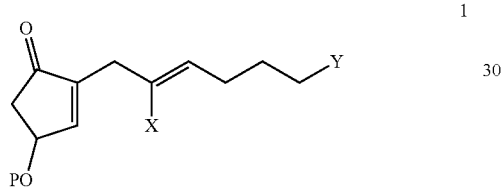

1 wherein Y is —CH$_2$OP or —COOR$_1$; X is F, Cl, Br, I, or —OTs; P is H or a hydroxyl protective group; and R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen, and alkoxy.

In one aspect, the present invention provides an optically active cyclopentenone of Formula (R)-1:

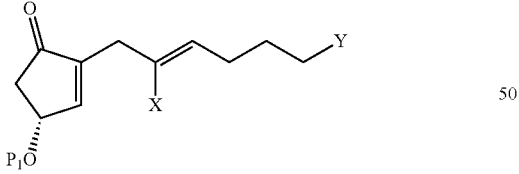

(R)-1 wherein Y is —CH$_2$OP or —COOR$_1$, X is F, Cl, Br, I, or —OTs; P is H or a hydroxyl protective group; and R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy, having an optical purity of at least 95% enantiomeric excess.

In one aspect, the present invention provides a novel process for the preparation of an optically active cyclopentenone of Formula (R)-1.

In one aspect, the present invention provides a novel process for the preparation of a compound of Formula (R)-1d:

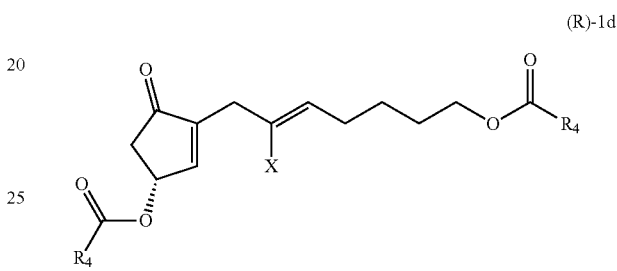

(R)-1d wherein X is F, Cl, Br, I, or —OTs; and R$_4$ is H or C$_{1-4}$ alkyl.

In one aspect, the present invention provides a process for the preparation of a compound of Formula 4:

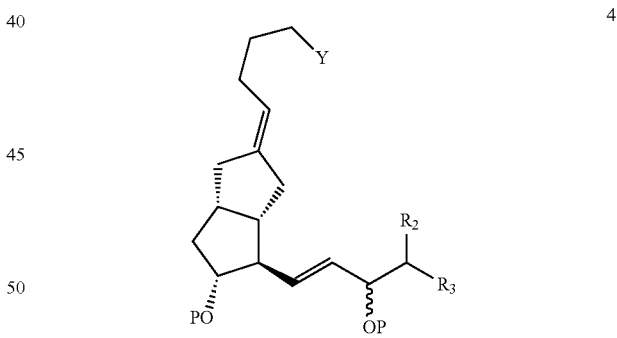

4 wherein Y is —CH$_2$OP or —COOR$_1$; P is H or a hydroxyl protective group; R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy; R$_2$ is H or C$_{1-4}$-alkyl; and R$_3$ is C$_{1-7}$-alkyl, C$_{2-7}$-alkynyl, aryl or aryloxy, each of which is unsubstituted or substituted by C$_{1-4}$-alkyl, halogen and trihalomethyl.

In one aspect, the present invention provides novel processes for the preparation of compound of Formula 4a:

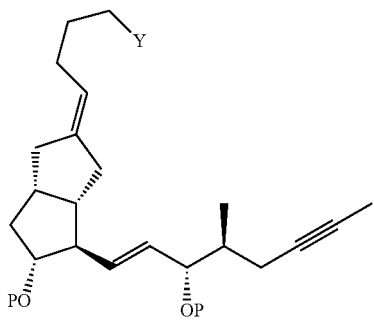

wherein Y is —CH$_2$OP or —COOR$_1$; P is H or a hydroxyl protective group; and R$_1$ is C$_{1-7}$-alkyl, aryl or aralkyl, each of which is unsubstituted or substituted by ClA-alkyl, C$_{2-7}$-alkenyl, C$_{2-7}$-alkynyl, nitro, halogen or alkoxy.

In one aspect, the present invention provides novel processes for the preparation of compound of Formula 4b:

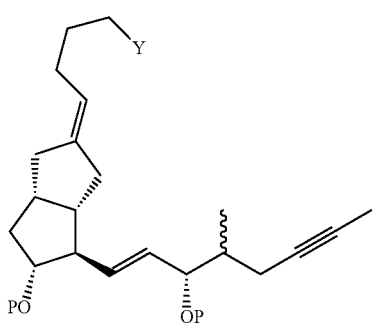

wherein Y is —CH$_2$OP or —COOR$_1$; P is H or a hydroxyl protective group; and R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy.

In one aspect, the present invention provides an intermediate of Formula 2,

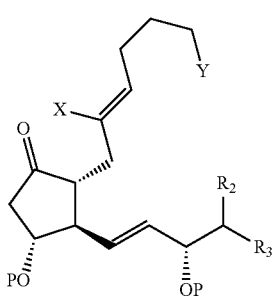

wherein Y is —CH$_2$OP or —COOR$_1$; X is F, Cl, Br, I, or —OTs; P is H or a hydroxyl protective group; R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy; R$_2$ is H or C$_{1-4}$-alkyl; and R$_3$ is C$_{1-7}$-alkyl, C$_{2-7}$-alkylnyl, aryl or aryloxy, each of which is unsubstituted or substituted by C$_{1-4}$-alkyl, halogen or trihalomethyl, for the preparation of carbaprostacyclin analogues.

In one aspect, the present invention provides an intermediate of Formula 2a:

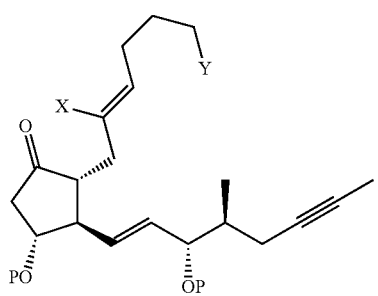

wherein Y is —CH$_2$OP or —COOR$_1$; X is F, Cl, Br, I, or —OTs; P is H or a hydroxyl protective group; and R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy, for the preparation of carbaprostacyclin analogues.

In one aspect, the present invention provides an intermediate of Formula 2b:

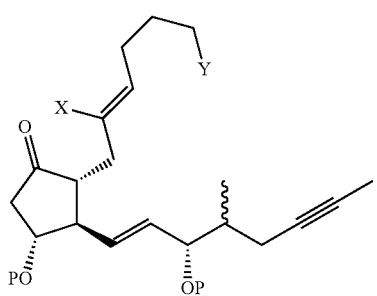

wherein Y is —CH$_2$OP or —COOR$_1$; X is F, Cl, Br, I, or —OTs; P is H or a hydroxyl protective group; and R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy, for the preparation of carbaprostacycin analogues.

In one aspect, the present invention provides an intermediate of Formula 3:

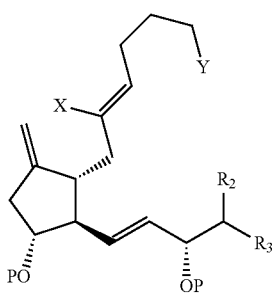

wherein Y is —CH$_2$OP or —COOR$_1$; X is F, Cl, Br, I, or —OTs; P is H or a hydroxyl protective group; R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy; $R_2$ is H or $C_{1-4}$-alkyl; and $R_3$ is $C_{1-7}$-alkyl, $C_{2-7}$-alkynyl, aryl or aryloxy, each of which is unsubstituted or substituted by $C_{1-4}$-alkyl, halogen or trihalomethyl, for the preparation of carbaprostacyclin analogues.

In one aspect, the present invention provides an intermediate of Formula 3a:

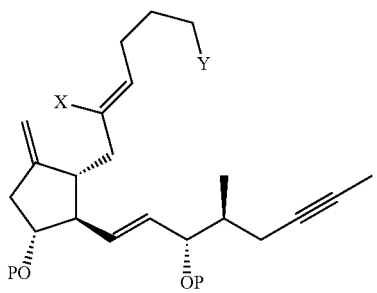

3a wherein Y is —CH$_2$OP or —COOR$_1$; X is F, Cl, Br, I, or —OTs; P is H or a hydroxyl protective group; and R$_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy, for the preparation of carbaprostacyclin analogues.

In one aspect, the present invention provides an intermediate of Formula 3b:

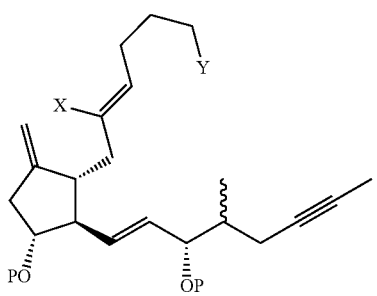

3b wherein Y is —CH$_2$OP or —COOR$_1$; X is F, Cl, Br, I, or —OTs; P is H or a hydroxyl protective group; and R$_1$ is $C_{1-7}$-alkyl, aryl or aralkyl, each of which is unsubstituted or substituted by CIA-alkyl, $C_{2-7}$-alkenyl, $C_{2-7}$-alkynyl, nitro, halogen or alkoxy, for the preparation of carbaprostacyclin analogues.

In one aspect, the present invention provides an intermediate of Formula 3':

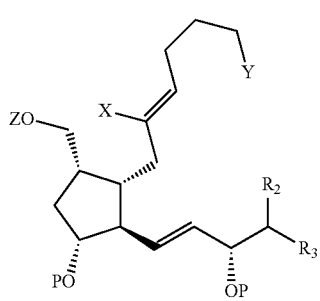

3' wherein Y is —CH$_2$OP or —COOR$_1$; X is F, Cl, Br, I, or —OTs; Z is H or a sulfonyl group; P is H or a hydroxyl protective group; R$_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy; $R_2$ is H or $C_{1-4}$-alkyl; and $R_3$ is $C_{1-7}$-alkyl, $C_{2-7}$-alkynyl, aryl or aryloxy, each of which is unsubstituted or substituted by $C_{1-4}$-alkyl, halogen or trihalomethyl, for the preparation of carbaprostacyclin analogues.

In one aspect, the present invention provides an intermediate of Formula 3'a:

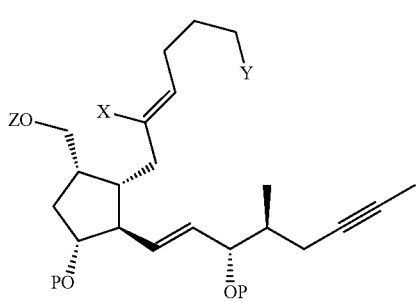

3'a wherein Y is —CH$_2$OP or —COOR$_1$; X is F, Cl, Br, I, or —OTs; Z is H or a sulfonyl group; P is H or a hydroxyl protective group; and R$_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy, for the preparation of carbaprostacyclin analogues.

In one aspect, the present invention provides an intermediate of Formula 3'b:

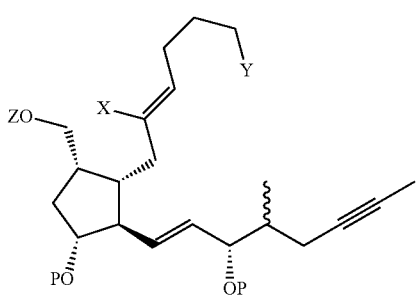

3'b wherein Y is —CH$_2$OP or —COOR$_1$; X is F, Cl, Br, I, or —OTs; Z is H or a sulfonyl group; P is H or a hydroxyl protective group; and R$_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy, for the preparation of carbaprostacyclin analogues.

In one aspect, the present invention provides an intermediate of Formula A2:

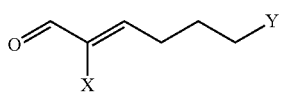

A2 wherein Y is —CH$_2$OP or —COOR$_1$; X is F, Cl, Br, I, or —OTs; P is H or a hydroxyl protective group; and R$_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy.

In one aspect, the present invention provides an intermediate of Formula A8:

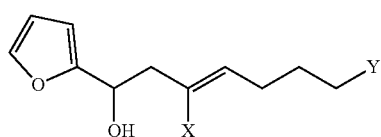

A8 wherein Y is —CH$_2$OP or —COOR$_1$; X is F, Cl, Br, I, or —OTs; P is H or a hydroxyl protective group; and R$_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy.

DETAILED DESCRIPTION OF THE INVENTION

Definition

The term "alkyl" used herein, unless otherwise indicated, refers to a straight or branched hydrocarbon group containing from 1 to 30 (e.g., from 1 to 10, 1 to 6, or 1 to 4) carbon atoms, such as methyl, ethyl, isopropyl, tert-butyl, and the like; or a cyclic saturated hydrocarbon group having from 3 to 10 (e.g., from 3 to 8) carbon atoms, such as cyclopropyl, cyclopentyl, cyclohexyl, methyl, and the like. The alkyl group may be unsubstituted or substituted.

The term "alkenyl" used herein, unless otherwise indicated, refers to a straight or branched hydrocarbon group containing from 2 to 20 (e.g., from 2 to 10) carbon atoms and one or more carbon-to-carbon double bonds, such as pentenyl, propenyl, and the like; or a cyclic unsaturated hydrocarbon group having from 5 to 20 carbon atoms and one or more carbon-to-carbon double bonds, such as cyclopentenyl, cyclohexenyl, and the like. The alkenyl group may be umsubstituted or substituted.

The term "alkynyl" used herein, unless otherwise indicated, refers to a straight or branched hydrocarbon group containing from 2 to 20 (e.g., from 2 to 10) carbon atoms and one or more carbon-to-carbon triple bonds such as pentynyl, propynyl, and the like; or a cyclic unsaturated hydrocarbon group having from 6 to 20 carbon atoms and one or more carbon-to-carbon triple bonds. The alkynyl group may be unsubstituted or substituted.

The term "aryl" used herein refers to a monocyclic or polycyclic aromatic hydrocarbon radical, such as phenyl, naphthyl, anthryl, phenanthryl and the like. The aryl group may be unsubstituted or substituted.

The term "aralkyl" used herein refers a straight or branched hydrocarbon containing from 1 to 20 (e.g., from 1 to 10 or 1 to 6) carbon atoms and one or more aryl group as described above, such as benzyl, benzhydryl, fluorenylmethyl, and the like. The term "aryloxy" may be phenoxy, tolyloxy, xylyloxy, and the like. The aralkyl or aryloxy group may be unsubstituted or substituted.

Each of the above mentioned alkyl, alkenyl, alkynyl, aryl, and aralkyl may optionally be substituted with one or more substituents selected from the group consisting of halogen, nitro, alkyl, alkenyl, alkynyl, aryl, alkoxy, aryloxy, thioalkoxy, thioaryloxy, alkylamino, arylamino, cyano, alkoxycarbonyl, arylcarbonyl, arylaminocarbonyl, alkylaminocarbonyl, and carbonyl or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl, pyrolidinonyl, or the like.

The term "hydroxyl protective group" has the meaning conventionally defined in organic synthetic chemistry, i.e., a group capable of protecting a functional group or moiety of a compound against the attacks of a chemical reaction. Examples of the protective group include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, acetyl, benzyl, substituted benzyl, acyl, substituted acyl, and SiR$_a$R$_b$R$_c$ wherein R$_a$, R$_b$ and R$_c$ are each independently $C_{1-4}$ alkyl, aryl, aralkyl, a substituted aryl, or a substituted benzyl. Each of the above mentioned aryl, benzyl and acyl may optionally be independently substituted with one or more substituents selected from the group consisting of halogen, alkyl, aryl, alkoxy, aryloxy, and the like.

In the depiction of the compounds given throughout this description, a thickened taper line (—◼) indicates a substituent which is in the beta-orientation (above the plane of the molecule or page), a broken flare line (⋯⦀) indicates a substituent which is in the alpha-orientation (below the plane of the molecule or page), and a wavy line (∿) indicates a substituent which is either in the alpha- or beta-orientation or in a combination of these orientations.

Synthetic Route of Racemic or Optically Active Cyclopentenone, Formula 1

The present invention provides a racemic or optically active cyclotentenone of Formula 1:

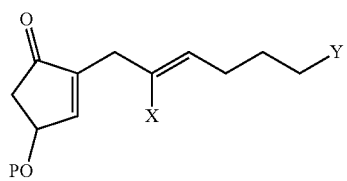

1 wherein Y is —CH$_2$OP or —COOR$_1$; X is F, Cl, Br, I, or —OTs; P is H or a hydroxyl protective group; and R$_1$ is $C_{1-7}$-alkyl, aryl or aralkyl, each of which is unsubstituted or substituted by $C_{1-4}$-alkyl, $C_{2-7}$-alkenyl. $C_{2-7}$-alkynyl, nitro, halogen or alkoxy.

The compound of Formula 1 is enriched in the (R)-enantiomer and has an optical purity of at least 95%, at least 99%, or at least 99.9% enantiomeric excess.

According to the present invention, the compound of Formula 1, such as the racemic cyclopentenones of Formulae (±)-1a and (±)-1b, may be prepared according to the reactions shown in Scheme A. As shown in Scheme A, the α-bromo-α,β-unsaturated aldehyde compound of Formula A2 is prepared by bromination (step 1) of the compound of Formula A1, and then the aldehyde compound of Formula A2 is subjected to a reduction reaction (step 2) and converted to the allyl alcohol compound of Formula A3. Further, a mesylation reaction (step 3) is subjected to convert the hydroxyl group in Formula A3 to a mesylate group for forming a compound of Formula A4. The compound of Formula A4 then reacts with the organolithium compound of Formula A4-1, which is prepared by reacting 2-(1,3-dithian- 2-yl) furan with n-butyllithium, via a substitution reaction (step 4) to form the compound of Formula A5. Following subjecting the compound of Formula A5 to undergo a desilyation reaction (step 5), a deprotection reaction (step 6) and a reduction reaction (step 7), the compound of Formula A8 is formed. The compound of Formula A8 then undergoes a Piancatelli rearrangement (step 8) and an isomerization reaction (step 9) to obtain the compound of Formula (±)-1a. The compound of Formula (±)-1a further undergoes a protection reaction (step 10) to generate the compound of Formula (±)-1b,

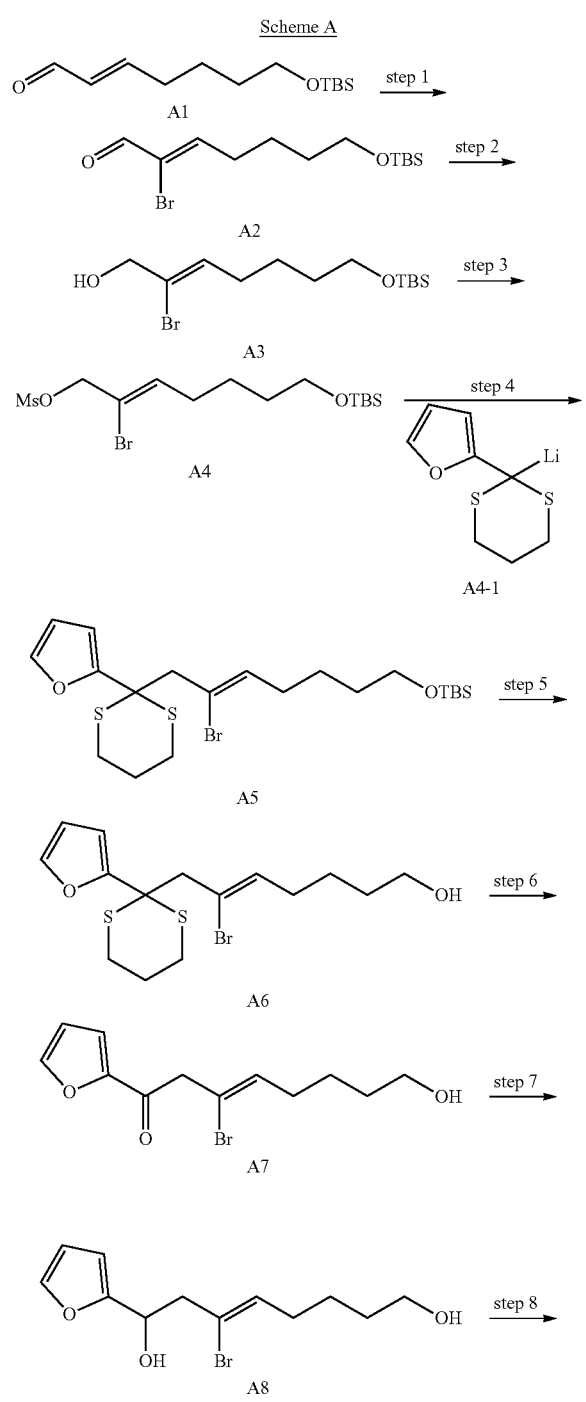

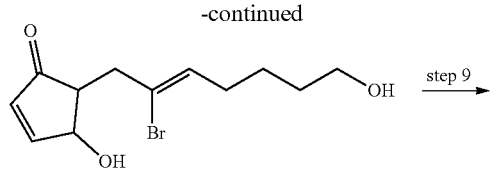

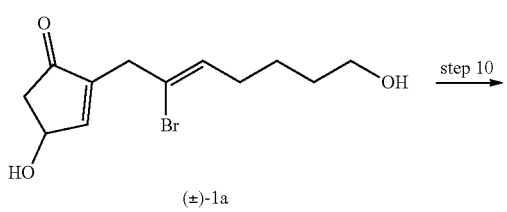

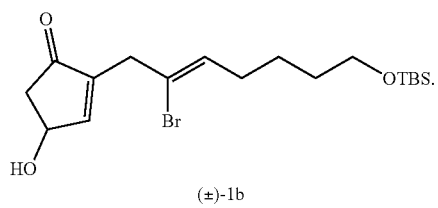

Step 1 of Scheme A pertains to a bromination reaction. In step 1, the α-bromo-α,β-unsaturated aldehyde compound of Formula A2 is generated from the α,β-unsaturated aldehyde compound of Formula A1 treated with a suitable reagent. The suitable reagent may include, but is not limited to, a mixture of N-bromosuccinimide (NBS) and pyridine N-oxide (PNO) in acetonitrile system; a mixture of OXONE® ($KHSO_5$-$0.5KHSO_4$-$0.5K_2SO_4$), hydrobromic acid (HBr) and triethylamine in dichloromethane system; a mixture of bromine and triethylamine in dichloromethane system; a mixture of bromine and pyridine in dichloromethane system; and triphenylphosphine hydrobromide in acetonitrile system; preferably a mixture of N-bromosuccinimide (NBS) and pyridine N-oxide (PNO) in acetonitrile system; and a mixture of OXONE® ($KHSO_5$-$0.5KHSO_4$-$0.5K_2SO_4$), hydrobromic acid (HBr) and triethylamine in dichloromethane system; and a mixture of N-bromosuccinimide (NBS) and pyridine N-oxide (PNO) in acetonitrile system is more preferable in this step. According to the invention, surprisingly, after analysis by HPLC, the novel bromination product of Formula A2 is produced with a Z-selectivity of at least about 95%, at least about 99%, preferably at least about 99.5%, and most preferably at least about 99.9%. The bromination product of Formula A2 is substantially free of E-isomer, or does not contain more than 1.0% of E-isomer, or does not contain more than 0.5% of E-isomer, or does not contain more than 0.1% of E-isomer.

As shown in Scheme B, the Z-isomer of the intermediate of Formula A2 generated in step 1 would form to the Z-isomer of the cyclopentenone of Formula 1. The Z-isomer of the cyclopentenone of Formula 1 would form to the E-isomer of the final carbaprostacyclin. That is to say, the ratio of the amount of Z/E-isomer of the intermediate of Formula A2 generated in step 1 completely corresponds to that of the final carbaprostacyclin.

Scheme B

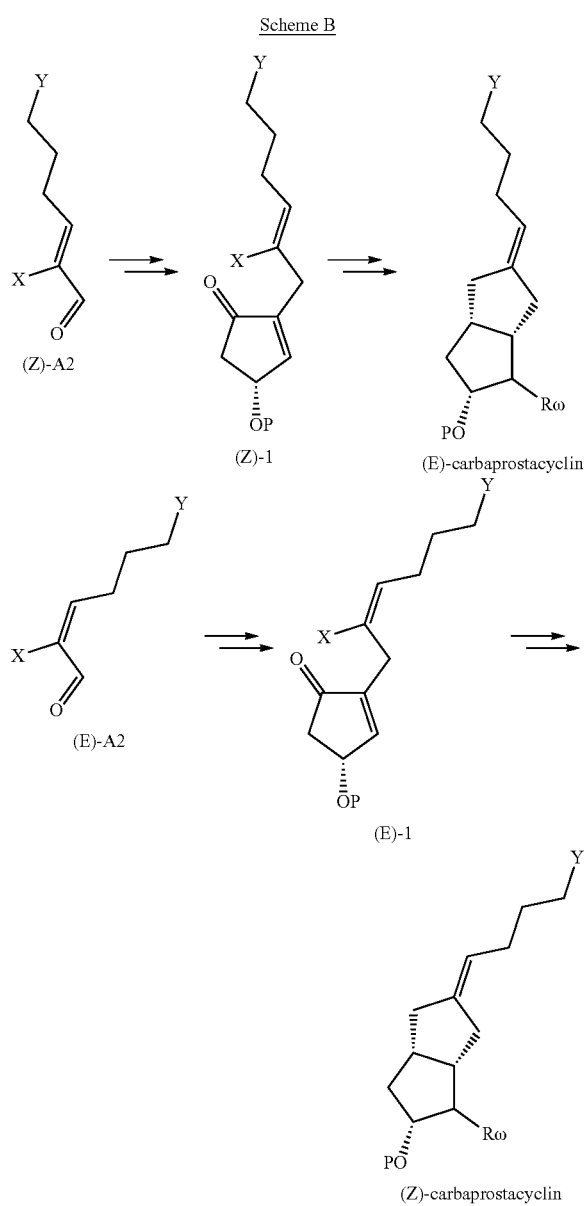

Therefore, the carbaprostacyclin synthesized from the Z-form compound of Formula A2 that is substantially free of E-isomer does not contain corresponding undesired Z-isomer. In contrast, conventional synthesized carbaprostacyclin would generate a large amount of undesired Z-isomers, which can only be removed by using expensive preparative HPLC and thus is not available for mass production. The synthesized (E)-carbaprostacyclin of the present invention almost does not contain any Z-isomers, so the costs to separate and remove undesired Z-isomers can be effectively reduced.

Step 2 of Scheme A involves a reduction reaction. In step 2, the carbonyl group of the compound of Formula A2 is reduced to a hydroxyl group with a reducing reagent. A suitable reducing reagent includes, but is not limited to, sodium borohydride, sodium bis(2-methoxyethoxy)aluminum hydride, diisobutylaluminum hydride, lithium tri-tert-butoxyaluminohydride, lithium tri-alkyl borohydride, potassium tri-alkyl borohydride, sodium tri-alkyl borohydride, and a mixture thereof; preferably lithium tri-sec-butylborohydride (L-selectride), sodium tri-sec-butylborohydride (N-selectride), potassium tri-sec-butylborohydride (K-selectride), lithium tri-amylborohydride, potassium tri-amylborohydride, and a mixture thereof; and sodium borohydride is more preferable in this step as a reducing reagent.

Step 3 of Scheme A pertains to a mesylation reaction. In step 3, the mesylate group, as a leaving group, of the compound of Formula A4 may be obtained from protection of the hydroxyl group of the compound of Formula A3 by using mesyl chloride and triethylamine in dichloromethane at 0° C.

Step 4 of Scheme A pertains to a substitution reaction. In step 4, the compound of Formula A5 may be generated by a substitution reaction, which is preferably performed at a temperature ranging from about −70° C. to about −50° C. with an organo-lithium compound of Formula A4-1, which is prepared from 2-(1,3-dithian-2-yl) furan and n-butyl-lithium.

Step 5 of Scheme A involves a desilylation reaction. In step 5, the desilylation reaction of the compound of Formula A5 to form the compound of Formula A6 is carried out by using a suitable reagent. The suitable reagent includes, but is not limited to, tetra-n-butylammonium fluoride (TBAF), hydrogen chloride, and a mixture thereof. The hydrogen chloride is more preferable in this step.

Step 6 of Scheme A pertains to a deprotection reaction. In step 6, the deprotection reaction of the compound of Formula A6 to form the compound of Formula A7 is carried out by using a suitable reagent. The suitable reagent includes, but is not limited to, bis(trifluoroacetoxy)iodobenzene (PIFA), iodine, mercury oxide (HgO), and a mixture thereof. The bis(trifluoroacetoxy)iodobenzene (PIFA) is more preferable in this step as a deprotection reagent.

Step 7 of Scheme A involves a reduction reaction. In step 7, the ketone group of the compound of Formula A7 is reduced to a hydroxyl group with a reducing reagent to form the compound of Formula A8. The suitable reducing reagent includes, but is not limited to, sodium borohydride, sodium bis(2-methoxyethoxy)aluminum hydride, diisobutylaluminum hydride, lithium tri-tert-butoxyaluminohydride, lithium tri-alkyl borohydride, potassium tri-alkyl borohydride, sodium tri-alkyl borohydride, and a mixture thereof; preferably lithium tri-sec-butylborohydride (L-selectride), sodium tri-sec-butylborohydride (N-selectride), potassium tri-sec-butylborohydride (K-selectride), lithium tri-amylborohydride, potassium tri-amylborohydride, and a mixture thereof; and sodium borohydride is more preferable in this step as a reducing reagent.

Step 8 of Scheme A pertains to a Piancatelli rearrangement. In step 8, the reaction may be carried out in a suitable phosphate buffer solution, and is then heated to reflux. A suitable phosphate buffer solution may be prepared with $K_2HPO_4$ and $H_3PO_4$ with a pH of about 2.0 to 4.5 in this step.

Step 9 of Scheme A pertains to an isomerization rearrangement. In step 9, the reaction may be carried out by using chloral hydride and triethyl amine in tetrahydrofunan.

Step 10 of Scheme A pertains to a silylation reaction. In step 10, the reaction may be carried out by using tert-butyldimethylsilyl chloride and imidazole in tetrahydrofuran at less than 20° C. The primary alcohol can be protected first to form the compound of Formula 1b.

Accordingly, the present invention also provides a novel compound of Formula A2:

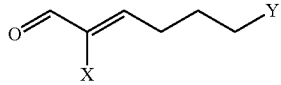

A2 wherein Y is —CH$_2$OP or —COOR$_1$; X is F, Cl, Br, I, or —OTs; P is H or a hydroxyl protective group; and R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy.

The present invention further provides a novel compound of Formula A8:

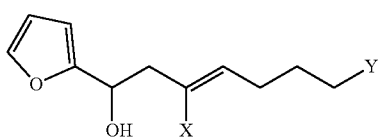

A8 wherein Y is —CH$_2$OP or —COOR$_1$; X is F, Cl, Br, I. or —OTs; P is H or a hydroxyl protective group; and R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy.

Chiral Resolution of Cyclopentenone, Formula (R)-1

A compound of Formula (R)-1 enriched in the (R)-enantiomer and having an optical purity of at least 95% enantiomeric excess, preferably at least about 99% enantiomeric excess, and most preferably at least about 99.9% enantiomeric excess, can be prepared from the starting compound of Formula 1, the compound of Formula (R)-1 having the following structure:

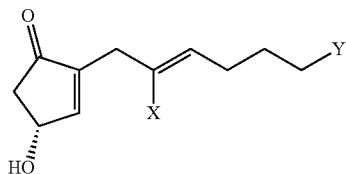

(R)-1 wherein Y is —CH$_2$OP or —COOR$_1$, X is F, Cl, Br, I, or —OTs; P$_1$ is H or a hydroxyl protective group; and R$_1$ is C$_{1-7}$-alkyl, aryl or aralkyl, each of which is unsubstituted or substituted by C$_{1-4}$-alkyl. C$_{2-7}$-alkenyl, C$_{2-7}$-alkynyl, nitro, halogen or alkoxy, the process comprising the steps of:

(1) enantioselectively (R)-esterifying a racemic compound of Formula 1:

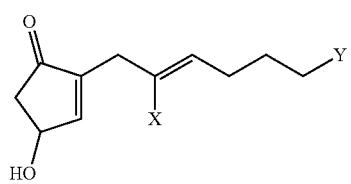

1 wherein Y and X are as defined above, with an acyl donor of Formula D:

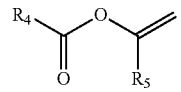

D wherein R$_4$ and R$_5$ are independently H or C$_{1-6}$ alkyl, and a first lipase, to form a (R)-ester of Formula (R)-1b' and an unreacted (S)-alcohol of Formula (S)-1:

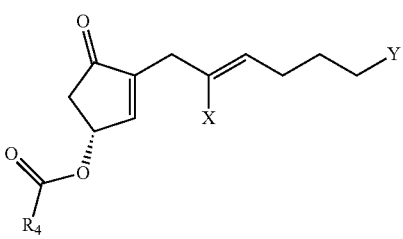

(R)-1b'

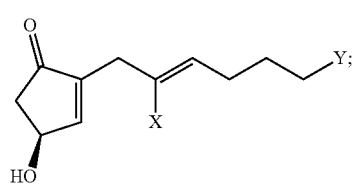

(S)-1

(2) removing the unreacted (S)-alcohol; and (3) deacylating the resultant (R)-ester.

In step 1, the acyl donor of Formula D may be vinyl acetate, isopropenyl acetate, vinyl valerate, isopropenyl valerate, vinyl butyrate, isopropenyl butyrate or a mixture thereof. The first lipase is commercially available and may be derived from *Burkholderia cepacia, Candida* antarcitica, Alcaligenese sp., *Pseudomonas* stutzri, *Pseudomonas cepacia* or a mixture thereof.

The removing step (2) comprises converting the unreacted (S)-alcohol into a corresponding (R)-ester by reacting the (S)-alcohol with an acyloxy donor of Formula R$_4$COOH, wherein R$_4$ is H or C$_{1-6}$ alkyl, in the presence of dialkylazodicarboxylate and trialkyl/triaryl phosphine. A suitable dialkylazodicarboxylate includes, but is not limited to, dimethyl azodicarboxylate (DMAD), diethyl azodicarboxylate (DEAD), diisopropyl azodicarboxylate (DIAD), di-tert-butyl azodicarboxylate (DTBAD), dibenzyl azodicarboxylate (DBAD), bis-trichloroethyl azodicarboxylate (BTCEAD), di-p-chlorobenzyl azodicarboxylate (DCAD), di-4-nitrobenzyl azodicarboxylate (DNAD), dicyclopentyl azodicarboxylate (DCpAD), and a mixture thereof; and preferably diethyl azodicarboxylate, diisopropyl azodicarboxylate, dibenzyl azodicarboxylate, and a mixture thereof. A suitable trialkyl/triaryl phosphine includes, but is not limited to, tri-n-butyl phosphine, triphenylphosphine, and a mixture thereof; and preferably triphenylphosphine.

The deacylation step (3) comprises an enzymatic cleavage reaction using a second lipase derived from *Candida cylindracea, Pseudomonas* stutzri, Alcaligenese sp., *Achromobacter* sp., *Burkholderia cepacia, Candida* antarcitica or a mixture thereof, preferably *Candida* antarcitica. In some embodiments, the deacylation step (3) is a chemical hydrolysis.

Synthetic Route of Optically Active Cyclopentenone, Formula (R)-1b

Scheme C depicts a process for preparing an optically active cyclopentenone of Formula (R)-1b. According to the reactions shown in Scheme C, the racemic cyclopentenone of Formula (±)-1b can be chirally resolved to form a cyclopentenone enriched in the (R)-enantiomer and having a high optical purity. As shown in Scheme C, the racemic compound of Formula (±)-1b is resolved via enantioselective esterification (step 1) by using a first lipase to form a mixture of unreacted alcohol of Formula (S)-1b and a compound of Formula (R)-1c. Then, the mixture can directly undergo a Mitsunobu reaction (step 2) to convert the alcohol of Formula (S)-1b into the compound of Formula (R)-1c. Finally, the compound of Formula (R)-1c is deacylated to form the compound of Formula (R)-1b having a high optical purity by using a chemical hydrolysis reaction or an enzymatic cleavage reaction (step 3),

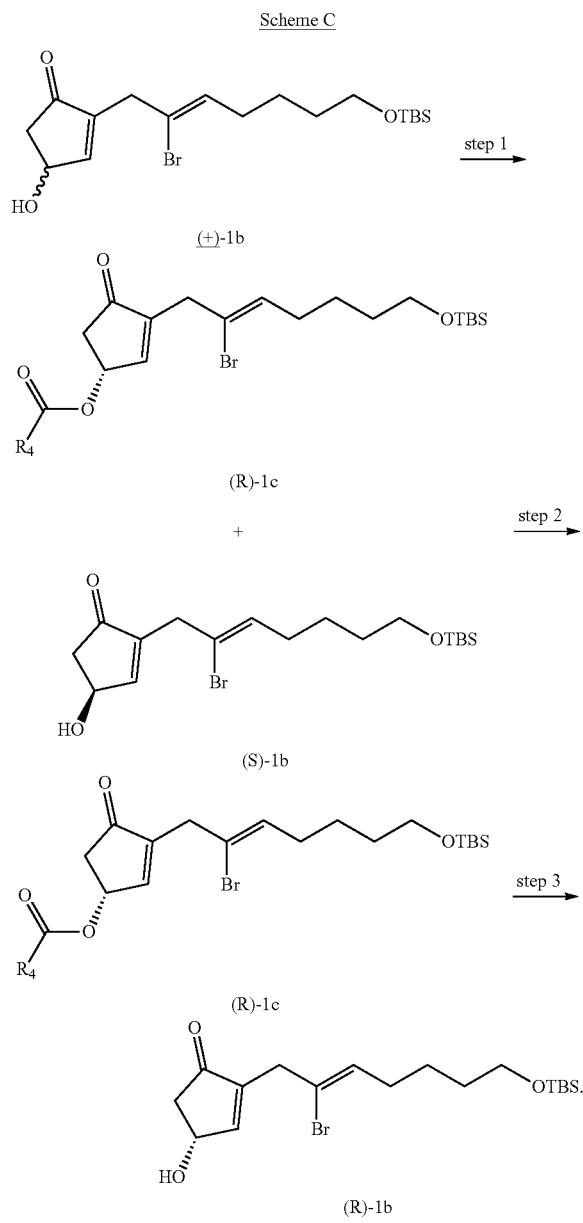

In step 1 of Scheme C, the enantioselective esterification of the cyclopentenone of Formula (±)-1b is performed with an acyl donor of Formula D, wherein $R_4$ and $R_5$ are independently H or $C_{1-6}$ alkyl, in the presence of a first lipase, wherein the acyl donor preferentially reacts with the cyclopentenone in (R)-form, thereby generating a mixture essentially consisting of an optically active ester of Formula (R)-1c and an unreacted alcohol of Formula (S)-1b,

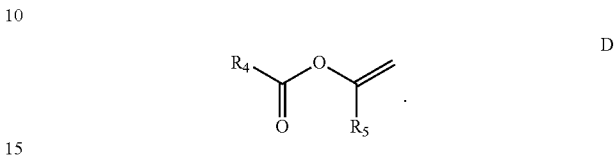

In some embodiments, a suitable first lipase is commercially available and may be derived from *Burkholderia cepacia, Candida* antarcitica, Alcaligenese sp., *Pseudomonas* stutzri, *Pseudomonas cepacia* or a mixture thereof, preferably Alcaligenese sp, or *Burkholderia cepacia*, and most preferably *Burkholderia cepacia*. A suitable acyl donor includes, but is not limited to, vinyl acetate, isopropenyl acetate, vinyl valerate, isopropenyl valerate, vinyl butyrate, isopropenyl butyrate, and a mixture thereof, and vinyl acetate is particularly preferable. Furthermore, the enantioselective esterification reaction may be performed in a single organic solvent or a mixture of organic solvents, such as hexane, cyclohexane, toluene, tetrahydrofuran, methyl ethyl ketone, methyl isobutyl ketone, ether, isopropyl ether, methyl isopropyl ether, tert-butyl methyl ether, and a mixture thereof. An appropriate reaction temperature ranges from about 5° C. to about 50° C., preferably at ambient temperature.

Step 2 of Scheme C pertains to a Mitsunobu reaction. In the Mitsunobu reaction, the unreacted alcohol of Formula (S)-1b can be treated with an acyloxy do-nor of Formula $R_4COOH$ (wherein $R_4$ is H or $C_{1-6}$ alkyl), to convert it into the compound of Formula (R)-1c, in the presence of dialkyl azodicarboxylate and trialkyl/triaryl phosphine in a suitable solvent. A suitable dialkyl azodicarboxylate includes, but is not limited to, dimethyl azodicarboxylate (DMAD), diethyl azodicarboxylate (DEAD), diisopropyl azodicarboxylate (DIAD), di-tert-butyl azodicarboxylate (DTBAD), dibenzyl azodicarboxylate (DBAD), bis-trichloroethyl azodicarboxylate (BTCEAD), di-p-chlorobenzyl azodicarboxylate (DCAD), di-4-nitrobenzyl azodicarboxylate (DNAD), dicyclopentyl azodicarboxylate (DCpAD), and a mixture thereof; and preferably diethyl azodicarboxylate, diisopropyl azodicarboxylate, dibenzyl azodicarboxylate, and a mixture thereof. A suitable trialkyl/triaryl phosphine includes, but is not limited to, tri-n-butyl phosphine, triphenylphosphine, and a mixture thereof; and preferably triphenylphosphine. A suitable solvent in the Mitsunobu reaction includes, but is not limited to, tetrahydrofuran, toluene, benzene, dimethyl-formamide, diethyl ether, acetonitrile, dichloromethane, and a mixture thereof. The Mitsunobu reaction is preferably carried out at an appropriate temperature ranging from about −30° C. to about 70° C., preferably at ambient temperature.

Step 3 of Scheme C pertains to a deacylation reaction. In one embodiment, the deacylation reaction in Step 3 of Scheme C is a chemical hydrolysis in the presence of an alcohol and a base such as lithium hydroxide, sodium hydroxide, or potassium hydroxide. In another embodiment, the deacylation reaction in step 3 of Scheme C is an enzymatic cleavage reaction. The enzymatic cleavage reaction can be per-formed in the presence of a second lipase in a suitable organic solvent or an aqueous system at an appropriate temperature to obtain the compound of Formula (R)-1b. A suitable second lipase is commercially available and can be derived from *Candida cylindracea*, *Pseudomonas* stutzri, *Alcaligenese* sp., *Achromobacter* sp., *Burkholderia cepacia*, *Candida antarcitica* or a mixture thereof; and preferably from *Alcaligenese* sp., *Burkholderia cepacia*, *Candida* antarctica, or a mixture thereof; and most preferably from *Burkholderia cepacia*. The suitable organic solvent and the appropriate temperature in this step are obvious in the art.

According to the invention, the deacetylation reaction is monitored for the purpose of an optical purity of the resultant compound of Formula (R)-1b. In some embodiments, the deacetylation reaction is monitored by HPLC using a chiral column and stopped by removing the second lipase, preferably when the optical purity of the resultant compound decreases to about 95% e.e., preferably about 99% e.e., and more preferably about 99.9% e.e. In some embodiments, the unreacted ester of Formula (R)-1c and it's enantiomer can be removed such as by column chromatography after the deacetylation reaction. According to the invention, the compound of Formula (R)-1b is produced with an optical activity of at least about 95% e.e., preferably at least about 99% e.e., and most preferably at least about 99.9% e.e.

Synthetic Route of Optically Active Cyclopentenone, Formula (R)-1d

Scheme D depicts a process for preparing a racemic cyclopentenone of Formula (R)-1d. According to the reactions shown in Scheme D, the racemic cyclopentenone of Formula (±)-1a can be chirally resolved easily to form a cyclopentenone enriched in the (R)-enantiomer and having a high optical purity according to the reactions. As shown in Scheme D, the racemic compound of Formula 1a is resolved via enantioselective esterification (step 1) by using a first lipase to form a mixture of an alcohol of Formula (S)-1e and a compound Formula (R)-1d. Then, the mixture can directly undergo a Mitsunobu reaction (step 2) to convert the alcohol of Formula (S)-1e into the compound of Formula (R)-1d,

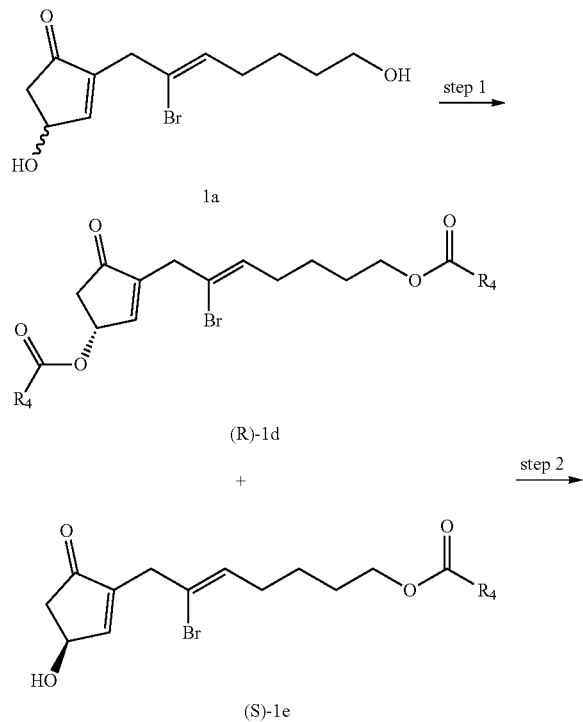

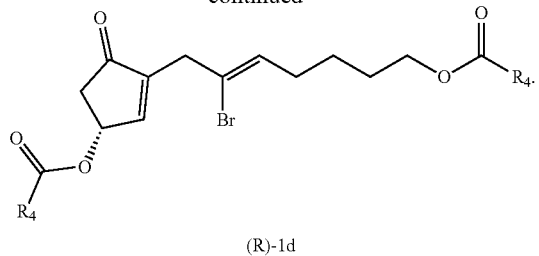

In step 1 of Scheme D, the enantioselective esterification of the compound of Formula (±)-1a is performed with a first lipase and an acyl donor of Formula D, wherein $R_4$ and $R_5$ are independently H or $C_{1-4}$ alkyl, in an organic solvent at an appropriate temperature to obtain the mixture of Formulae (R)-1d and (S)-1e,

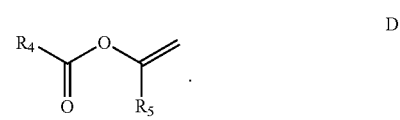

The examples of a suitable first lipase include, but are not limited to, *Burkholderia cepacia*, *Candida* antarctica, *Alcaligenese* sp., *Pseudomonas* stutzri, *Pseudomonas cepacia* and a mixture thereof, preferably *Burkholderia cepacia* or *Alcaligenese* sp., and most preferably *Burkholderia cepacia*.

The examples of a suitable acyl donor include, but are not limited to, vinyl acetate, isopropenyl acetate, vinyl valerate, isopropenyl valerate, vinyl butyrate, iso-propenyl butyrate, and a mixture thereof, and the vinyl acetate is particularly preferable. Furthermore, the reaction may be performed in a single organic solvent or a mixture of organic solvents, such as hexane, cyclohexane, toluene, tetrahydrofuran, methyl ethyl ketone, methyl isobutyl ketone, ether, isopropyl ether, methyl isopropyl ether, tert-butyl methyl ether and the mixture thereof. An appropriate reaction temperature is from about 5° C. to 50° C., particularly an ambient temperature.

In step 2 of Scheme D, the compound of Formula (S)-1e of the mixture obtained from step 1 of Scheme D, can be easily removed by column purification due to the difference of the polarity of alcohols and esters, so as to obtain the compound of Formula (R)-1d.

In some embodiments, it is not necessary to separate the compounds of Formulae (R)-1d and (S)-1e from the mixture obtained from step 1 of Scheme D. In-stead, a Mitsunobu inversion reaction may be subjected to convert the compound of Formula (S)-1e into a corresponding (R)-ester. The un-reacted compound of Formula (S)-1e can be treated with an acyloxy donor of Formula $R_4COOH$ (wherein $R_4$ is H or $C_{1-6}$ alkyl), and then converted into the compound of Formula (R)-1d in the presence of dialkylazodicarboxylate and trialkyl/triaryl phosphine in a suitable solvent. The examples of a suitable dialkylazodicarboxylate may include, but are not limited to, dimethyl azodicarboxylate (DMAD), diethyl azodicarboxylate (DEAD), diisopropyl azodicarboxylate (DIAD), di-tert-butyl azodicarboxylate (DTBAD), dibenzyl azodicarboxylate (DBAD), bis-trichloroethyl azodicarboxylate (BTCEAD), di-p-chlorobenzyl azodicarboxylate (DCAD), di-4-nitrobenzyl azodicarboxylate (DNAD), dicyclopentyl azodicarboxylate (DCpAD), and a mixture thereof; and the examples of a suitable trialkyl/triaryl phosphine may be tri-n-butyl phosphine, tri-phenylphosphine, or a mixture thereof; and triphenylphosphine is preferred. Moreover, a suitable solvent may include, but is not limited to, tetrahydrofuran, toluene, benzene, dimethylformamide, diethyl ether, acetonitrile, dichloromethane, and a mixture thereof in this reaction. The reaction is preferably carried out at a reaction temperature ranging from about −30° C. to about 70° C., particularly at ambient temperature.

Accordingly, the present invention provides a process for preparing a compound of Formula (R)-1d enriched in the (R)-enantiomer and having an optical purity of at least 95% enantiomeric excess,

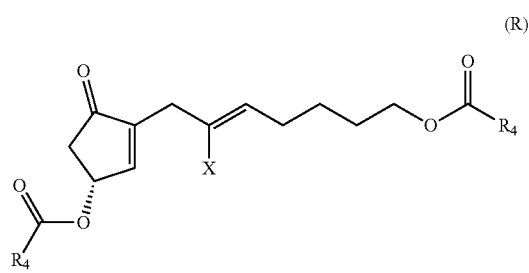

(R)-1d wherein X is F, Cl, Br, I, or —OTs; $R_4$ is H or $C_{1-6}$ alkyl, the process comprising the steps of:
(1) enantioselectively (R)-esterifying a compound of Formula 1a:

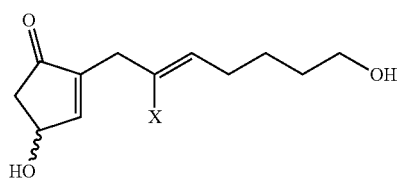

1a wherein X is F, Cl, Br, I, or —OTs, with an acyl donor of Formula D:

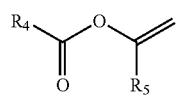

D wherein $R_4$ and $R_5$ are independently H or $C_{1-6}$ alkyl, and a first lipase, to form a mixture of a compound of Formula (R)-1d and a compound of Formula (S)-1e:

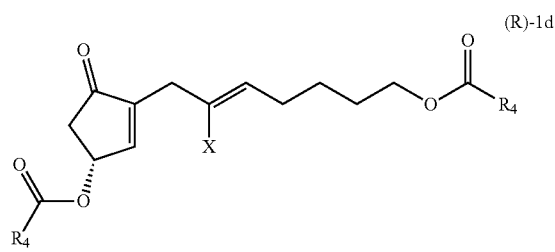

(R)-1d

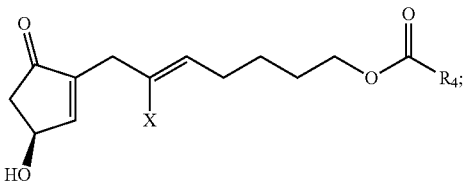

(S)-1e and
(2) removing the compound of Formula (S)-1e.

Synthetic Route of Optically Active Cyclopentenone, Formula (R)-1f

As shown in Scheme E, the cyclopentenone of Formula (R)-1d, wherein $R_4$ is H or $C_{1-6}$ alkyl, is deacylated to form the compound of Formula (R)-1a via an enzymatic cleavage reaction by using a lipase (step 1). Then, the hydroxyl group in the compound of Formula (R)-1a is protected to form the compound of Formula (R)-1f, Scheme E

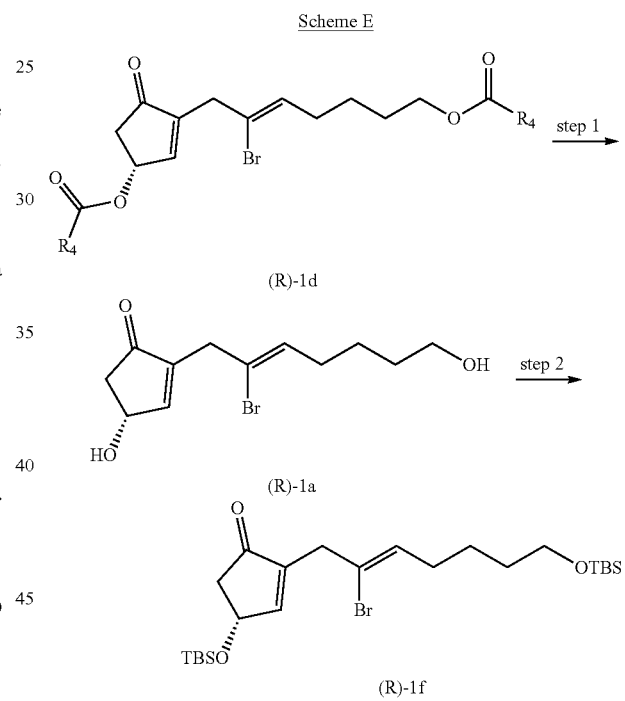

Step 1 of Scheme E is a deacylation reaction by using a chemical hydrolysis reaction or an enzymatic cleavage reaction. This reaction may be performed via an enzymatic cleavage reaction, in the presence of a commercially available lipase in a suitable organic solvent or aqueous system at an appropriate temperature to afford the compound of Formula (R)-1a. The examples of a suitable lipase include, but are not limited to, *Candida* antarcitica, *Burkholderia cepacia* or a mixture thereof and preferably from *Burkholderia cepacia*.

The deacetylation reaction is monitored for the purpose of an optical purity of the compound of Formula (R)-1a. In some embodiments, the deacetylation reaction is monitored by HPLC using a chiral column and stopped by removing the lipase, preferably when the optical purity of the resultant compound decreases to about 95% e.e., preferably about 99% e.e., and more preferably about 99.9% e.e.

Step 2 of Scheme E pertains to a protection reaction. The protection reaction may be carried out by using a suitable base reagent and tert-butyldimethylsilyl chloride at a temperature ranging from about 25° C. to about 80° C. A suitable base re-agent includes, but is not limited to, imidazole, triethyl amine, and a mixture thereof. The imidazole is more preferable in this step as a base reagent.

Synthetic Route of Optically Active Cyclopentenone, Formula (R)-1i

As shown in Scheme F, the cyclopentenone of Formula (R)-1d, wherein $R_4$ is H or $C_{1-6}$ alkyl, is selectivity deacylated to obtain the primary alcohol of Formula (R)-1g, wherein $R_4$ is as defined above, via an enzymatic cleavage reaction by using a lipase (step 1). Then, the hydroxyl group in Formula (R)-1g may be oxidized to afford a carbonyl acid for forming the compound of Formula (R)-1h, wherein $R_4$ is as defined above (step 2). Thereafter, the compound of Formula (R)-1h may be treated with an acid catalyst in an alcohol of $R_1OH$, wherein $R_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy, and the compound of Formula (R)-1i is obtained via deacylation and esterification (step 3). Finally the secondary alcohol of Formula (R)-1i is protected to generate the compound of Formula (R)-1j (step 4),

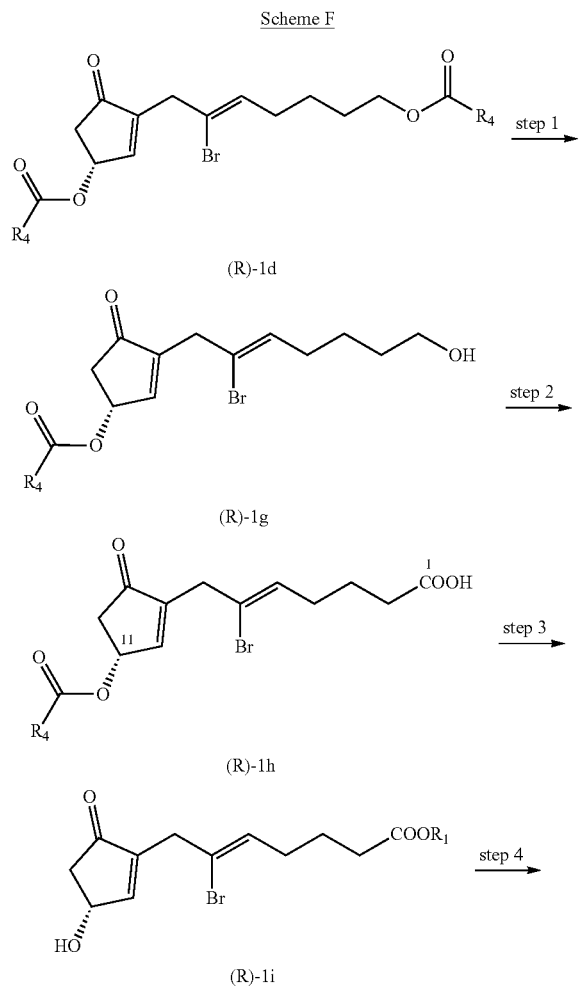

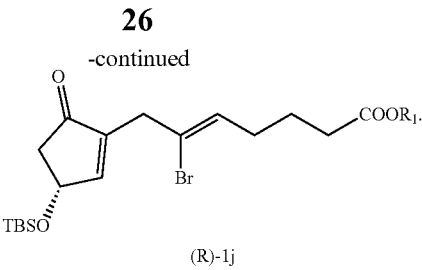

Step 1 of Scheme F pertains to a selectivity deacylation reaction. This reaction may be performed via an enzymatic cleavage reaction, in the presence of a commercially available lipase in a suitable organic solvent or aqueous system at an appropriate temperature to afford the compound of Formula (R)-1g. The examples of a preferable suitable lipase include *Candida cylindracea*, *Pseudomonas* stutzri, *Alcaligenese* sp., *Achromobacter* sp., *Burkholderia cepacia*, *Candida antarcitica* or a mixture thereof; more preferably, the lipase is derived from *Burkholderia cepacia*. or *Candida antarcitica*, and the most preferably from *Candida* antarcitica. The other operation conditions in this reaction are obvious in the art.

Step 2 of Scheme F pertains to an oxidation reaction. In this reaction, the primary alcohol of Formula (R)-1g is oxidized to afford a carbonyl acid group under suitable oxidation conditions. Suitable oxidants include, but are not limited to, potassium permanganate ($KMnO_4$), Jones reagent, pyridinium chlorochromate (PCC) in dimethylformamide (DMF), ruthenium tetroxide ($RuO_4$), 2,2,6,6-tetramethylpiperidine-1-oxyl (TEMPO), bis(acetoxy)iodobenzene (BAIB), and a mixture thereof, preferably 2,2,6,6-tetramethylpiperidine-1-oxyl (TEMPO)/Bis(acetoxy) iodobenzene (BAIB), for forming the compound of Formula (R)-1h.

Step 3 of Scheme F pertains to a one-step reaction, which involves deaceylation (at C11) and esterification reaction (at C1) of the compound of Formula (R)-1h. In some embodiments, the deaceylation of the aceyl group at C11 of the compound of Formula (R)-1h and the esterification reaction of the —COOH group at C1 of the compound of Formula (R)-1h are performed in the presence of an acid catalyst in an alcohol system. A suitable acid catalyst includes, but is not limited to, phosphoric acid, p-toluenesulfonic acid, hydrobromic acid, hydrochloric acid, nitric acid, sulfuric acid, and a mixture thereof. A suitable alcohol in the alcohol system includes, but is not limited to, methanol, ethanol, propanol, isopropanol, butanol, isobutanol, and a mixture thereof. For example, the deaceylation and esterification reactions of the compound of Formula (R)-1h are both performed in the presence of sulfuric acid and methanol.

Step 3 of Scheme F also pertains to a step-by-step reaction, which involves deaceylation and then esterification. The deaceylation may be performed via an enzymatic cleavage reaction, in the presence of a commercially available lipase in a suitable organic solvent or aqueous system at an appropriate temperature to afford the compound of Formula (R)-1h':

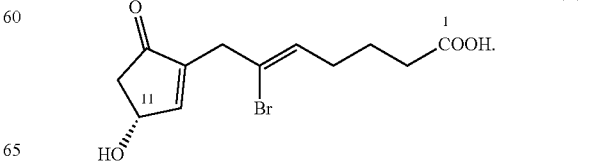

The examples of a preferable suitable lipase include, but are not limited to, *Candida cylindracea, Pseudomonas stutzri*, Alcaligenese sp., *Achromobacter* sp., *Burkholderia cepacia, Candida* antarcitica and a mixture thereof; and more preferably from Alcaligenese sp., *Burkholderia cepacia, Candida* antarcitica, and a mixture thereof; and most preferably from *Burkholderia cepacia*. The other operation conditions are obvious in the art.

Then, the compound of Formula (R)-1h' may be esterified with an alcohol of formula $R_1OH$, wherein $R_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy, to form the compound of Formula (R)-1i.

Sep 4 of Scheme F pertains to a protection reaction. The protection reaction may be carried out by using a suitable base reagent and tert-butyldimethylsilyl chloride at a temperature ranging from about 25° C. to about 80° C. A suitable base re-agent includes, but is not limited to, imidazole and triethyl amine. The imidazole is more preferable in this step as a base reagent.

Preparation of Compounds of Formula 4

The synthesis of the carbaprostacyclin analogues of Formula 4 starting from the compound of Formula 1, wherein Y is $—CH_2OP$ or $—COOR_1$; X is F, Cl, Br, I, or $—OTs$; $P_1$ is a hydroxyl protective group; P is H or a hydroxyl protective group; $R_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy; $R_2$ is H or $C_{1-4}$-alkyl; and $R_3$ is $C_{1-7}$-alkyl, $C_{2-7}$-alkynyl, aryl or aryloxy, each of which is unsubstituted or substituted by $C_{1-4}$-alkyl, halogen, or trihalomethyl; is based on the synthetic route as shown in Scheme G,

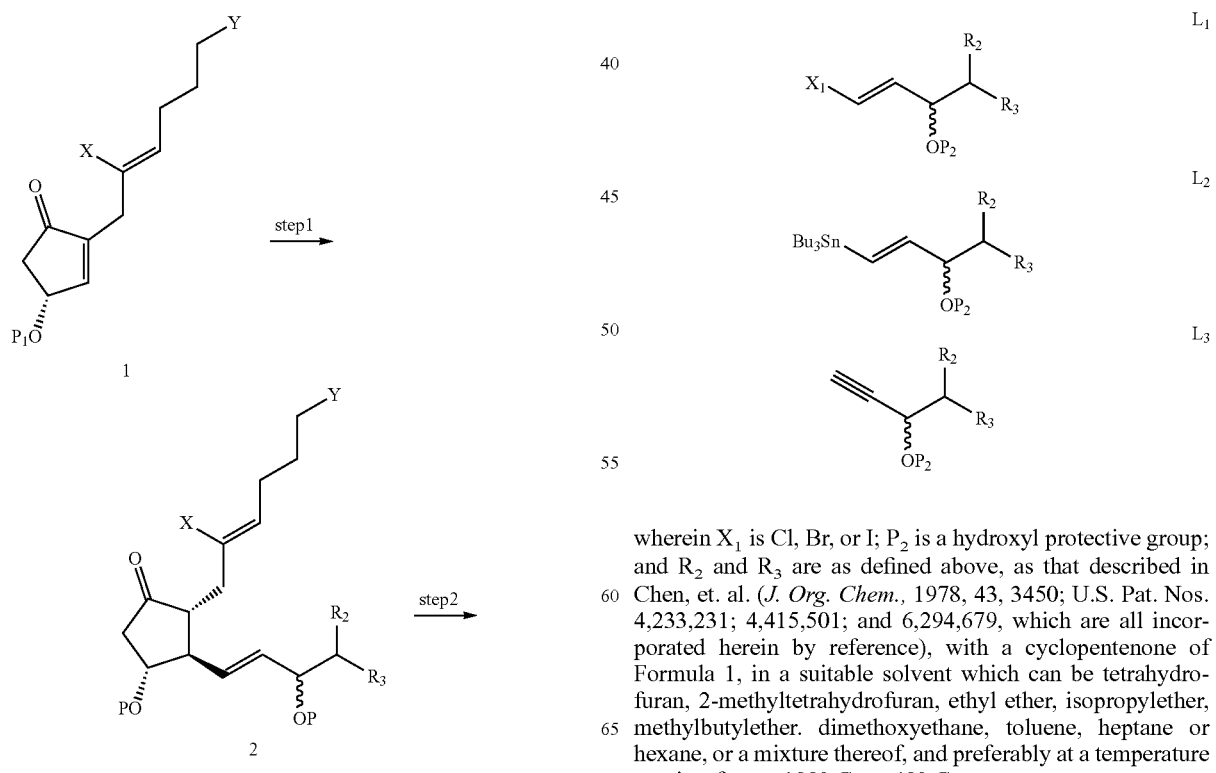

Scheme G

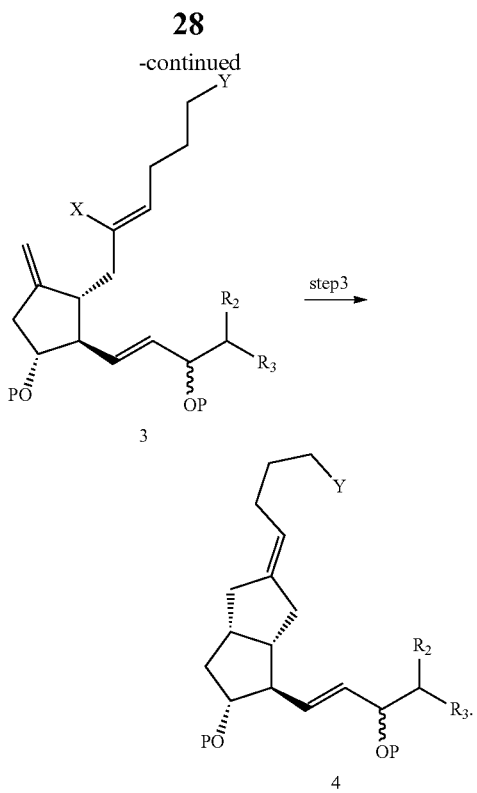

In step 1 of Scheme G, the cyclopentanone of Formula 2, wherein P, X, Y, $R_2$, and $R_3$ are as defined above, is prepared by a coupling reaction of an ω-side chain unit of a cuprate derived from a halide of Formula $L_1$, a vinyl stannane of Formula $L_2$ or an alkyne of Formula $L_3$, wherein $X_1$ is Cl, Br, or I; $P_2$ is a hydroxyl protective group; and $R_2$ and $R_3$ are as defined above, as that described in Chen, et. al. (*J. Org. Chem.*, 1978, 43, 3450; U.S. Pat. Nos. 4,233,231; 4,415,501; and 6,294,679, which are all incorporated herein by reference), with a cyclopentenone of Formula 1, in a suitable solvent which can be tetrahydrofuran, 2-methyltetrahydrofuran, ethyl ether, isopropylether, methylbutylether. dimethoxyethane, toluene, heptane or hexane, or a mixture thereof, and preferably at a temperature ranging from −100° C. to 40° C.

Step 2 of Scheme G involves an olefination reaction. In this reaction, the carbonyl group in Formula 2 is converted to a terminal double bond under olefination conditions, such as, Peterson olefination, Julia olefination, Wittig olefination, Kauff-mann olefination, Tebbe olefination, and Nysted's olefination. Preferably, the compound of Formula 2 is treated with a Nozaki-Lombardo reagent (see *Bull. Chem. Soc. Jpn.*, 53.1698(1980)) which may be prepared from dibromomethane, zinc, and titanium (IV) chloride, to form the compound of Formula 3. The reaction can be con-ducted in any suitable solvent, such as that selected from dichloromethane, tetrahydrofuran, ether, toluene, hexane, and a mixture thereof. The reaction can be carried out at a temperature ranging from −50° C. to 100° C., preferably from −20° C. to the room temperature. The Nozaki-Lombardo reagent can be used in an amount such that the reactants are completely reacted as monitored by Thin Layer Chromatography (TLC). Upon completion of the reaction, the compound of Formula 3 can be isolated from the reaction mixture by a work-up procedure such as removing the excessive reagent, ex-traction, dehydration, concentration, and the like.

In some embodiments, the methylene group can also be introduced by a two-step procedure as taught by Johnson in *J. Am. Chem. Soc.* 95, 6462(1973). For example, the cyclopentanone of Formula 2 is reacted with an anion of methylphenyl-N-methyl-sulfoximine in a suitable solvent followed by treatment of the resulting crude adduct with alumimum amalgam in a solvent mixture of water-acetic acid-tetrahydrofuran so as to obtain the compound of Formula 3.

Step 3 of Scheme G pertains to an intramolecular cross-coupling reaction, i.e., an intramolecular cyclization or an intramolecular Suzuki reaction. The intramolecular cyclization reaction is an intramolecular Suzuki reaction with a boron reagent using a palladium catalyst and a base to form the compound of Formula 4. In this step, the intramolecular cross-coupling reaction involves two stages, regioselectivity hydroboration and Suzuki reaction as shown in Scheme G-1, Scheme G-1

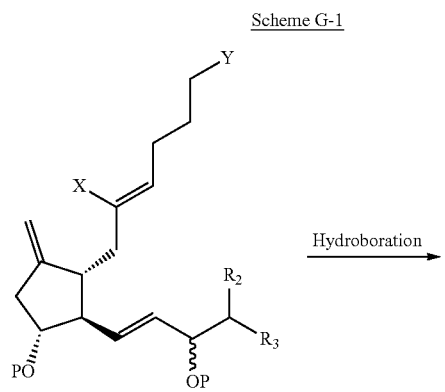

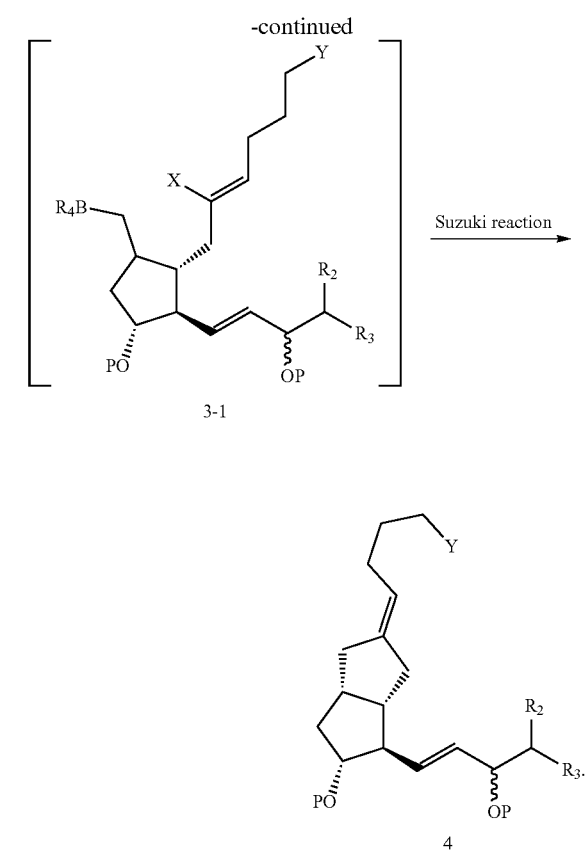

At the first stage, the compound of Formula 3 may be treated with a boran reagent via regioselectivity hydroboration, and then the terminal double bond in Formula 3 is converted to form an alkyl-9-borane intermediate of Formula 3-1. A suitable boron reagent may be 9-borabicyclo [3.3.1]nonane (9-BBN), disiamylborane, diisoamylborane, catecholborane, diisopinocamphenylborane, dicyclohexylborane, bis(pinacolato)diborane, or a mixture thereof. The 9-borabicyclo[3.3.1]nonane (9-BBN) is more preferable in this step as the boron reagent.

The second stage involves treatment of the intermediate of Formula 3-1 with a palladium catalyst for forming the compound of Formula 4 via Suzuki cross-coupling in the presence of a base reagent at a temperature ranging from about 50° C. to about 60° C. under nitrogen or argon. A suitable palladium catalyst includes, but is not limited to, $Pd(PPh_3)_4$, $Pd(dppf)_2Cl_2$-DCM, $Pd(dppf)_2Cl_2$, $Pd(OAc)_2$, $Pd_2(dba)_2$, bis(η3-allyl-μ-chloropalladiun(II)), and a mixture thereof. And a suitable base reagent can increase the reactivity of the alkyl borane toward forming a Pd-halide complex to promote the cross-coupling rate, which includes, but is not limited to $Li_2CO_3$, $Na_2CO_3$, $K_2CO_3$, $Cs_2CO_3$, NaOMe, $K_3PO_4$, t-BuONa, t-BuOK, $K_3PO_4$, NaOH, and a mixture thereof. In some embodiments, the Suzuki cross-coupling reaction is performed in the presence of $Pd(dppf)_2Cl_2$ and $Na_2CO_3$ at 60° C. in tetrahydro-furan solvent.

Step 3 of Scheme G pertains to an intramolecular cross-coupling reaction. In some embodiments, the intramolecular cross-coupling reaction involves three stages, hydroboration-oxidation (step 3-1), alkylsulfonation (step 3-2), and intramolecular cross-coupling reaction (step 3-3) as shown in Scheme G-2, Scheme G-2

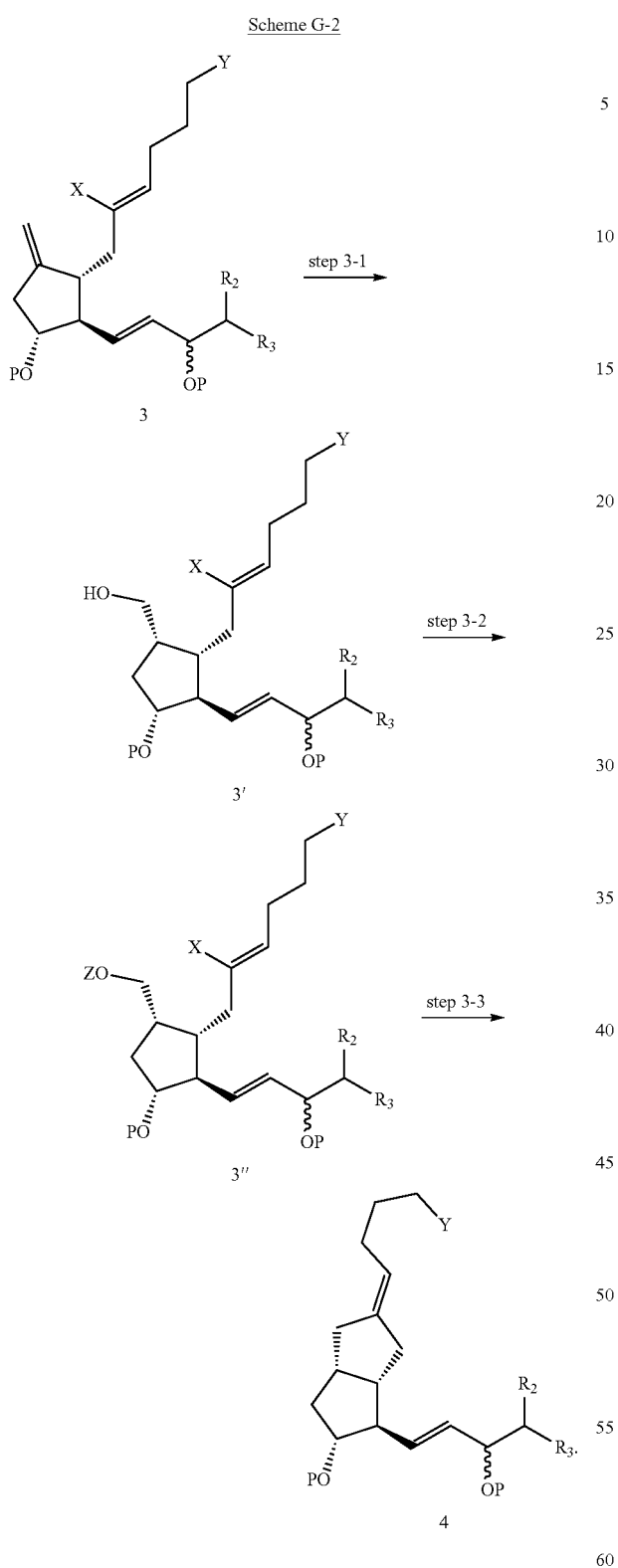

Step 3-1 of Scheme G-2 pertains to a hydroboration-oxidation reaction. The compound of Formula 3 is reacted with a boron reagent, followed by oxidation with basic hydrogen peroxide so as to give the alcohol compound of Formula 3'. A suitable boran reagent includes, but is not limited to, $Py_2BH_2$, sodium tetrahydrobo-rate, borane-THF, borane-DMS and 9-BBN.

In step 3-2 of Scheme G-2, the alcohol compound of Formula 3' is further subjected to a sulfonylation reaction to obtain the compound of Formula 3", wherein Z is a sulfonyl group consisting of alkylsulfonyl, arylsulfonyl, and aralkylsulfonyl, such as methanesulfonyl or p-toluenesulfonyl. The sulfonylation reaction is achieved in the presence of a base, such as an amine, e.g., triethylamine, by using an appropriate sulfonyl donor, such as methanesulfonyl chloride or p-toluenesulfonyl chloride.

Step 3-3 of Scheme G-2 pertains to an intramolecular cross-coupling reaction. The carbaprostacyclin analogue of Formula 4 is prepared by an intramolecular cyclization reaction of the compound of Formula 3" under a suitable base condition. In some embodiments, the intramolecular cyclization reaction is achieved by using a suitable base in a suitable solvent at a temperature ranging from about −70° C. to about −50° C. A suitable base includes, but is not limited to, n-butyllithium, sec-butyllithium, tert-butyllithium, and a mixture thereof. A suitable solvent includes, but is not limited to, tetrahydrofuran, ether, toluene, and a mixture thereof.

Accordingly, the present invention provides a process for preparing the compound of Formula 4:

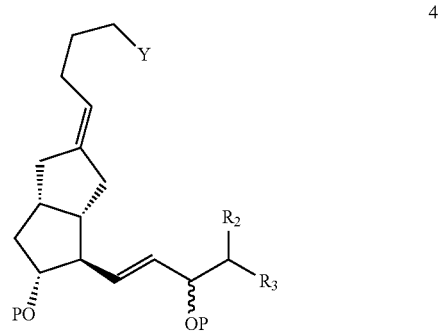

wherein Y is —$CH_2OP$ or —$COOR_1$; P is H or a hydroxyl protective group; $R_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy; $R_2$ is H or $C_{1-4}$-alkyl; and $R_3$ is $C_{1-7}$-alkyl, $C_{1-7}$-alkynyl, aryl or aryloxy, each of which is unsubstituted or substituted by $C_{1-4}$-alkyl, halogen, or trihalomethyl, the process comprising the steps of:

(1) reacting a starting compound of Formula 1:

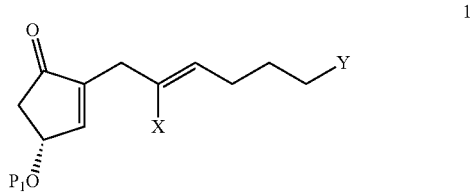

wherein X is F, Cl, Br, I, or —OTs; $P_1$ is a hydroxyl protective group; and Y is as defined above, with a starting cuprate derived from a compound of Formula $L_1$, Formula $L_2$, or Formula $L_3$:

L₁

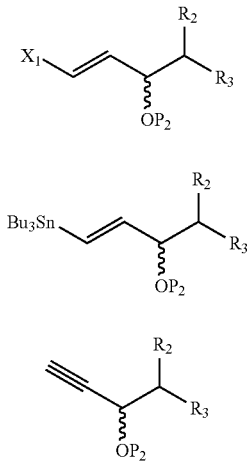

L₂

L₃ wherein X1 is Cl, Br, or I; P₂ is a hydroxyl protective group; and R₂ and R₃ are as defined above, to form a compound of Formula 2:

2

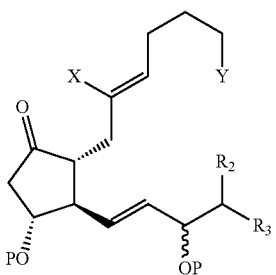

wherein P, X, Y, R₂ and R₃ are as defined above:

(2) methylenation of a ketone radical of the compound of Formula 2 to form a compound of the following formula 3:

3

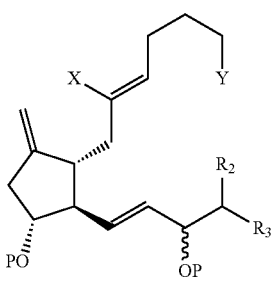

wherein P, X, Y, R₂ and R₃ are as defined above;

(3) performing an intramolecular cyclization reaction to the compound of Formula 3 to form the compound of Formula 4:

4

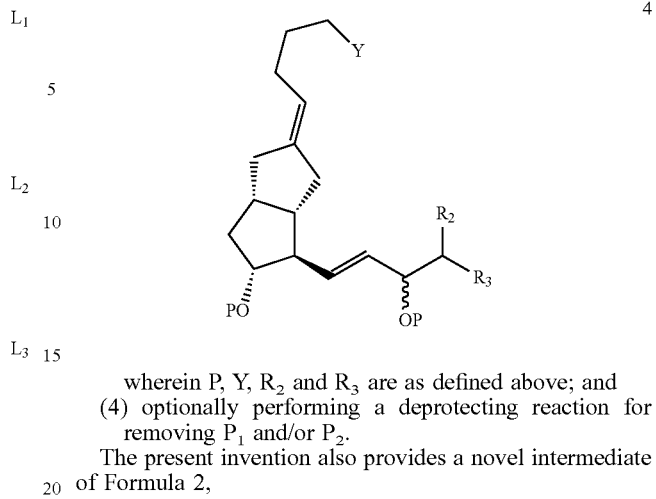

wherein P, Y, R₂ and R₃ are as defined above; and (4) optionally performing a deprotecting reaction for removing P₁ and/or P₂.

The present invention also provides a novel intermediate of Formula 2,

2

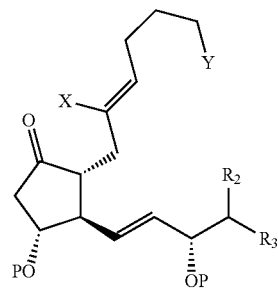

wherein Y is —CH₂OP or —COOR₁; X is F, Cl, Br, I, or —OTs; P is H or a hydroxyl protective group; R₁ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy; R₂ is H or $C_{1-4}$-alkyl; and R₃ is $C_{1-7}$-alkyl, $C_{2-7}$-alkynyl, aryl, or aryloxy, each of which is unsubstituted or substituted by Cia-alkyl, halogen, or a trihalomethyl.

The present invention also provides a novel intermediate of Formula 3.

3

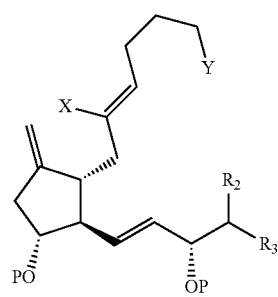

wherein Y is —CH₂OP or —COOR₁; X is F, Cl, Br, I, or —OTs; P is H or a hydroxyl protective group; R₁ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy; R₂ is H or $C_{1-4}$-alkyl; and R₃ is $C_{1-7}$-alkyl, $C_{2-7}$-alkynyl, aryl, or aryloxy, each of which is unsubstituted or substituted by $C_{1-4}$-alkyl, halogen, or a trihalomethyl.

The present invention also provides a novel intermediate of Formula 3″,

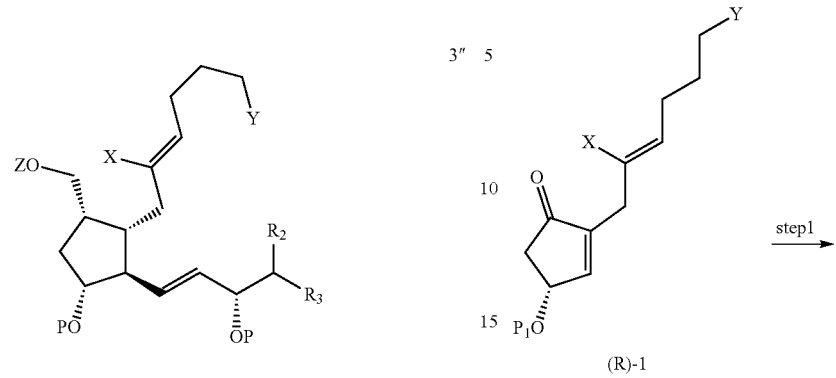

3″ wherein Y is —CH$_2$OP or —COOR$_1$; X is F, Cl, Br, I, or —OTs; Z is H or a sulfonyl group; P is H or a hydroxyl protective group; R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy; R$_2$ is H or C$_{1-4}$-alkyl; and R$_3$ is C$_{1-7}$-alkyl, C$_{2-7}$-alkynyl, aryl, or aryloxy, each of which is unsubstituted or substituted by C$_{1-4}$-alkyl, halogen, or trihalomethyl.

The intermediate of Formula 3″ is preferably a compound of Formula 3″a or a compound of Formula 3″b:

3′a

3′b wherein Y, X, Z, and P are as defined above.

Synthetic Route of Formula 4a which is Used for Forming 16S-Iloprost

As depicted in Scheme H, the synthesis of the compound of Formula 4a is similar to that of Formula 4 as shown in Scheme G,

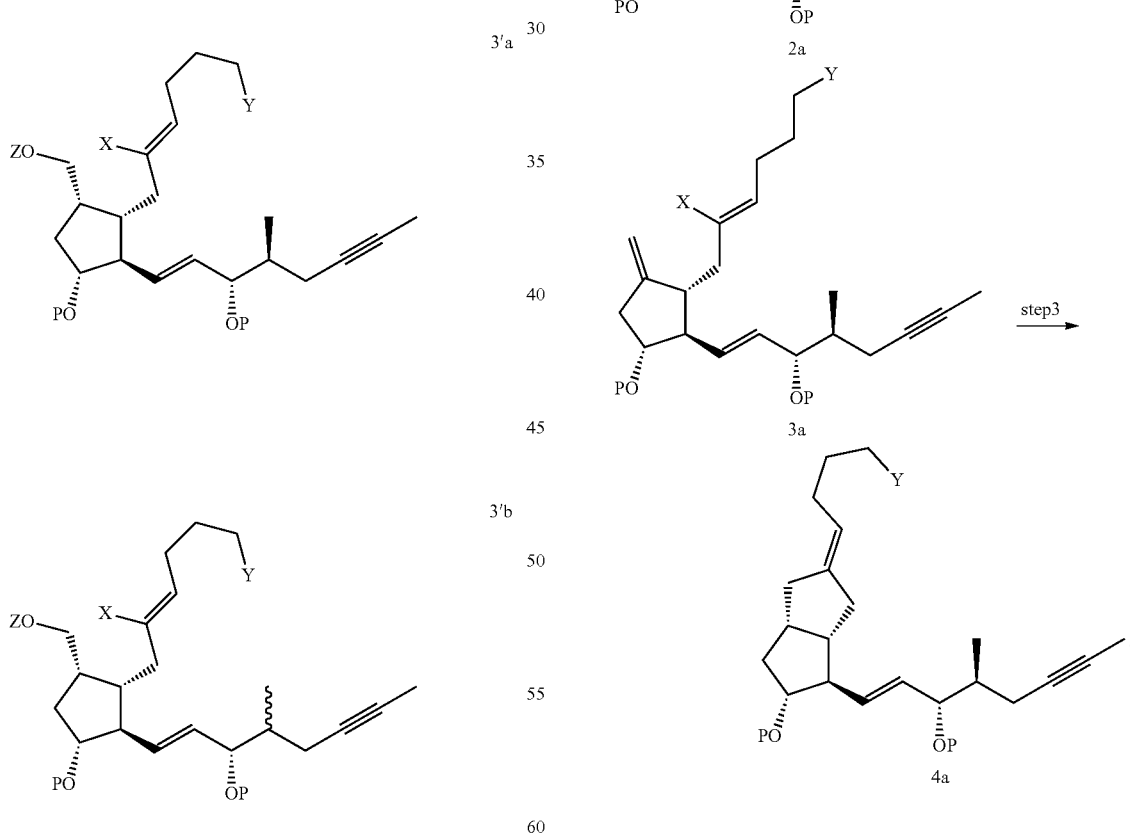

Scheme H

The synthesis of the compound of Formula 4a starts from an optically enriched compound of Formula (R)-1, wherein Y is —CH$_2$OP or —COOR$_1$; X is F, Cl, Br, I, or —OTs; P$_1$ is a hydroxyl protective group; P is H or a hydroxyl protective group; R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy, and an optically enriched (3S, 4S)-compound of Formula L$_1$, Formula L$_2$, or Formula L$_3$, wherein X$_1$ is Cl, Br, or I; and P$_2$ is a hydroxyl protective group,

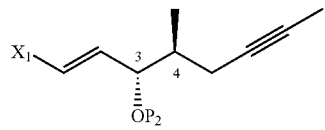

L$_{1a}$

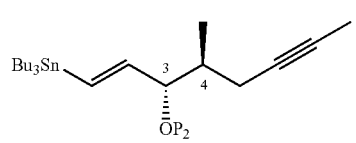

L$_{2a}$

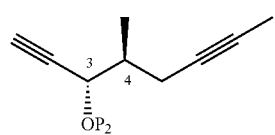

L$_{3a}$

As shown in Scheme H, the compound of Formula 2a is prepared by a coupling reaction of an enantiomerically enriched ω-side chain unit of a cuprate de-rived from a halide of Formula L$_1$, a vinyl stannane of Formula L$_2$ or an alkyne of Formula L$_3$, with a cyclopentenone of Formula (R)-1, to form the compound of Formula 2a (step 1). Thereafter, the compound of Formula 2a is subjected to an olefination reaction (step 2) and an intramolecular cyclization reaction (step 3) to form the compound of Formula 4a. In some embodiments, the intramolecular cyclization reaction is an intramolecular Suzuki reaction with a boron reagent using a palladium catalyst and a base to form the compound of Formula 4a.

Accordingly, the present invention provides a process for preparing a compound of Formula 4a:

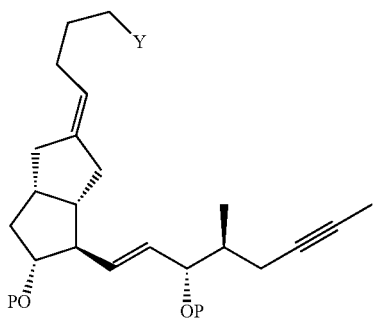

4a wherein Y is —CH$_2$OP or —COOR$_1$; P is H or a hydroxyl protective group; and R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy, the process comprising the steps of:

(1) reacting an optically enriched compound of Formula (R)-1:

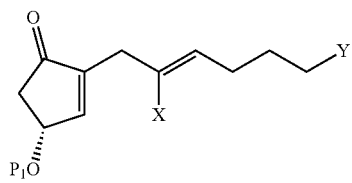

(R)-1 wherein X is F, Cl, Br, I, or —OTs; P$_1$ is a hydroxyl protective group; and Y is as defined above, with a cuprate derived from a compound of Formula L$_1$s, Formula L$_2$, or Formula L$_3$:

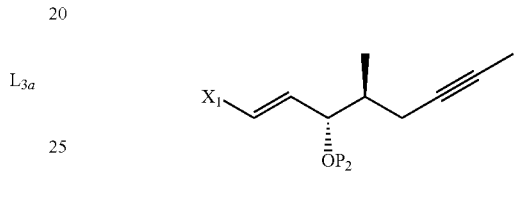

L$_{1a}$

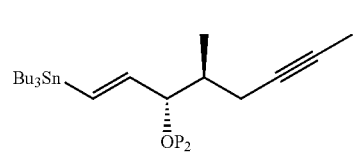

L$_{2a}$

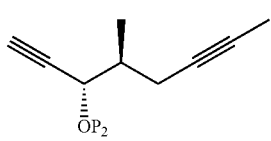

L$_{3a}$ wherein X$_1$ is Cl, Br, or I; and P$_2$ is a hydroxyl protective group, to form a compound of Formula 2a:

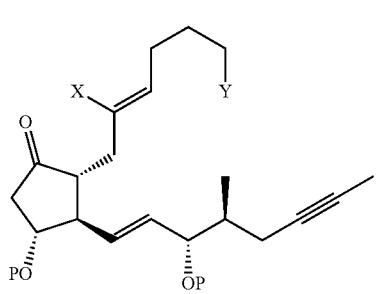

2a wherein P, X, and Y are as defined above;

(2) methylenation of a ketone radical of the compound of Formula 2a to form a compound of Formula 3a:

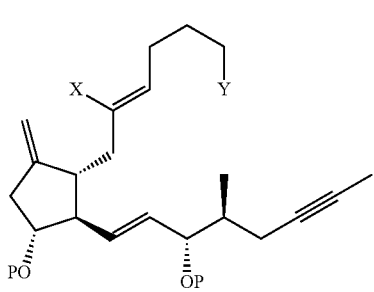

3a wherein P, X, and Y are as defined above;

(3) performing an intramolecular cyclization reaction to the compound of Formula 3a to form the compound of Formula 4a:

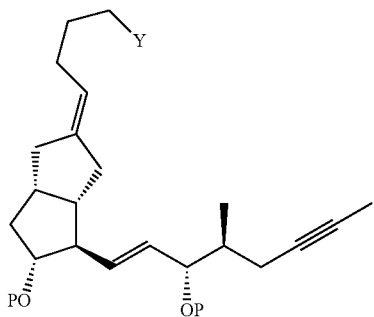

4a wherein P and Y are as defined above; and (4) optionally performing a deprotecting reaction for removing $P_1$ and/or $P_2$.

In this process, the intramolecular cyclization reaction comprises the steps of:

(1) hydroboration of the compound of Formula 3a with a boron reagent, followed by oxidation with basic hydrogen peroxide to form an alcohol compound of Formula 4a-1:

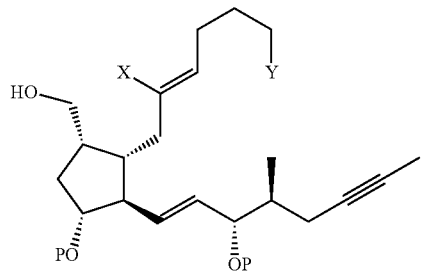

4a-1 wherein P, X and Y are as defined above;

(2) sulfonylation of the compound of Formula 4a-1 in the presence of a base with a sulfonyl donor to form a compound of Formula 4a-2:

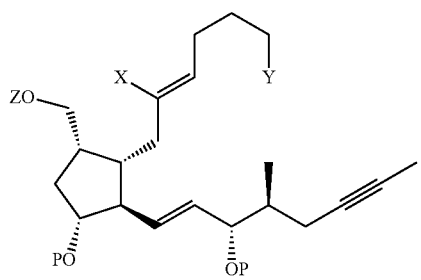

4a-2 wherein Z is a sulfonyl group; and P, X and Y are as defined above; and (3) intramolecular alkylation of the compound of Formula 4a-2 in the presence of a base to form the compound of Formula 4a:

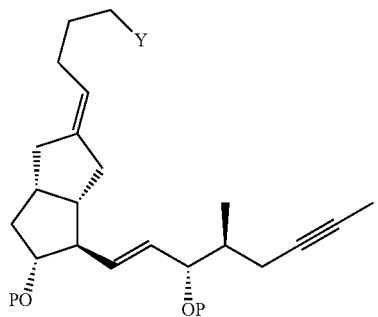

4a wherein Y and P are as defined above.

The present invention also provides a novel intermediate of Formula 2a of 3a:

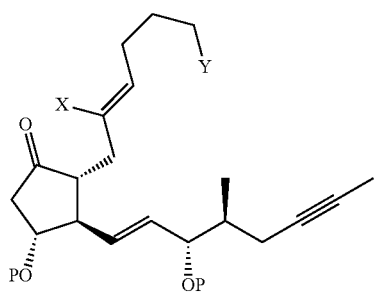

2a

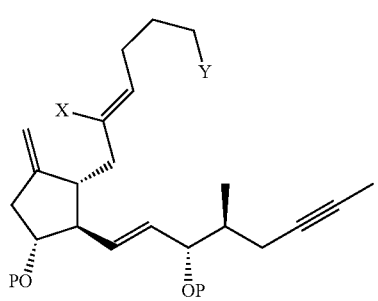

3a wherein Y is —CH$_2$OP or —COOR$_1$; X is F, Cl, Br, I, or —OTs; and P is H or a hydroxyl protective group.

Synthesis of 16S-Iloprost

Scheme I depicts the synthesis of 16S-Iloprost from the compound of Formula (R)-1' (Y is —COOR$_1$ and R$_1$ is methyl in Formula (R)-1),

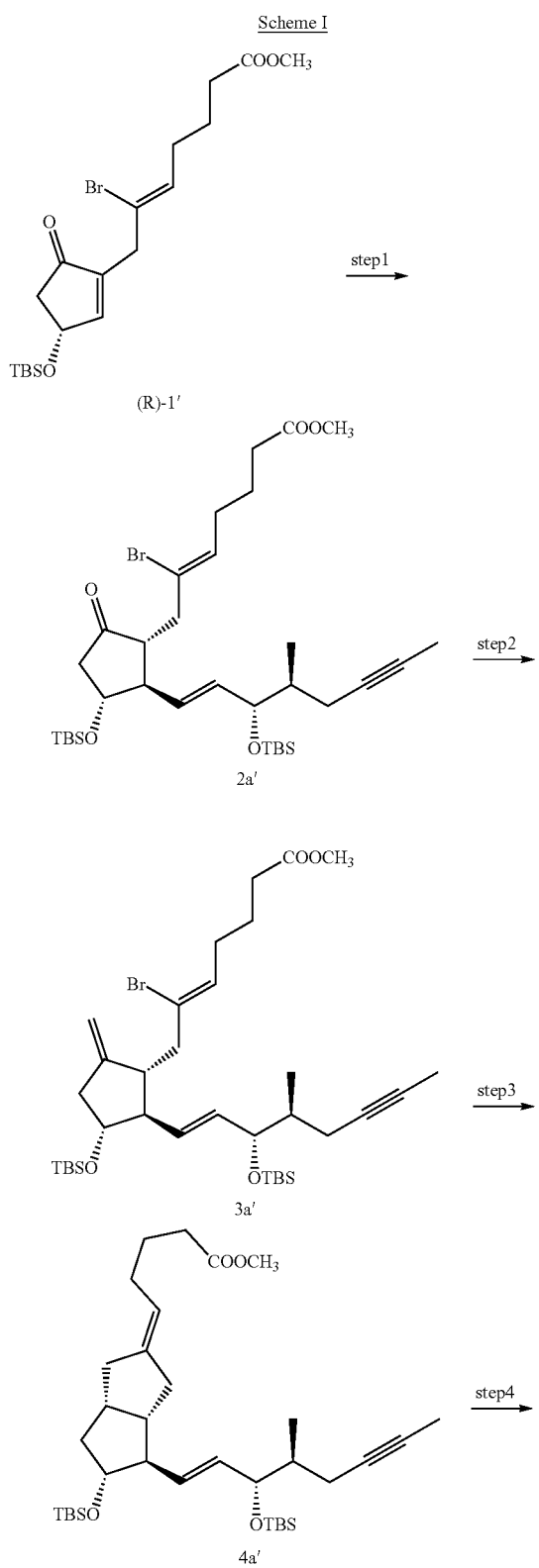

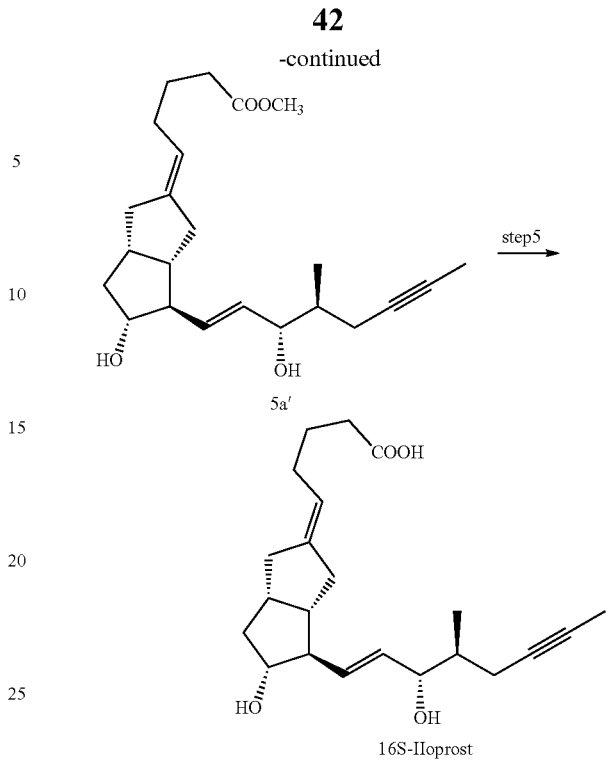

As shown in Scheme I, the methyl ester of TBS-protected 16S-Iloprost of Formula 4a' is prepared from the compound of Formula (R)-1', which contains less than 0.5% geometric isomer (E-isomer), and a cuprate derived from an optically enriched (3S, 4S)-compound of Formula L$_{2a}$

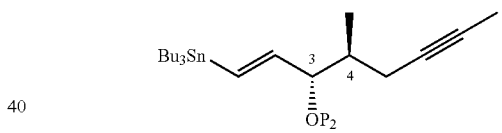

wherein P$_2$ is a hydroxyl protective group) via a coupling reaction to form a compound of Formula 2a' (step 1). The coupling product of Formula 2a' is converted to afford a terminal double bond under an olefination with CH$_2$Br$_2$—Zn in the presence of a Lewis acid, such as TiCl$_4$, for forming the compound of Formula 3a' (step 2). The compound of Formula 3a' is subjected to an intramolecular Suzuki cross-coupling reaction with a boron reagent, 9-borabicyclo[3.3.1]nonane (9-BBN), in the presence of Pd(dppf)$_2$Cl$_2$ and Na$_2$CO$_3$, to form the compound of Formula 4a' (step 3). The use of TBAF to re-move the TBS protective group of the compound of Formula 4a' to form the compound of Formula 5a' (step 4), and a hydrolysis step is carried out under alkaline conditions to form 16S-Iloprost (step 5).

HPLC analysis shows that the geometric isomer (Z-isomer) of the obtained crude 16S-Iloprost is less than 0.5%, which meets the quality requirement of less than or equal to 0.6% as disclosed in WO 2019/202345. Thus, compared to the conventional method for synthesis of 16S-Iloprost of WO 2019/202345, the process of the present invention comprises fewer steps and has higher yields, and the geometric isomer (Z-isomer) in the resultant crude 16S-Iloprost can be controlled to be less than 0.6% such that an expensive preparative HPLC method is unnecessary and thus the costs for separation and purification of 16S-Iloprost can be significantly reduced.

Synthetic Route of Formula 4b which is Used for Forming Iloprost

As depicted in Scheme J, the synthesis of the compound of Formula 4b is similar to that of Formula 4 as shown in Scheme G or that of Formula 4a as shown in Scheme H, Scheme J

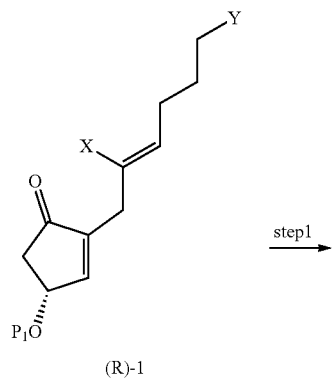

(R)-1

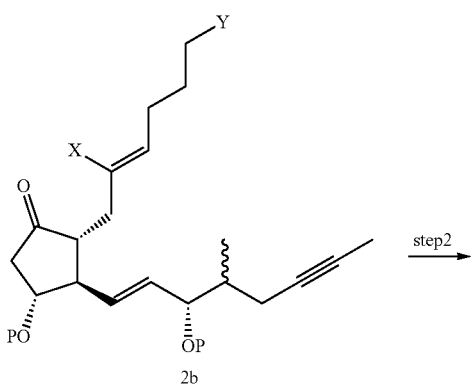

2b

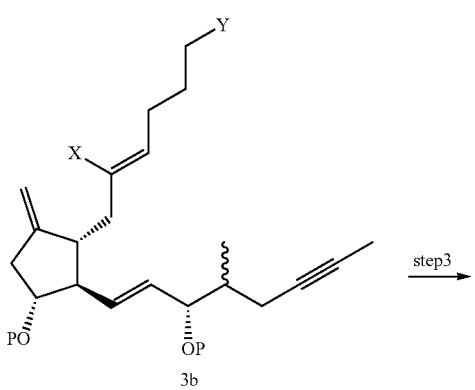

3b

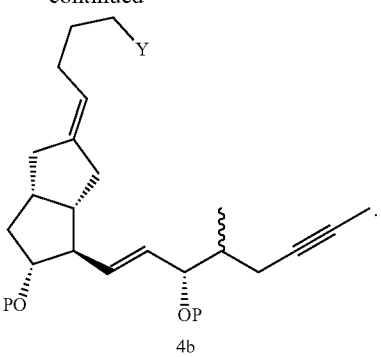

4b

The synthesis of the compound of Formula 4b starts from an optically enriched compound of Formula (R)-1, wherein Y is —CH$_2$OP or —COOR$_1$; X is F, Cl, Br, I, or —OTs; P$_1$ is a hydroxyl protective group; P is H or a hydroxyl protective group; R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy, and a optically enriched (3S, 4S and 4R)-compound of Formula L$_{1b}$, Formula L$_{2b}$ or Formula L$_{3b}$,

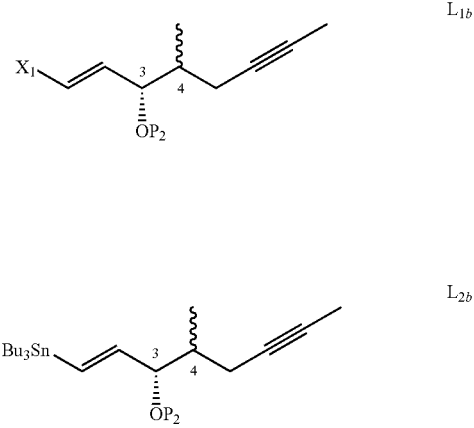

wherein X$_1$ is Cl, Br, or I; and P$_2$ is a hydroxyl protective group, in the same manufacturing process as shown in Scheme G or H. The compound of Formula 4b can be prepared according to the reactions shown in Scheme J via a coupling reaction to form a compound of Formula 2b (step 1). Thereafter, the compound of Formula 2b is subjected to an olefination reaction (step 2) and an intramolecular cyclization reaction (step 3) to form a compound of Formula 4b.

Accordingly, the present invention provides a process for preparing a compound of Formula 4b:

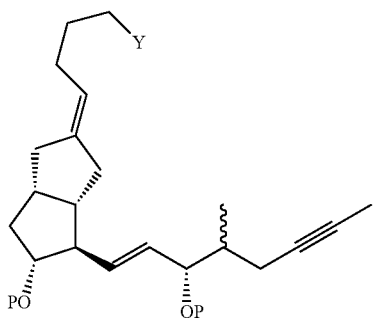

4b wherein Y is —CH$_2$OP or —COOR$_1$; P is H or a hydroxyl protective group; and R$_1$ is C$_{1-7}$-alkyl, aryl or aralkyl, each of which is unsubstituted or substituted by C$_{1-4}$-alkyl, C$_{2-7}$-alkenyl, C$_{2-7}$-alkynyl, nitro, halogen or alkoxy, the process comprising the steps of:

(1) reacting an optically enriched compound of Formula (R)-1:

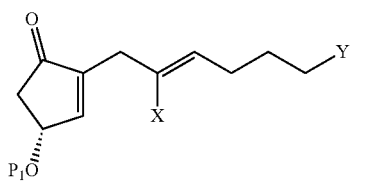

(R)-1 wherein X is F, Cl, Br, I, or —OTs; P$_1$ is a hydroxyl protective group; and Y is as defined above, with a cuprate derived from a compound of Formula L$_{1b}$, Formula L$_{2b}$, or Formula L$_{3b}$,

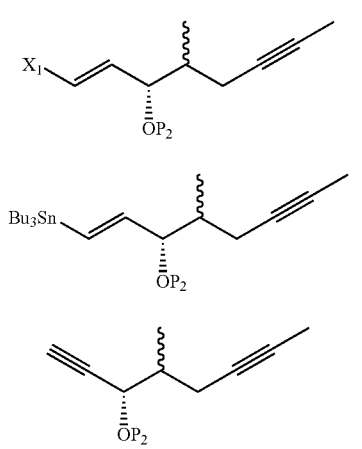

L$_{1b}$

L$_{2b}$

L$_{3b}$ wherein X$_1$ is Cl, Br, or I; and P$_2$ is a hydroxyl protective group, to form a compound of Formula 2b.

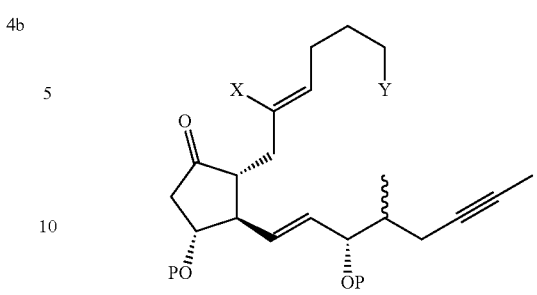

2b wherein P, X and Y are as defined above;

(2) methylenation of a ketone radical of the compound of Formula 2b to form a compound of Formula 3b:

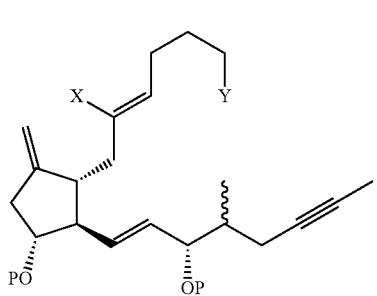

3b wherein P, X and Y are as defined above;

(3) performing an intramolecular cyclization reaction to the compound of Formula 3b to form a compound of Formula 4b:

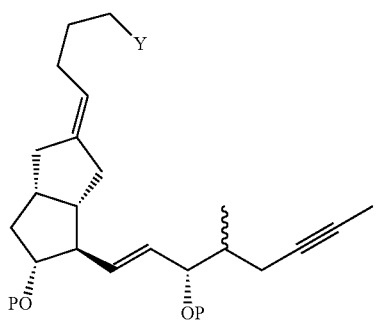

4b

P and Y are as defined above; and (4) optionally performing a deprotecting reaction for removing P$_1$ and/or P$_2$.

In this process, the intramolecular cyclization reaction comprises the steps of:

(1) hydroboration of the compound of Formula 3b with a boron reagent, followed by oxidation with basic hydrogen peroxide to form a compound of Formula 4b-1:

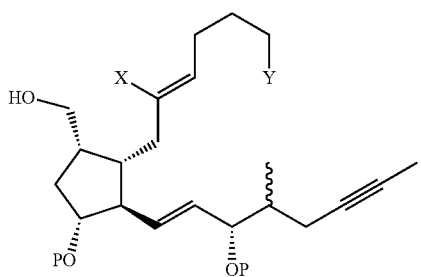

4b-1

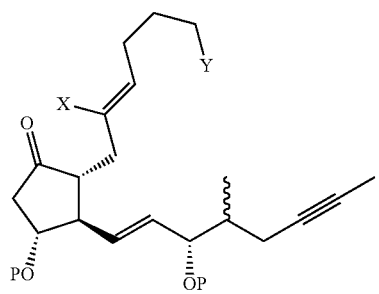

2b wherein P, X and Y are as defined above;

(2) sulfonylation of the compound of Formula 4b-1 in the presence of a base with a sulfonyl donor to form a compound of Formula 4b-2:

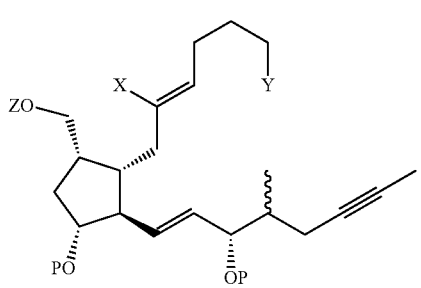

4b-2

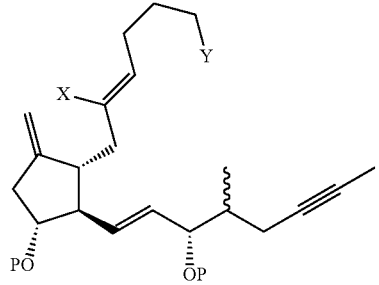

3b wherein Z is a sulfonyl group; and P, X and Y are as defined above; and (3) intramolecular alkylation of the compound of Formula 4b-2 in the presence of a base to form the compound of Formula 4b:

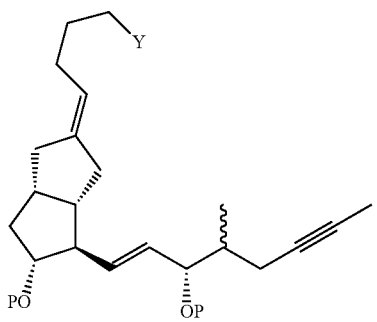

4b wherein P and Y are as defined above.

The present invention also provides a novel intermediate of Formula 2b or 3b:

wherein Y is —$CH_2OP$ or —$COOR_1$; X is F, Cl, Br, I, or —OTs; P is H or a hydroxyl protective group; and $R_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy.

Synthesis of Iloprost from the Compound of Formula (R)-1″, Wherein Y is —$CH_2OP$ As shown in Scheme J-1, Scheme J-1

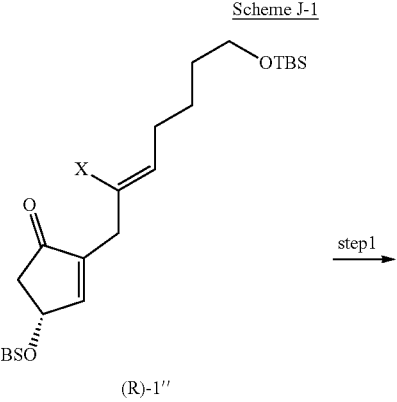

(R)-1″ step1

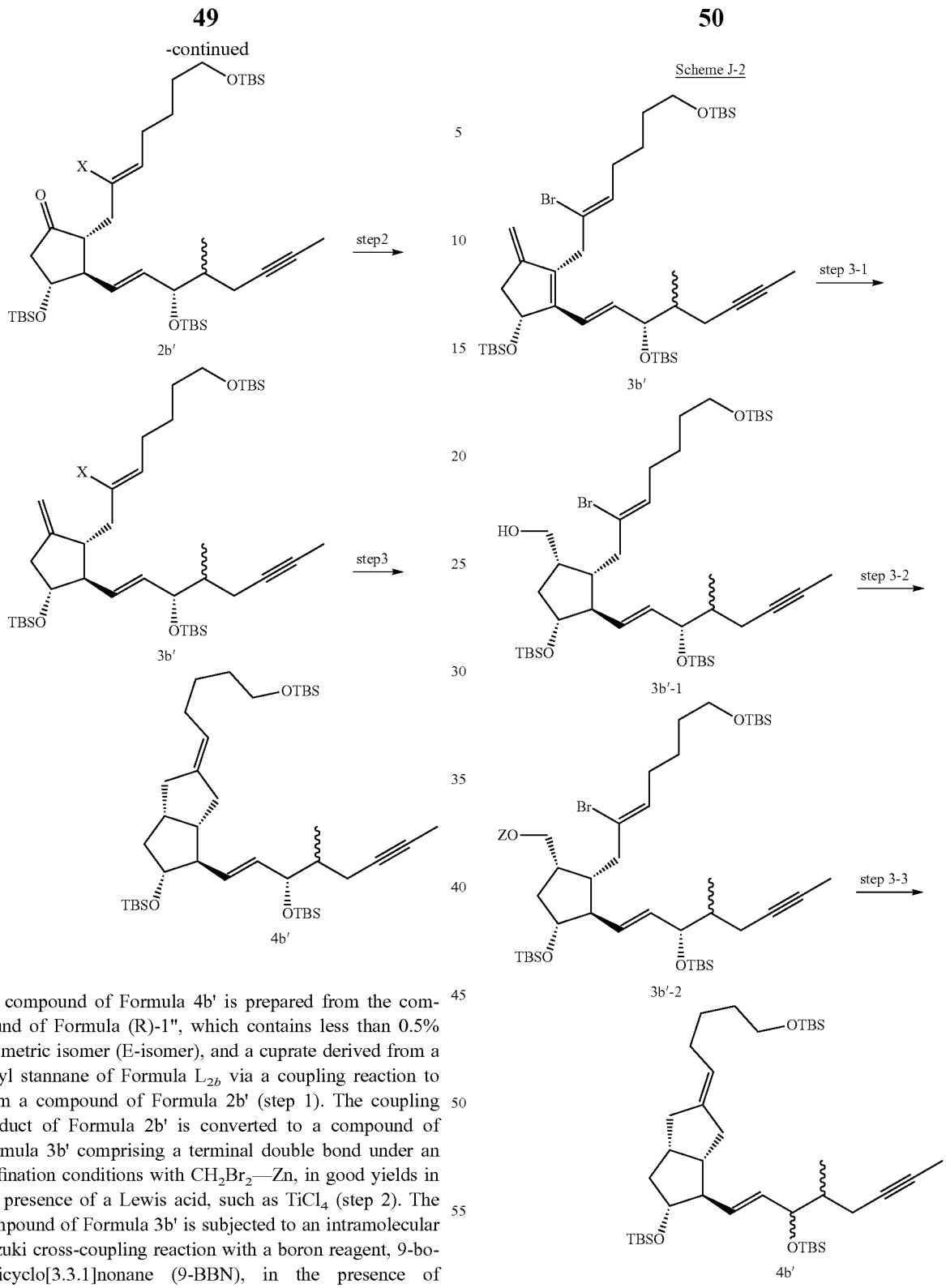

Scheme J-2 the compound of Formula 4b' is prepared from the compound of Formula (R)-1'', which contains less than 0.5% geometric isomer (E-isomer), and a cuprate derived from a vinyl stannane of Formula L$_{2b}$ via a coupling reaction to form a compound of Formula 2b' (step 1). The coupling product of Formula 2b' is converted to a compound of Formula 3b' comprising a terminal double bond under an olefination conditions with CH$_2$Br$_2$—Zn, in good yields in the presence of a Lewis acid, such as TiCl$_4$ (step 2). The compound of Formula 3b' is subjected to an intramolecular Suzuki cross-coupling reaction with a boron reagent, 9-borabicyclo[3.3.1]nonane (9-BBN), in the presence of Pd(dppf)$_2$Cl$_2$ and Na$_2$CO$_3$, to form the compound of Formula 4b'(step 3).

The compound of Formula 3b' is also subjected to an intramolecular cross-coupling reaction. The intramolecular cross-coupling reaction involves three stages, hydroboration-oxidation (step 3-1), alkyl sulfonation (step 3-2) and intramolecular cross-coupling reaction (step 3-3) as shown in Scheme J-2.

Step 3-1 of Scheme J-2 pertains to a hydroboration-oxidation reaction. The compound of Formula 3b' is reacted with a boron reagent, followed by oxidation with basic hydrogen peroxide so as to give the alcohol compound of Formula 3b'-1. A suitable boron reagent includes, but is not limited to, Py$_2$BH$_2$, sodium tetrahydroborate, borane-THF, borane-DMS and 9-BBN.

In Step 3-2 of Scheme J-2, the alcohol compound of Formula 3b'-1 is further subjected to a sulfonylation reaction to obtain a compound of Formula 3b'-2, wherein Z is a sulfonyl group consisting of alkylsulfonyl, arylsulfonyl and aralkyl-sulfonyl, such as methanesulfonyl or p-toluenesulfonyl. The sulfonylation reaction is achieved in the presence of a base, such as an amine, e.g., triethylamine, by using an appropriate sulfonyl donor, such as methanesulfonyl chloride or p-toluenesulfonyl chloride.

Step 3-3 of Scheme J-2 pertains to an intramolecular cross-coupling reaction. A carbaprostacyclin analogues analogue of Formula 4b' is prepared by an intra-molecular cyclization reaction of the compound of Formula 3b'-2 in the presence of a suitable base condition. In some embodiments, the intramolecular cyclization reaction is achieved by using a suitable base in a suitable solvent at a temperature ranging from about −70° C. to about −50° C. A suitable base includes, but is not limited to, n-butyllithium, sec-butyllithium, tert-butyllithium, and a mixture thereof. A suitable solvent includes, but is not limited to, tetrahydrofuran, ether, toluene, and a mixture thereof.

Then, as depicted in Scheme K, alumninun oxide is used to remove the TBS protective group of the primary alcohol at $C_1$ of the compound of Formula 4b', to form the compound of Formula 5b (step 1). Step 2 of Scheme K pertains to an oxidation reaction. In this reaction, the primary alcohol Formula 5b is oxidized to form the protected Iloprost of Formula 6b comprising a carbonyl acid group by using 2,2,6,6-tetramethylpiperidine-1-oxyl(TEMPO)/bis(acetoxy) iodobenzene (BAIB) oxidation conditions. Therefore, an acid or TBAF is used to remove the TBS protective group so as to form Iloprost (step 3).

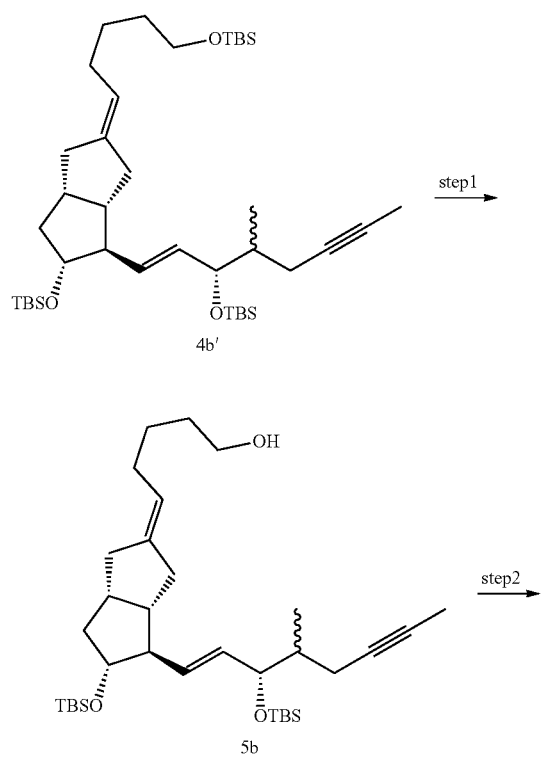

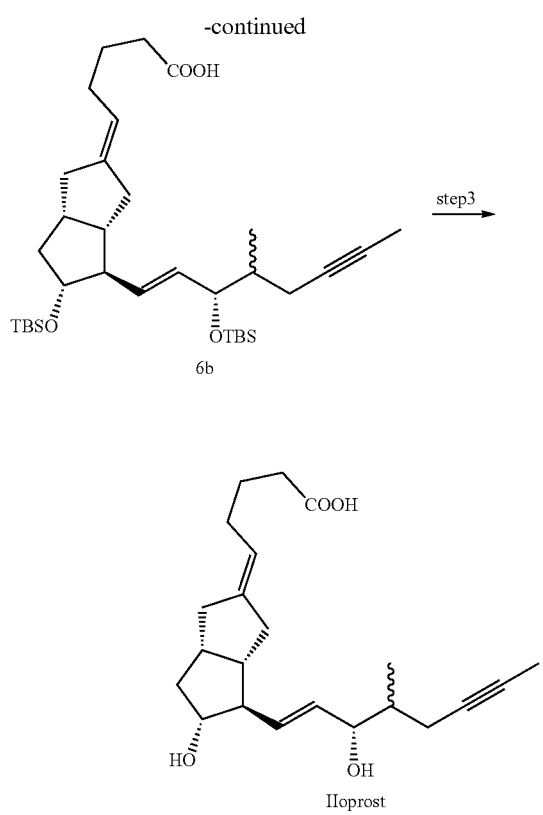

HPLC analysis shows that the geometric isomer (Z-isomer) of the obtained crude Iloprost is less than 0.5%, which meets the quality requirement of less than or equal to 0.6% as disclosed in WO 2019202345. Thus, compared to the method for synthesis of Iloprost of WO 2019202345, the process of the present invention comprises fewer steps and has higher yields, and the geometric isomer (Z-isomer) in the resultant crude Iloprost can be controlled to be less than 0.6% such that an expensive preparative HPLC method is unnecessary and thus the costs for separation and purification of Iloprost can be significantly reduced.

Synthesis of Iloprost

Scheme L depicts the synthesis of Iloprost from the compound of Formula (R)-1' (Y is —$COOR_1$ and $R_1$ is methyl in Formula (R)-1). As shown in Scheme L,

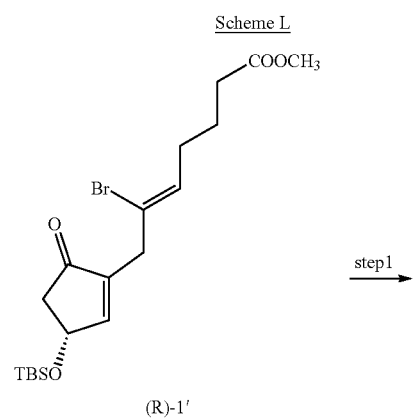

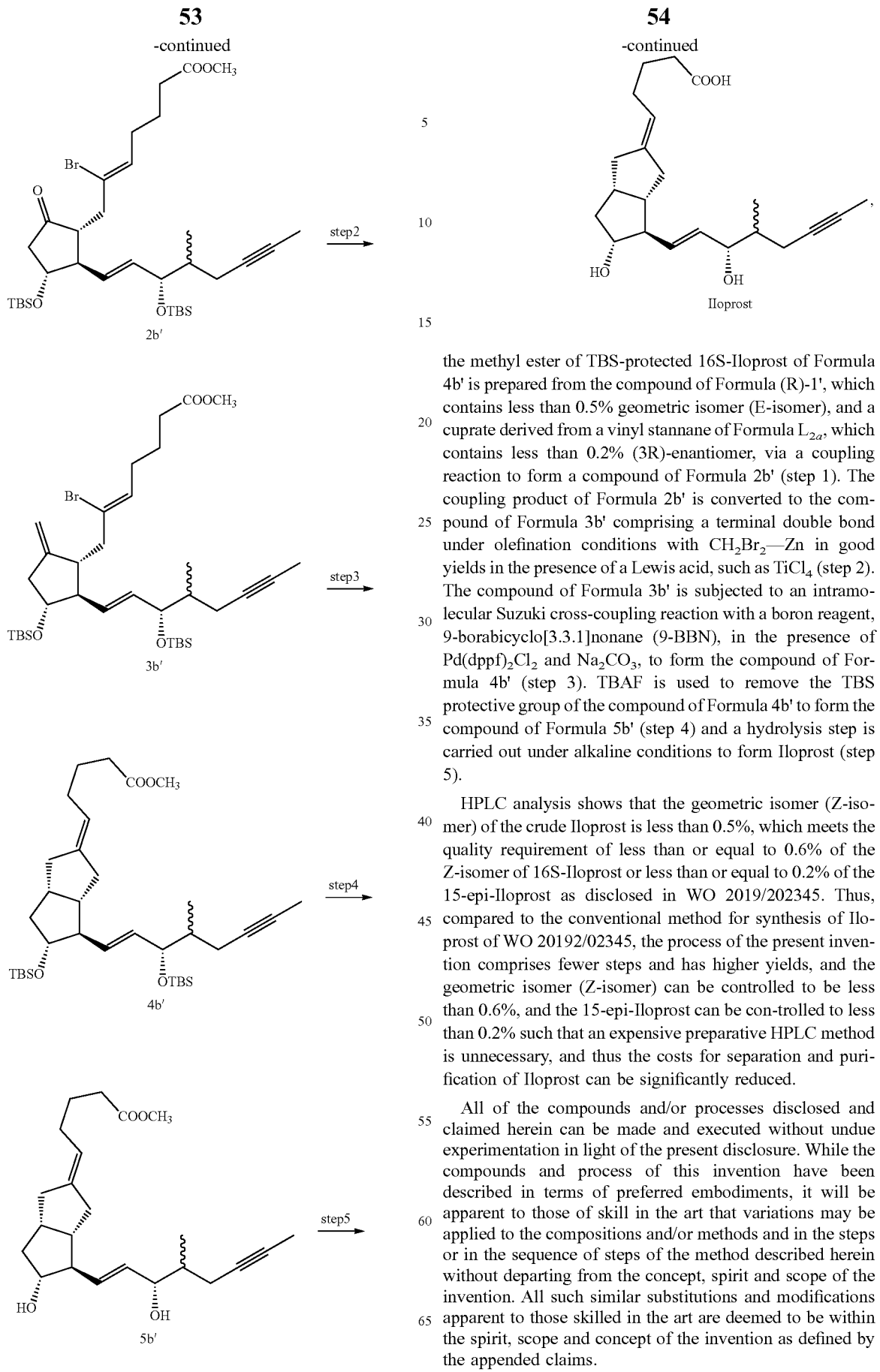

the methyl ester of TBS-protected 16S-Iloprost of Formula 4b' is prepared from the compound of Formula (R)-1', which contains less than 0.5% geometric isomer (E-isomer), and a cuprate derived from a vinyl stannane of Formula $L_{2a}$, which contains less than 0.2% (3R)-enantiomer, via a coupling reaction to form a compound of Formula 2b' (step 1). The coupling product of Formula 2b' is converted to the compound of Formula 3b' comprising a terminal double bond under olefination conditions with $CH_2Br_2$—Zn in good yields in the presence of a Lewis acid, such as $TiCl_4$ (step 2). The compound of Formula 3b' is subjected to an intramolecular Suzuki cross-coupling reaction with a boron reagent, 9-borabicyclo[3.3.1]nonane (9-BBN), in the presence of $Pd(dppf)_2Cl_2$ and $Na_2CO_3$, to form the compound of Formula 4b' (step 3). TBAF is used to remove the TBS protective group of the compound of Formula 4b' to form the compound of Formula 5b' (step 4) and a hydrolysis step is carried out under alkaline conditions to form Iloprost (step 5).

HPLC analysis shows that the geometric isomer (Z-isomer) of the crude Iloprost is less than 0.5%, which meets the quality requirement of less than or equal to 0.6% of the Z-isomer of 16S-Iloprost or less than or equal to 0.2% of the 15-epi-Iloprost as disclosed in WO 2019/202345. Thus, compared to the conventional method for synthesis of Iloprost of WO 20192/02345, the process of the present invention comprises fewer steps and has higher yields, and the geometric isomer (Z-isomer) can be controlled to be less than 0.6%, and the 15-epi-Iloprost can be con-trolled to less than 0.2% such that an expensive preparative HPLC method is unnecessary, and thus the costs for separation and purification of Iloprost can be significantly reduced.

All of the compounds and/or processes disclosed and claimed herein can be made and executed without undue experimentation in light of the present disclosure. While the compounds and process of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutions and modifications apparent to those skilled in the art are deemed to be within the spirit, scope and concept of the invention as defined by the appended claims.

EXAMPLES

Example 1

(Z)-2-bromo-7-((tert-butyldimethylsilyl)oxy)hept-2-enal (A2)

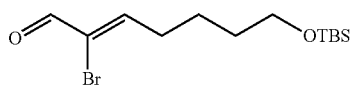 [SMILES: CC(C)(C)[Si](C)(C)OCCCC/C=C(\Br)C=O]

N-bromosuccinimide (436.1 g, 2.45 mole) were added into a mixture of (E)-7-((tert-butyldimethylsilyl)oxy)hept-2-enal (330.0 g, 1.36 mole), pyridine N-oxide (258.9 g, 2.72 mole) and acetonitrile (1.65 L). After completion of the reaction, the reaction mixture was quenched with 10% aqueous NaHCO$_3$ (1.6 L) and ethyl acetate (1.6 L), then the reaction mixture was phase separated. The organic layer was collected and dried over anhydrous Na$_2$SO$_4$. The solid was filtered off and the organic solvent was evaporated off under vacuum to give 783.2 g of the crude compound. HPLC analysis of the crude product showed 0.35% E-form isomer was found.

$^1$H-NMR (400 MHz, CDCl$_3$): δ 9.235(s, 1H), 7.189 (t, 1H, J=7.2 Hz), 3.686-3.626 (m, 2H), 2.615-2.483 (m, 2H), 1.762-1.555 (m, 4 Hz), 0.944-0.920 (m, 9H), 0.078-0.070 (m, 6H).

$^{13}$C-NMR (100 MHz, CDCl$_3$): δ 186.159, 155.784, 128.869, 62.472, 32.256, 31.823, 25.956, 25.660, 24.021, 18.336, −5.300, −5.322.

Example 2

(Z)-2-bromo-7-((tert-butyldimethylsilyl)oxy)hept-2-en-1-ol (A3)

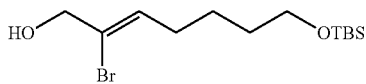 [SMILES: CC(C)(C)[Si](C)(C)OCCCC/C=C(\Br)CO]

(Z)-2-bromo-7-((tert-butyldimethylsilyl)oxy)hept-2-enal (668.3 g, crude product from Example 1) was diluted with dry THF (3.4 L), then the solution was cooled to 0° C. and following by addition of 2.0M sodium borohydride (340 mL, 0.68 mole) at 0° C. After addition, the reaction was checked by TLC. The mixture was quenched by 10% aqueous NH$_4$Cl (3 L) below the temperature of 10° C. and keep stir for 10 min at the same temperature. The reaction mixture was phase separated and the aqueous layer was extracted with ethyl acetate. The organic layers were combined and dried over anhydrous Na$_2$SO$_4$. The solid was filtered off and the organic solvent was evaporated off under vacuum. The crude product was purified by chromatography on silica gel using a mixture of hexane and ethyl acetate as a gradient eluent. Yield of the title compound was 276.8 g (63%, 2 steps start from Example 1).

$^1$H-NMR (400 MHz, CDCl$_3$): δ 5.996 (t, 1H, J=7.2 Hz), 4.242-4.228 (m, 211), 3.612 (t, 2H, J=6 Hz), 2.241-2.188 (q, 2H, J=7.6 Hz), 1.575-1.424 (m, 4H), 0.908-0.887 (m, 9H), 0.091-0.041 (m, 6H).

Example 3

(Z)-2-bromo-7-((tert-butyldimethylsilyl)oxy)hept-2-en-1-yl methanesulfonate (A4)

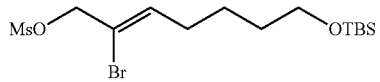 [SMILES: CC(C)(C)[Si](C)(C)OCCCC/C=C(\Br)COS(C)(=O)=O]

(Z)-2-bromo-7-((tert-butyldimethylsilyl)oxy)hept-2-en-1-ol (270 g, 835 mmole, from Example 2) was dissolved with dichloromethane (2.7 L), then the solution was cooled to 0° C. Then triethylamine (101.4 g, 1 mole) and methanesulfonyl chloride (105.2 g, 918 mmole) were added thereto at 0° C. The reaction mixture was stirred at 0° C. for 30 min. The completion of reaction was confirmed by TLC monitor. The reaction mixture was quenched with 10% aqueous NaHCO$_3$ (3 L) and the reaction mixture was phase separated. The organic layer was collected and dried over anhydrous Na$_2$SO$_4$. The solid was filtered off and the organic solvent was evaporated off under vacuum to give the 367 g of crude compound.

Example 4

(Z)-(((6-bromo-7-(2-(furan-2-yl)-1,3-dithian-2-yl)hept-5-en-1-yl)oxy)(tert-butyl) di-methylsilane (A5)

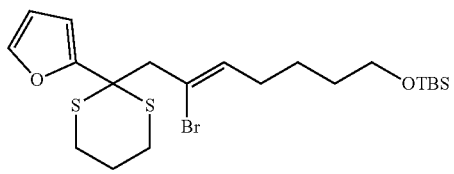 [SMILES: CC(C)(C)[Si](C)(C)OCCCC/C=C(\Br)CC1(c2ccco2)SCCCS1]

To a solution of 2-(1,3-dithian-2-yl)furan (226.4 g, 1.21 mole) in dry THF (1.13 L) was added dropwise 1.6M (658 mL, 1.05 mole) n-butyllithium in hexane at −70° C. and stirred for 30 min at the same temperature. A solution of (Z)-2-bromo-7-((tert-butyldimethylsilyl)oxy)hept-2-en-1-yl methanesulfonate (325.2 g, 810 mmole, from Example 3) and THF (813 mL) was added to the reaction flask at −70° C. Then the reaction mixture warm to 0° C. and keep stir for 1 hour at the same temperature. The completion of reaction was confirmed by TLC monitor. The reaction mixture was quenched with 10% aqueous NH$_4$Cl (3 L) and the reaction mixture was phase separated. The organic layer was collected and dried over anhydrous Na$_2$SO$_4$. The solid was filtered off and the organic solvent was evaporated off under vacuum to give the 531 g of crude compound.

$^1$H-NMR (400 MHz, CDCl$_3$): δ 7.430-7.428 (m, 1H), 6.554-6.546 (m, 1H), 6.344-6.331 (m, 1H), 5.541 (t, 1H, J=7.2 Hz), 3.581 (t, 2H, J=6 Hz), 3.230 (s, 2H), 2.911-2.840 (m, 2H), 2.728-2.674 (m, 2H), 2.109-1.876 (m, 4H), 1.521-1.452 (m, 2H), 1.392-1.335 (m, 2H), 0.942-0.855 (m, 9H), 0.049-0.005 (m, 6H).

$^{13}$C-NMR (100 MHz, CDCl$_3$): δ 152.338, 142.273, 135.253, 117.947, 112.331, 110.623, 62.889, 52.984, 51.937, 32.188, 31.398, 27.899, 25.994, 25.721, 25.083, 24.438, 18.351,−5.239.

Example 0.5

(Z)-6-bromo-7-(2-(furan-2-yl)-1,3-dithian-2-yl)hept-5-en-1-ol (A6)

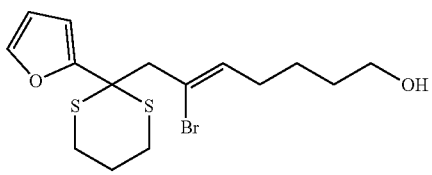 [SMILES: OCCCC/C=C(\Br)CC1(c2ccco2)SCCCS1]

(Z)-((6-bromo-7-(2-(furan-2-yl)-1,3-dithian-2-yl)hept-5-en-1-yl)oxy)(tert-butyl)dimethylsilane (531 g, crude product from Example 4) was diluted with THF (5.3 L), and 1N aqueous HCl (1.08 L) was added thereto. The reaction was stirred at room temperature and the progress of reaction was check by TLC. After the completion of reaction, the mixture was neutralized with 10% aqueous $NaHCO_3$ (5.3 L) to pH 7-8, and the reaction mixture was phase separated. The organic layer was collected and dried over anhydrous $Na_2SO_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 174.1 g (55%, 3 steps start from Example 3).

$^1$H-NMR (400 MHz, $CDCl_3$): δ 7.425 (s, 1H), 6.546-6.537 (m, 1H), 6.341-6.328 (m, 1H), 5.550 (t, 1H, J=6.8 Hz), 3.607 (t, 2H, J=6.8 Hz), 3.225 (s, 2H), 2.903-2.831 (m, 2H), 2.724-2.669 (m, 24), 2.124-2.015 (m, 4H), 1.657-1.497 (m, 2H), 1.423-1.347 (m, 2H).

Example 6

(Z)-3-bromo-1-(furan-2-yl)-8-hydroxyoct-3-en-1-one (A7)

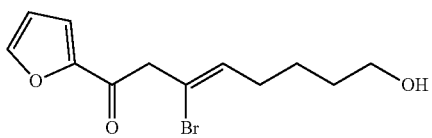 [SMILES: O=C(C/C(Br)=C/CCCCO)c1ccco1]

To a solution of (Z)-6-bromo-7-(2-(furan-2-yl)-1,3-dithian-2-yl)hept-5-en-1-ol (172.2 g, 456 mmole) in methanol (3.4 L) and water (86 mL) was added PIFA (196.2 g, 456 mmole) at room temperature. The completion of reaction was confirmed by TLC monitor. After the completion of reaction, the mixture was concentrated to remove methanol. Then the residue was extracted with ethyl acetate and 20% aqueous $Na_2S_2O_3$ (4 L), and the reaction mixture was phase separated. The organic layer was collected and extract with 10% aqueous $NaHCO_3$ (4 L). The organic layer was collected and dried over anhydrous $Na_2SO_4$. The solid was filtered off and the organic solvent was evaporated off under vacuum to give the 261.3 g of crude compound.

$^1$H-NMR (400 MHz, $CDCl_3$): δ 7.593-7.590 (s, 1H), 7.245-7.235 (m, 1H), 6.542-6.530 (n 1H), 5.865 (t, 1H, J=7.2 Hz), 3.949 (s, 2H), 3.637-3.606 (m, 2H), 2.248-2.194 (m, 2H), 1.615-1.453 (m, 4H).

$^{13}$C-NMR (100 MHz, $CDCl_3$): δ 184.459, 152.186, 146.896, 134.023, 118.251, 117.932, 112.536, 62.495, 50.168, 32.013, 31.224, 24.370.

Example 7

(Z)-3-bromo-1-(furan-2-yl)oct-3-ene-1,8-diol (A8)

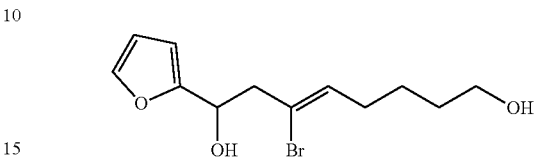

(Z)-3-bromo-1-(furan-2-yl)-8-hydroxyoct-3-en-1-one (261.3 g, crude product from Example 6) was diluted with dry THE (2.6 L), then the solution was cooled to 0° C. and following by addition of 1.0 M sodium borohydride (456 mL, 456 mmole) at 0° C. After addition, the reaction was checked by TLC. The mixture was quenched by 10% $NH_4Cl_{(aq)}$ (4 L) below the temperature of 10° C. Then the organic layer was collected and extract with 10% aqueous $NaHCO_3$ (4 L). The organic layer was collected and dried over anhydrous $Na_2SO_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 85.75 g (65%, 2 steps start from Example 6).

$^1$H-NMR (400 MHz, $CDCl_3$): δ 7.392-7.389 (s, 1H), 6.343-6.330 (m, 1H), 6.281-6.273 (m, 1H), 5.787 (t, 1H, J=7.2 Hz), 5.062-5.028 (m, 1H), 3.631 (t, 2H, J=6.4 Hz), 2.953-2.934 (m, 2H), 2.232-2.178 (m, 2H), 1.578-1.447 (m, 4H).

$^{13}$C-NMR (100 MHz, $CDCl_3$): δ 155.085, 142.175, 132.482, 123.002, 110.183, 106.623, 77.379, 65.379, 62.540, 47.717, 31.914, 31.011, 24.408.

Example 8

(Z)-5-(2-bromo-7-hydroxyhept-2-en-1-yl)-4-hydroxycyclopent-2-enone (A9)

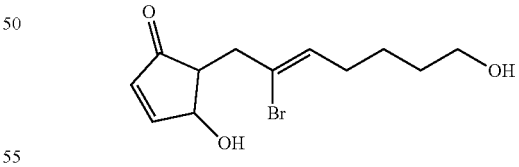

The 1.0 mM K2HPO4 (1.7 L, 1.7 mmole) was added to a solution of (Z)-3-bromo-1-(furan-2-yl)oct-3-ene-1,8-diol (83.3 g, 288 mmole, from Example 7) in the mixture of THF (125 mL), and the reaction heat to reflux and keep stir. The completion of reaction was confirmed by TLC monitor. After the completion of reaction, the mixture was extracted by ethyl acetate (2 L), and the reaction mixture was phase separated. The organic layers were collected and dried over anhydrous $Na_2SO_4$. The solid was filtered off and the organic solvent was evaporated off under vacuum to give 81.2 g of the crude title compound.

Example 9

(Z)-2-(2-bromo-7-hydroxyhept-2-en-1-yl)-4-hydroxycyclopent-2-enone (1a)

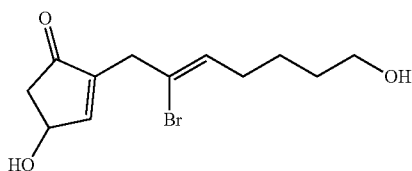 [SMILES: O=C1CC(O)C=C1C/C(Br)=C/CCCCO]

To a solution of crude (Z)-5-(2-bromo-7-hydroxyhept-2-en-1-yl)-4-hydroxycyclopent-2-enone (81.2 g, crude product from Example 8) in THF (810 mL) was added triethylamine (28.4 g, 280 mole) and chloral hydrate (4.65 g, 28.1 mmol) at room temperature. The completion of reaction was confirmed by TLC monitor. The mixture was washed by 10% aqueous $NH_4Cl$ (800 ML) and dried over anhydrous $Na_2SO_4$. The solid was filtered off and the organic solvent was evaporated off under vacuum. The crude product was purified by chromatography on silica gel using a mixture of hexane and ethyl acetate as a gradient eluent. Yield of the title compound was 42.1 g (51%, 2 steps).

$^1$H-NMR (400 MHz, $CDCl_3$): δ 7.332-7.277 (m, 1H), 5.824 (t, 1H, J=7.2 Hz), 4.981-4.967 (m, 1H), 3.641 (t, 2H, J=6 Hz), 3.335 (s, 2K), 2.871-2.809 (m, 1H), 2.366-2.315 (m, 1H), 2.234-2.181 (m, 2H), 1.608-1.469 (m, 4H).

$^{13}$C-NMR (100 MHz, $CDCl_3$): δ 205.445, 158.478, 143.753, 131.791, 122.501, 77.379, 68.377, 62.570, 44.688, 36.757, 31.967, 31.049, 24.431.

Example 9-1

(Z)-2-(2-bromo-7-(tert-butyldimethylsilyl)oxy)hept-2-en-1-yl)-4-hydroxycyclopent-2-enone (1b, Scheme A, Step 10)

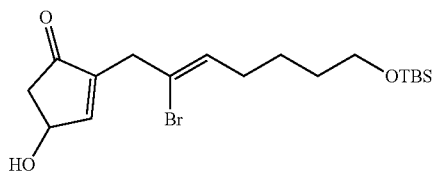

(Z)-2-(2-bromo-7-((tert-butyldimethylsilyl)oxy)hept-2-en-1-yl)-4-hydroxy cyclopent-2-enone (54.3 g, 188 mmol, from Example 12) was dissolved in ethyl acetate (540 mL). Then imidazole (28.12 g, 411 mmol) and tert-butyldimethylsilyl chloride (28.25 g, 188 mmol) were added thereto. The reaction mixture was stirred at room temperature. The completion of reaction was confirmed by TLC monitor. The reaction mixture was quenched with 10% aqueous $NaHCO_3$ (600 mL) and the reaction mixture was phase separated. The organic layer was collected and dried over anhydrous $Na_2SO_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 42.8 g (56%).

$^1$H-NMR (400 MHz, $CDCl_3$): δ 7.313-7.305 (m, 1H), 5.833-5.798 (m, 1H), 4.984 (m, 1H), 3.626-3.597 (m, 2H), 3.329 (m, 2H), 2.872-2.810 (m, 1H), 2.360-2.308 (m, 1H), 2.206-2.170 (m, 2H), 1.552-1.433 (m, 4H), 0.918-0.886 (m, 9H), 0.053--0.010 (m, 6H)

Example 9-2

(R,Z)-3-(2-bromo-7-((tert-butyldimethylsilyl)oxy) hept-2-en-1-yl)-4-oxocyclopent-2-en-1-yl acetate ((R)-1c), and (S,Z)-2-(2-bromo-7-((tert-butyldimethylsilyl)oxy)hept-2-en-1-yl)-4-hydroxycyclopent-2-enone ((S)-1b) ((S)-1b and (R)-1c, Scheme C, Step 1)

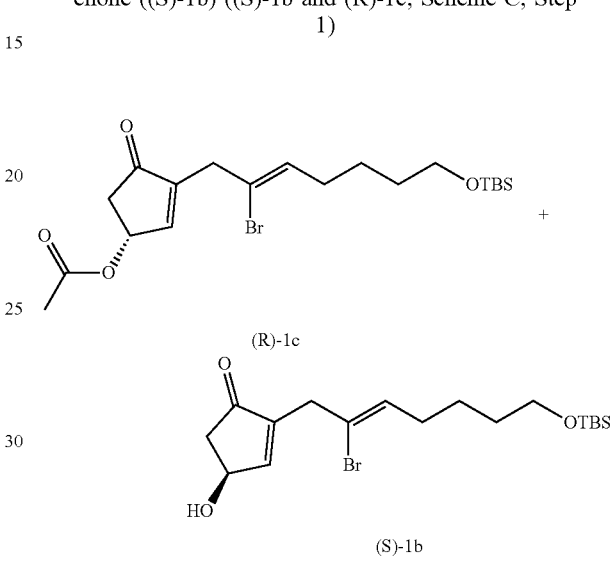

(Z)-2-(2-bromo-7-((tert-butyldimethylsilyl)oxy)hept-2-en-1-yl)-4-hydroxy cyclopent-2-enone (42.8 g, 106 mmole, from Example 9-1) was dissolved with hexane (430 mL), then vinyl acetate (43 mL) and lipase SL (2.1 g, 5% w.t.) were added thereto. And the reaction mixture was stirred at room temperature. The completion of reaction was confirmed by HPLC analysis that reaction conversion close to 50%. The conversion rate is larger than 50±3%. Then filter the reaction mixture and collect the filtrate. Subject the filtrate to concentrate to obtain the 45.21 g of crude mixture compound.

Example 9-3

(R,Z)-3-(2-bromo-7-((tert-butyldimethylsilyl)oxy) hept-2-en-1-yl)-4-oxocyclopent-2-en-1-yl acetate ((R)-1c, Scheme C, Step 2)

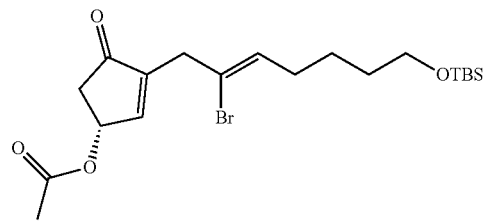 [SMILES: CC(=O)O[C@H]1C=C(C/C(Br)=C/CCCCO[Si](C)(C)C(C)(C)C)C(=O)C1]

A mixture of (R,Z)-3-(2-bromo-7-((tert-butyldimethylsilyl)oxy)hept-2-en-1-yl)-4-oxocyclopent-2-en-1-yl acetate ((R)-1c) and (S,Z)-2-(2-bromo-7-((tert-butyldimethylsilyl)oxy)hept-2-en-1-yl)-4-hydroxycyclopent-2-enone ((S)-1b) (45.21 g, crude product from Example 9-2) was dissolved with toluene (450 mL). And triphenylphosphine (14.7 g, 56 mmole) was added thereto and keep stir until the triphenylphosphine solid was dissolved in toluene then cool to −10° C. and keep stir at the same temperature. And acetic acid (3.36 g, 56 mmole) and diisopropyl azodicarboxylate (11.3 g, 56 mmole) were added thereto. And the reaction mixture was stirred at −10° C. The completion of reaction was confirmed by TLC. Then the reaction mixture was concentrated and the crude product was purified by chromatography on silica gel by using a mixture of hexane and ethyl acetate as a gradient eluent. Yield of the title compound was 42.27 g (89.5%, 2 steps). HPLC analysis of the product showed that 0.63% enantiomer was found.

$^1$H-NMR (400 MHz, CDCl$_3$): δ 7.305-7.298 (m, 1H), 5.835-5.800 (m, 2H), 3.607 (t, 2H, J=6.4 Hz), 3.346-3.344 (m, 2H), 2.908-2.846 (m, 1H), 2.396-2.344 (m, 1H), 2.184-2.166 (m, 2H), 2.082 (s, 3H), 1.529-1.453 (m, 4H), 0.892-0.878 (m, 9H), 0.046-0.032 (m, 6H).

Example 9-4

(R,Z)-2-(2-bromo-7-((tert-butyldimethylsilyl)oxy)hept-2-en-1-yl)-4-hydroxycyclopent-2-enone ((R)-1b, Scheme C, Step 3)

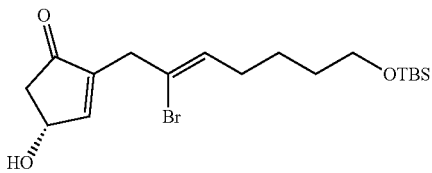 [SMILES: CC(C)(C)[Si](C)(C)OCCCC/C=C(\Br)CC1=C[C@H](O)CC1=O]

(R,Z)-3-(2-bromo-7-((tert-butyldimethylsilyl)oxy)hept-2-en-1-yl)-4-oxocy clopent-2-en-1-yl acetate (42.27 g, from Example 9-3) was dissolved in acetone (20 mL) and phosphate buffer (420 mL) and the pH value was adjusted to pH 8.5 by the addition of 3M aqueous NaOH solution. The Lipase SL (4.2 g, 10% w.t.) were added thereto and the reaction mixture was stirred & room temperature. The completion of reaction was checked by HPLC analysis that the enantiomeric excess of title compound is greater than 99.0%. Then the lipase resin was removed during filtration. Then the filtrate was collected and concentrated, the crude product was purified by chromatography on silica gel by using a mixture of hexane and ethyl acetate as a gradient eluent. Yield of the title compound was 37.09 g (96.8%). HPLC analysis of the product showed that 0.28% enantiomer was found.

$^1$H-NMR (400 MHz, CDCl$_3$): δ 7.309 (m, 1H), 5.815 (t, 1H, J=6.4 Hz), 4.988 (m, 1H), 3.610 (t, 2H, J=6.4 Hz), 3.326 (m, 2H), 2.874-2.812 (m, 1H), 2.362-2.357 (m, 1H), 2.315-2.150 (m, 2H), 2.072-2.057 (m, 1H), 1.550-1.429 (m, 4H), 0.888 (m, 9H), 0.044-−0.009 (m, 6H).

$^{13}$C-NMR (100 MHz, CDCl$_3$): δ 204.917, 157.728, 144.088, 132.126, 122.092, 77.324, 68.557, 62.872, 44.693, 36.708, 32.260, 31.971, 31.167, 25.967, 25.353, 24.431, 18.354,−5.275.

Example 10

(R,Z)-3-(7-acetoxy-2-bromohept-2-en-1-yl)-4-oxocyclopent-2-en-1-yl acetate ((R)-1b), and (S,Z)-6-bromo-7-(3-hydroxy-5-oxocyclopent-1-en-1-yl)hept-5-en-1-yl acetate ((S)-1C) (from 1a to (R)-1b and (S)-1c)

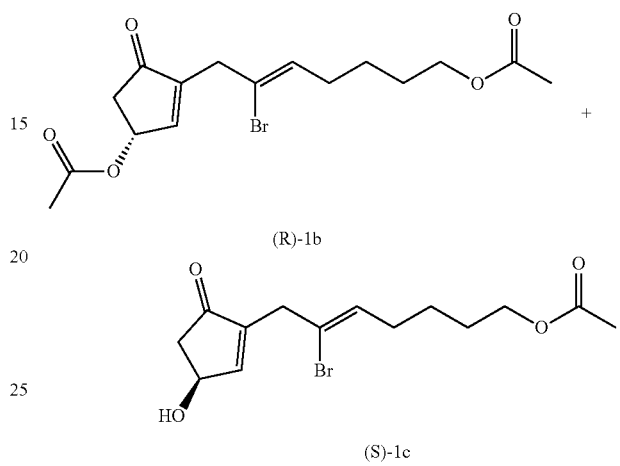

(Z)-2-(2-bromo-7-hydroxyhept-2-en-1-yl)-4-hydroxycyclopent-2-enone (42.1 g, 145.6 mmole, from Example 9) was dissolved with Methyl isobutyl ketone (420 mL), then vinyl acetate (41.3 g, 479 mmole) and lipase SL (2.11 g, 5% w.t.) were added thereto. And the reaction mixture was stirred at room temperature. The completion of reaction was confirmed by HPLC that reaction conversion close to 50%. The conversion rate is larger than 50±3%. Then filter the reaction mixture and collect the filtrate. Subject the filtrate to concentrate to obtain the 55.1 g of crude mixture compound.

Example 11

(R,Z)-3-(7-acetoxy-2-bromohept-2-en-1-yl)-4-oxocyclopent-2-en-1-yl acetate ((R)-1b and (S)-1c to (R)-1d)

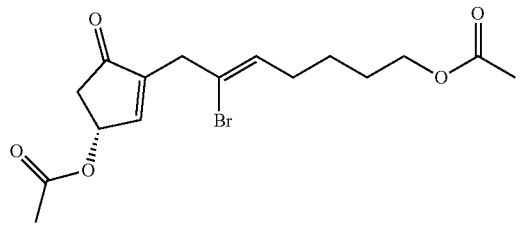 [SMILES: CC(=O)OCCCC/C=C(\Br)CC1=C[C@H](OC(C)=O)CC1=O]

A mixture of (R,Z)-3-(7-acetoxy-2-bromohept-2-en-1-yl)-4-oxocyclopent-2-en-1-yl acetate ((R)-1b) and (S,Z)-6-bromo-7-(3-hydroxy-5-oxocyclopent-1-en-1-yl)hept-5-en-1-yl acetate((S)-1c) (55.1 g, crude product from Example 10) was dissolved with toluene (551 mL). Then triphenylphosphine (21.82 g, 83 mmole), acetic acid (5.0 g, 83 mmole) and diisopropyl azodicarboxylate (16.82 g, 83 mmole) were added thereto. And the reaction mixture was stirred at room temperature. The completion of reaction was confinned by TLC. Then the reaction mixture was concentrated and the crude product was purified by chromatography on silica gel by using a mixture of hexane and ethyl acetate as a gradient eluent. Yield of the title compound was 43.5 g (80%, 2 steps). HPLC analysis of the product showed that no enantiomer was found.

$^1$H-NMR (400 MHz, CDCl$_3$): δ 7.311-7.305 (m, 1H), 5.829-5.774 (m, 2H), 4.056 (t, 2H, J=6.8 Hz), 3.348-3.343 (m, 2H), 2.912-2.850 (m, 1H), 2.402-2.350 (m, 1H), 2.215-2.161 (m, 2H), 2.085 (s, 3H), 2.038 (s, 3H), 1.668-1.606 (m, 2H), 1.504-1.428 (m, 2H).

Example 12

(R,Z)-2-(2-bromo-7-hydroxyhept-2-en-1-yl)-4-hydroxycyclopent-2-enone ((R)-1d to (R)-1e)

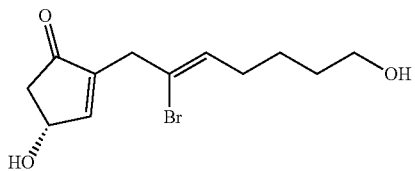

(R,Z)-3-(7-acetoxy-2-bromohept-2-en-1-yl)-4-oxocyclopent-2-en-1-yl acetate (11.2 g, from Example 11) was dissolved in acetone (11 mL) and phosphate buffer (112 mL) and the pH value was adjusted to pH 8.5 by the addition of 1N aqueous NaOH solution. The Novozym 435 (5.6 g, 50% w.t.) were added thereto and the reaction mixture was stirred at room temperature. The completion of reaction was checked by HPLC analysis, and the lipase resin was removed during filtration. Then the filtrate was collected and concentrated, the crude product was purified by chromatography on silica gel by using a mixture of hexane and ethyl acetate as a gradient eluent. Yield of the title compound was 6.16 g (71%).

$^1$H-NMR (400 MHz, CDCl$_3$): δ 7.334-7.329 (m, 1H), 5.813 (t, 1H, J=7.2 Hz), 4.966-4.950 (m, 1H), 3.624 (t, 2H, J=6.4 Hz), 3.323 (s, 2H), 2.857-2.796 (n 1H), 2.354-2.303 (m, 1H), 2.224-2.170 (m, 2H), 1.612-1.437 (m, 4H).

$^{13}$C-NMR (100 MHz, CDCl$_3$): δ 205.680, 158.759, 143.647, 131.769, 122.516, 68.286, 62.502, 44.673, 36.757, 31.929, 31.041, 24.431.

Example 13

(R,Z)-2-(2-bromo-7-((tert-butyldimethylsilyl)oxy)hept-2-en-1-yl)-4-((tert-butyldimethylsilyl)oxy)cyclopent-2-enone ((R)-1e to (R)-1f)

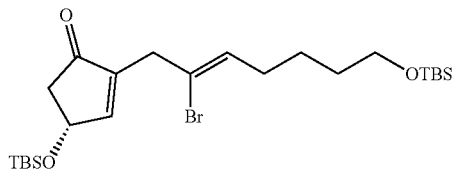 [SMILES: CC(C)(C)[Si](C)(C)OCCCC/C=C(\Br)CC1=C[C@H](O[Si](C)(C)C(C)(C)C)CC1=O]

(R,Z)-2-(2-bromo-7-hydroxyhept-2-en-1-yl)-4-hydroxycyclopent-2-enone (2.76 g, 9.5 mmol, from Example 12) was dissolved in ethyl acetate (28 mL). Then imidazole (3.9 g, 57 mmol) and tert-butyldimethylsilyl chloride (4.32 g, 28.7 mmol) were added thereto. The reaction mixture was stirred at room temperature. The completion of reaction was confirmed by TLC monitor. The reaction mixture was quenched with 10% aqueous NaHCO$_3$ (30 mL) and the reaction mixture was phase separated. The organic layer was collected and dried over anhydrous Na$_2$SO$_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 4.1 g (83%).

$^1$H-NMR (400 MHz, CDCl$_3$): δ 7.191-7.188 (m, 1H), 5.798 (t, 1H, J=6.8 Hz), 4.932-4.918 (m, 1H), 3.610 (t, 2H, J=6.4 Hz), 3.378-3.251 (q, 2H, 16.4 Hz), 2.795-2.734 (dd, 1H, J=6, 18.4 Hz), 2.317-2.266 (dd, 1H, J=2, 18.4 Hz), 2.206-2.152 (q, 2H, 7.6 Hz), 1.597-1.430 (m, 4H), 0.906-0.889 (m, 18H), 0.129-0.036 (m, 12H).

Example 14

(R,Z)-3-(2-bromo-7-hydroxyhept-2-en-1-yl)-4-oxocyclopent-2-en-1-yl acetate ((R)-1d to (R)-1g)

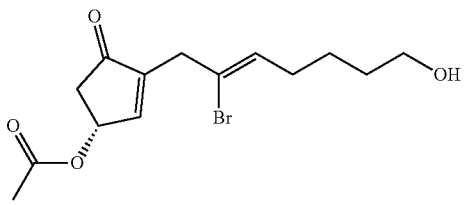 [SMILES: CC(=O)O[C@H]1C=C(C/C(Br)=C/CCCCO)C(=O)C1]

(R,Z)-3-(7-acetoxy-2-bromohept-2-en-1-yl)-4-oxocyclopent-2-en-1-yl acetate (54.1 g, crude product from Example 11) was dissolved in methyl tert-butyl ether (541 mL) and methanol (54 mL). The Novozym 435 (5.6 g, 50% w.t.) were added thereto and the reaction mixture was stirred at room temperature. The completion of reaction was checked by HPLC analysis, and the lipase resin was removed during filtration. Then the filtrate was collected and concentrated, the crude product was purified by chromatography on silica gel by using a mixture of hexane and ethyl acetate as a gradient eluent. Yield of the title compound was 27.5 g (57%).

$^1$H-NMR (400 MHz, CDCl$_3$): δ 7.314-7.309 (m, 1H), 5.823 (t, 1H, J=7.2 Hz), 5.782-5.766 (m, 1H), 3.643 (t, 2H, J=6.4 Hz), 3.343 (m, 2H), 2.909-2.847 (dd, 1H, J=6, 18.8 Hz), 2.403-2.351 (dd, 1H, J=2, 18.8 Hz), 2.218-2.164 (q, 2H), 2.085 (s, 3H), 1.602-1.462 (m, 4H).

Example 15

(R,Z)-7-(3-acetoxy-5-oxocyclopent-1-en-1-yl)-6-bromohept-5-enoic acid ((R)-1g to (R)-1h)

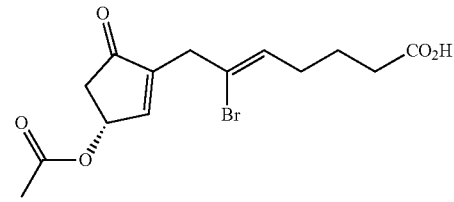 [SMILES: CC(=O)O[C@H]1C=C(C/C(Br)=C/CCCC(=O)O)C(=O)C1]

To a solution of (R,Z)-3-(2-bromo-7-hydroxyhept-2-en-1-yl)-4-oxocyclopent-2-en-1-yl acetate (27.2 g, crude product from Example 14) in a mixture of acetonitrile and water (544 mL, v/v=1/1) was added diacetoxy iodobenzene (88.26 g, 274 mmole) and 2,2,6,6-tetramethylpiperidine-1-oxyl (3.89 g, 24.9 mmole), then the reaction mixture was stirred at room temperature. The completion of reaction was confirmed by TLC monitor. The reaction mixture was quenched with 1M aqueous $Na_2S_2O_3$ (600 mL) and the reaction mixture was phase separated. The organic layer was collected and dried over anhydrous $Na_2SO_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 28 g (98%).

$^1$H-NMR (400 MHz, $CDCl_3$): δ 7.320-7.315 (m, 1H), 5.834-5.777 (m, 2H), 3.354 (m, 2H), 2.919-2.856 (dd, 1H, J=6.4, 18.8 Hz), 2.410-2.357 (m, 3H), 2.260-2.206 (m, 2H), 2.092 (s, 3H), 1.795-1.739 (m, 2H).

Example 16

(R,Z)-methyl 6-bromo-7-(3-hydroxy-5-oxocyclopent-1-en-1-yl)hept-5-enoate ((R)-1h to (R)-1i)

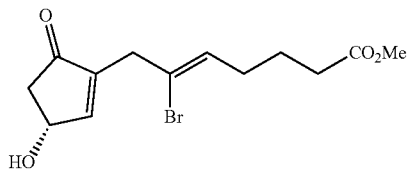 [SMILES: COC(=O)CCC/C=C(\Br)CC1=C[C@H](O)CC1=O]

(R,Z)-7-(3-acetoxy-5-oxocyclopent-1-en-1-yl)-6-bromohept-5-enoic acid (27.1 g, 78.5 mmole, from Example 15) was dissolved in methanol (220 mL), then the solution was cooled to 0° C. Then diluted sulfuric acid (27.1 g) in methanol (55 mL) was added thereto. The reaction mixture warm to room temperature and keep stir for 2 hours at the same temperature. The completion of reaction was confirmed by TLC monitor. The ice water (200 mL) was added slowly for quench reaction, followed by 10% aqueous $NaHCO_3$ (450 mL). Methanol was removed from reaction mixture un-der reduced pressure, then ethyl acetate (600 mL) was added into mixture for extraction. The reaction mixture was phase separated. The organic layer was collected and dried over anhydrous $Na_2SO_4$. The solid was filtered off and the organic solvent was evaporated off under vacuum to give crude compound. The crude product was purified by chromatography on silica gel using a mixture of hexane and ethyl acetate as a gradient eluent. Yield of the title compound was 20.75 g (82%). HPLC analysis of the product showed that 0.71% enantiomer was found.

$^1$H-NMR (400 MHz, $CDCl_3$): δ 7.330-7.325 (m, 1H), 5.799 (t, 1H, J=7.2 Hz), 4.982 (m, 1H), 3.669 (s, 3H), 3.327 (s, 2H), 2.866-2.760 (m, 3H), 2.366-2.314 (i, 3H), 2.234-2.179 (m, 2H), 1.778-1.722 (m, 2H).

$^{13}$C-NMR (100 MHz, $CDCl_3$): 205.286, 173.977, 158.372, 143.624, 130.805, 123.237, 68.430, 51.694, 44.666, 36.711, 33.318, 30.730, 23.520.

Example 17

(R,Z)-methyl 6-bromo-7-(3-((tert-butyldimethylsilyl)oxy)-5-oxocyclopent-1-en-1-yl)hept-5-enoate ((R)-1i to (R)-1j)

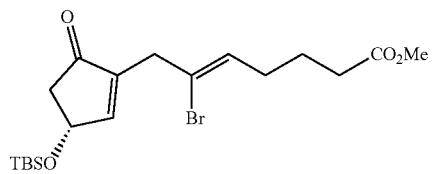 [SMILES: COC(=O)CCC/C=C(\Br)CC1=C[C@H](O[Si](C)(C)C(C)(C)C)CC1=O]

(R,Z)-methyl 6-bromo-7-(3-hydroxy-5-oxocyclopent-1-en-1-yl)hept-5-enoate (20.0 g, 63 mmol, from Example 16) was dissolved in ethyl acetate (200 mL). Then imidazole (12.88 g, 189 mmol) and tert-butyldimethylsilyl chloride (19.0 g, 126 mmol) were added thereto. The reaction mixture was stirred at room temperature. The completion of reaction was confirmed by TLC monitor. The reaction mixture was quenched with 10% aqueous $NaHCO_3$ (300 mL) and the reaction mixture was phase separated. The organic layer was collected and dried over anhydrous $Na_2SO_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 26.02 g (95%). GC analysis of the product showed that 0.43% E-isomer was found.

$^1$H-NMR (400 MHz, $CDCl_3$): δ 7.220-7.211 (m, 1H), 5.804 (t, 1H, J=6.8 Hz), 4.953-4.937 (m, 1H), 3.683 (s, 3H), 3.400-3.275 (m, 2H), 2.811-2.751 (m, 1H), 2.366-2.203 (m, 4H), 1.798-1.724 (m, 2H), 0.930-0.906 (m, 9H), 0.155-0.082 (m, 6H).

$^{13}$C-NMR (100 MHz, $CDCl_3$): 205.035, 173.749, 158.888, 142.850, 130.645, 123.420, 68.976, 51.557, 45.318, 36.749, 33.296, 30.753, 25.789, 23.565, 18.123,-4.639.

Example 18

(Z)-methyl 6-bromo-7-((1R,2R,3R)-3-((tert-butyldimethylsilyl)oxy)-2-((3S,4S,E)-3-((tert-butyldi methylsilyl)oxy)-4-methyloct-1-en-6-yn-1-yl)-5-oxocyclopentyl)hept-5-enoate ((R)-1j to 2a)

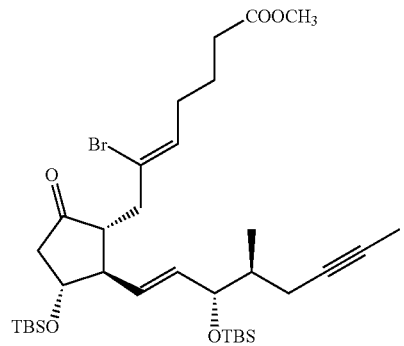 [SMILES: CC#CC[C@H](C)[C@@H](/C=C/[C@H]1[C@H](O[Si](C)(C)C(C)(C)C)CC(=O)[C@@H]1C/C(Br)=C/CCCC(=O)OC)O[Si](C)(C)C(C)(C)C]

To a solution of thiophene (640 mg, 7.62 mmole) in dry THF (6.4 mL) was added dropwise 1.6M (4.4 mL, 6.93 mmole) n-butyllithium in hexane at −20° C. and the reaction mixture was stirred for 1 hour at −20° C. After 1 hour, the solution was transferred into slurry of CuCN (2.9 g, 7.62 mmole) and dry THF (29 mL) at −40° C. via cannula then the reaction mixture was stirred for 1 hour at −40° C. to obtain 2-thienyl(cyano)copper lithium solution.

To a solution of tert-butyldimethyl(((3S,4S,E)-4-methyl-1-(tributylstannyl)oct-1-en-6-yn-3-yl)oxy)sila ne (3.77 g, 6.96 mmol) in dry tetrahydrofluan (37.7 mL) was added dropwise 1.6M (4.4 mL, 6.93 mmole) n-butyllithium in n-hexane at −70° C. and was stirred for 30 minutes at the same temperature. The 2-thienyl(cyano)copper lithium solution was cooled down to −70° C. and added to the reaction flask. After 1 hr, a solution of (R,Z)-methyl 6-bromo-7-(3-((tert-butyldimethylsilyl)oxy)-5-oxocyclopent-1-en-1-yl)hept-5-enoate (1.0 g, 2.32 mmol, from Example 17) in 10 ml THF at −70° C. was added thereto. The completion of reaction was confirmed by TLC monitor, then the reaction mixture was quenched with saturated aqueous ammonium chloride (67.5 mL) containing ammonium hydroxide (7.5 mL). The reaction mixture was phase separated and the aqueous layer was extracted with ethyl acetate. The organic layers were combined and dried over anhydrous $Na_2SO_4$. The solid was filtered off and the organic solvent was evaporated under vacuum to give the crude title compound. The crude product was purified by chromatography on silica gel using a mixture of hexane and ethyl acetate as a gradient eluent. Yield of the title compound was 1.32 g (83%).

$^1$H-NMR (400 MHz, $CDCl_3$): δ 5.695 (t, 1H. J=6.8 Hz), 5.534-5.502 (m, 2H), 4.157-4.143 (m, 1H), 4.013-3.985 (m, 1H), 3.670 (s, 3H), 2.784-2.145 (m, 13H), 1.784-1.613 (m, 5H), 0.910-0.860 (m, 21H), 0.068-0.005 (m, 12H)

$^{13}$C-NMR (100 MHz, $CDCl_3$): 216.117, 173.787, 133.545, 130.425, 130.182, 128.452, 128.323, 126.418, 77.750, 77.219, 76.528, 75.747, 73.758, 51.853, 51.550, 50.988, 47.360, 41.576, 39.565, 33.288, 30.662, 25.880, 25.766, 25.744, 23.672, 22.017, 18.154, 17.971, 15.383, 3.474, −3.987, −4.700, −4.738, −4.852.

Example 19

(Z)-methyl 6-bromo-7-((1R,2R,3R)-3-((tert-butyldimethylsilyl)oxy)-2-((3S,4S,E)-3-((tert-butyldi methylsilyl)oxy)-4-methyloct-1-en-6-yn-1-yl)-5-methylenecyclopentyl)hept-5-enoate (2a to 3a)

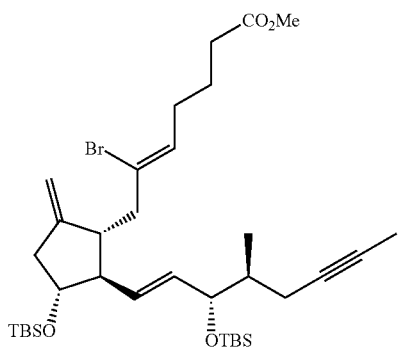 [SMILES: C=C1C[C@@H](O[Si](C)(C)C(C)(C)C)[C@H](/C=C/[C@@H](O[Si](C)(C)C(C)(C)C)[C@@H](C)CC#CC)[C@H]1C/C(Br)=C/CCCC(=O)OC]

To a slurry of activated zinc powder (330 mg, 5.04 mmole), dibromo-methane (292 mg, 1.68 mmole) and dry THF (15 mL) was added titanium tetrachloride (224 mg, 1.18 mmole) at −40° C., then the temperature of reaction mixture was warm to 5° C. and keep stir for 3 days at the same temperature. After 3 days, (Z)-methyl 6-bromo-7-((1R,2R,3R)-3-((tert-butyldimethylsilyl)oxy)-2-((3S,4S,E)-3-((tert-butyldi methylsilyl)oxy)-4-methyloct-1-en-6-yn-1-yl)-5-oxocyclopentyl)hept-5-enoate (1.15 g, 1.68 mmole, from Example 18) in dry THF (12 mL) were added thereto. And the reaction mixture was stirred at room temperature. The completion of reaction was confirmed by TLC monitor. The reaction mixture was quenched with 10% aqueous Na—$HCO_3$ (200 mL) and the reaction mixture was phase separated. The organic layer was collected and dried over anhydrous $Na_2SO_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 0.53 g (46%).

$^1$H-NMR (400 MHz, $CDCl_3$): δ 5.644 (t, 1H. J=7.2 Hz), 5.448-5.417 (m, 2H), 4.910-4.830 (m, 2H), 3.970-3.902 (m, 2H), 3.666 (s, 3H), 2.643-2.062 (m, 12H), 1.779-1.629 (m, 6H), 0.912-0.862 (m, 21H), 0.070-0.006 (m, 12H)

$^{13}$C-NMR (100 MHz, $CDCl_3$): 173.833, 151.047, 132.505, 131.966, 129.014, 128.551, 108.103, 78.009, 76.308, 76.043, 55.755, 51.519, 46.859, 44.954, 42.631, 39.649, 33.394, 30.654, 25.903, 25.865, 23.725, 22.032, 18.154, 18.032, 15.421, 3.474, 1.008, −3.926, 4.601, −4.662, −4.890.

Example 20

(E)-methyl 5-((3aS,4R,5R,6aS)-5-((tert-butyldimethylsilyl)oxy)-4-((3S,4S,E)-3-((tert-butyldimeth ylsilyl)oxy)-4-methyloct-1-en-6-yn-1-yl)hexahydropentalen-2(1H)-ylidene) Pentanoate (3a to 4a)

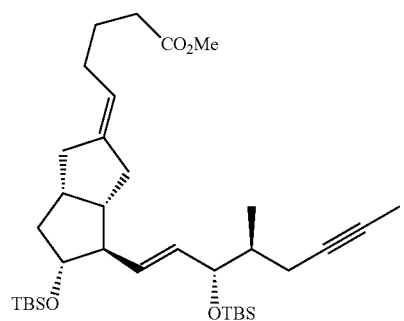 [SMILES: CC#CC[C@H](C)[C@@H](/C=C/[C@@H]1[C@H]2C/C(=C/CCCC(=O)OC)C[C@H]2C[C@H]1O[Si](C)(C)C(C)(C)C)O[Si](C)(C)C(C)(C)C]

The 9-BBN in THF (0.5M, 4.38 mL, 2.19 mmole) was added to a solution of (Z)-methyl 6-bromo-7-((1R,2R,3R)-3-((tert-butyldimethylsilyl)oxy)-2-((3S,4S,E)-3-((tert-butyldi methylsilyl)oxy)-4-methyloct-1-en-6-yn-1-yl)-5-methylenecyclopentyl)hept-5-enoate (500 mg, 0.73 mmol, from Example 19) in dry THF at 0° C. and keep stir for 2 hours at the same temperature. After 2 hours, Pd(dppf)Cl2 (54 mg, 0.073 mmole) and 1M aqueous $Na_2CO_3$ solution (2.2 mL, 2.2 mmole) were added thereto and the reaction mixture was stirred at 60° C. for 1 hour. The completion of reaction was confirmed by TLC monitor. The reaction mixture was extracted with water (25 mL) and ethyl acetate (25 mL), and the reaction mixture was phase separated. The organic layer was collected and dried over anhydrous Na₂SO₄. The solid was filtered off and the organic solvent was evaporated off under vacuum to give the crude compound. The crude product was purified by chromatography on silica gel using a mixture of hexane and ethyl acetate as a gradient eluent. Yield of the title compound was 209 mg (47%).

¹H-NMR (400 MHz, CDCl₃): δ 5.532-5.357 (m, 2H), 5.207-5.172 (m, 1H), 3.974-3.943 (m, 1H), 3.768-3.706 (m, 1H), 3.661 (s, 3H), 2.374-1.156 (m, 21H), 0.916-0.862 (m, 21H), 0.064--0.000 (m, 12H)

¹³C-NMR (100 MHz, CDCl₃): 174.280, 143.131, 132.717, 131.632, 120.384, 78.312, 78.122, 77.325, 76.202, 56.051, 51.443, 44.445, 42.571, 39.816, 38.252, 37.698, 35.998, 33.501, 28.780, 25.911, 25.076, 22.062, 18.169, 18.100, 15.436, 3.474, 1.008, -3.933, -4.450, 4.601, -4.950.

Example 21

(E)-methyl 5-((3aS,4R,5R,6aS)-5-hydroxy-4-((3S,4S,E)-3-hydroxy-4-methyloct-1-en-6-yn-1-yl)hexahydropentalen-2(1H)-ylidene)pentanoate (from 4a to 16(S)-iloprost methyl ester)

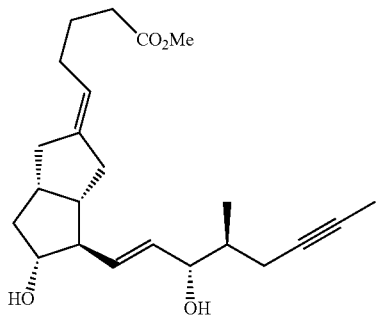 [SMILES: CC#CC[C@H](C)[C@H](O)/C=C/[C@@H]1[C@H]2C/C(=C/CCCC(=O)OC)C[C@H]2C[C@H]1O]

(Z)-methyl 6-bromo-7-((1R,2R,3R)-3-((tert-butyldimethylsilyl)oxy)-2-((3S,4S,E)-3-((tert-butyldi methylsilyl)oxy)-4-methyloct-1-en-6-yn-1-yl)-5-methylenecyclopentyl)hept-5-enoate (183 mg, 0.303 mmole, from Example 20) was diluted with THF (1.8 mL), and 1M TBAF (1.8 mL, 1.818 mmole) was added thereto. The reaction was stirred at room temperature and the progress of reaction was check by TLC. After the completion of reaction, the mixture was neutralized with 10% aqueous NaHCO₃ (5 mL), and the reaction mixture was phase separated. The organic layer was collected and dried over anhydrous Na₂SO₄. The solid was filtered off and the organic solvent was evaporated off under vacuum to give the crude compound. The crude product was purified by chromatography on silica gel using a mixture of hexane and ethyl acetate as a gradient eluent. Yield of the title compound was 109 ng (96%).

¹H-NMR (400 MHz, CDCl₃): δ 5.496-5.477 (m, 2H), 5.222-5.188 (m, 1H), 3.936-3.912 (m, 1H), 3.723-3.655 (m, 4H), 2.445-1.117 (m, 21H), 0.934-0.917 (m, 3H).

¹³C-NMR (100 MHz, CDCl₃): 174.311, 142.653, 134.956, 132.968, 120.816, 77.492, 77.083, 76.916, 76.324, 57.242, 51.519, 45.174, 41.447, 38.168, 38.002, 37.493, 35.854, 33.501, 28.719, 25.061, 22.275, 15.649, 3.528.

Example 22

(E)-5-((3aS,4R,5R,6aS)-5-hydroxy-4-((3S,4S,E)-3-hydroxy-4-methyloct-1-en-6-yn-1-yl)hexahydropentalen-2(1H)-ylidene)pentanoic acid (16(S)-iloprost)

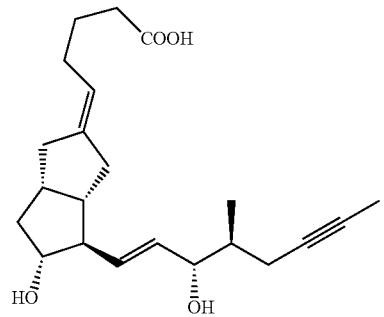 [SMILES: CC#CC[C@H](C)[C@H](O)/C=C/[C@@H]1[C@H]2C/C(=C/CCCC(=O)O)C[C@H]2C[C@H]1O]

(E)-methyl 5-((3aS,4R,5R,6aS)-5-hydroxy-4-((3S,4S,E)-3-hydroxy-4-methyloct-1-en-6-yn-1-yl)he xahydropentalen-2(1H)-ylidene)pentanoate (100 mg, 0.267 mmole, from Example 21) was dissolved in methanol (1 mL) and a solution of sodium hydroxide (23.5 mg, 0.587 mmol) in water (1 mL) was added dropwise slowly thereto at 10° C. After the completion of reaction, the methanol was removed from reaction mixture in vacuum. The residue was diluted with water (5 mL) and further washed with methyl-tert-butyl ether (5 mL). The aqueous layer was acidified with 3N aqueous HCl to pH 3-4 and further extracted with methyl-tert-butyl ether (5 mL). The organic layer was dried over anhydrous Na₂SO₄. The solid was filtered off and the organic solvent was evaporated off under vacuum. The crude product was purified by chromatography on silica gel using a mixture of acetonitrile and water as a gradient eluent. Yield of the title compound was 77 mg (80%). HPLC analysis of the product showed that 0.42% Z-isomer was found.

¹H-NMR (400 MHz, CDCl₃): δ 5.524-5.506 (m, 2H), 5.225 (m, 1H), 3.974-3.961 (m, 1H), 3.748-3.682 (m, 1H), 2.469-1.666 (m, 23H), 1.205-1.156 (m, 1H), 0.954-0.937 (m, 3H).

Example 23

(Z)-methyl 6-bromo-7-((1R,2R,3R)-3-((tert-butyldimethylsilyl)oxy)-2-((3S,E)-3-((tert-butyldimet hylsilyl)oxy)-4-methyloct-1-en-6-yn-1-yl)-5-oxocyclopentyl)hept-5-enoate (from (R)-1j to 2b)

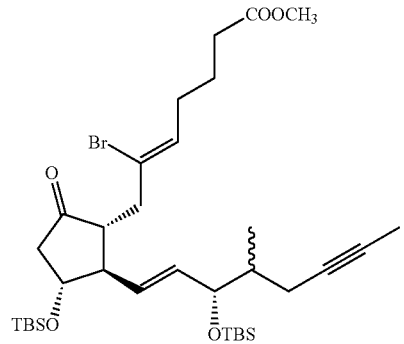 [SMILES: CC#CCC(C)[C@@H](/C=C/[C@H]1[C@H](O[Si](C)(C)C(C)(C)C)CC(=O)[C@@H]1C/C(Br)=C/CCCC(=O)OC)O[Si](C)(C)C(C)(C)C]

The compound was obtained from (R,Z)-methyl 6-bromo-7-(3-((tert-butyldimethylsilyl)oxy)-5-oxocyclopent-1-en-1-yl)hept-5-enoate (40.0 g, 92.7 mmole, from Example 17) and tert-butyldimethyl(((3S,E)-4-methyl-1-(tributylstannyl)oct-1-en-6-yn-3-yl)oxy)silane (165.7 g, 306 mmole) by following the procedure of Example 18. Yield of the title compound was 57.88 g (91%).

$^1$H-NMR (400 MHz, CDCl$_3$): δ 5.693 (t, 1H, J=6.8 Hz), 5.543-5.501 (m, 2H), 4.155-4.000 (m, 2H), 3.668 (s, 3H), 2.781-2.182 (m, 13H), 1.776-1.579 (m, 5H), 0.919-0.874 (m, 21H), 0.066-0.002 (m, 12H)

Example 24

(Z)-methyl 6-bromo-7-((1R,2R,3R)-3-((tert-butyldimethylsilyl)oxy)-2-((3S,E)-3-((tert-butyldimet hylsilyl)oxy)-4-methyloct-1-en-6-yn-1-yl)-5-methylenecyclopentyl)hept-5-enoate (from 2b to 3b)

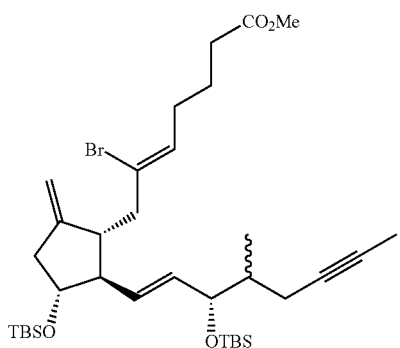 [SMILES: C=C1C[C@@H](O[Si](C)(C)C(C)(C)C)[C@H](/C=C/[C@@H](O[Si](C)(C)C(C)(C)C)C(C)CC#CC)[C@H]1C/C(Br)=C/CCCC(=O)OC]

The compound was obtained from (Z)-methyl 6-bromo-7-((1R,2R,3R)-3-((tert-butyldimethylsilyl)oxy)-2-((3S,E)-3-((tert-butyldimet hylsilyl)oxy)-4-methyloct-1-en-6-yn-1-yl)-5-oxocyclopentyl)hept-5-enoate (56.0 g, 81.9 mmole, from Example 23) by following the procedure of Example 19. Yield of the title compound was 29.77 g (53%).

$^1$H-NMR (400 MHz, CDCl$_3$): δ 5.645 (t, 1H, J=6.4 Hz), 5.458-5.418 (m, 2H), 4.910-4.831 (m, 2H), 4.114-3.889 (m, 2H), 3.669 (s, 3H), 2.677-2.063 (m, 12H), 1.777-1.634 (m, 6H), 0.921-0.870 (m, 21H), 0.038-0.007 (m, 12H).

Example 25

(E)-methyl 5-((3aS,4R,5R,6aS)-5-((tert-butyldimethylsilyl)oxy)-4-((3S,E)-3-((tert-butyldimethylsi lyl)oxy)-4-methyloct-1-en-6-yn-1-yl)hexahydropentalen-2(1H)-ylidene)pentanoate (from 3b to 4b)

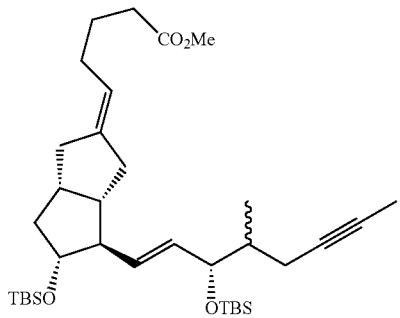 [SMILES: CC#CCC(C)[C@@H](/C=C/[C@@H]1[C@H]2C/C(=C/CCCC(=O)OC)C[C@H]2C[C@H]1O[Si](C)(C)C(C)(C)C)O[Si](C)(C)C(C)(C)C]

The compound was obtained from (Z)-methyl 6-bromo-7-((1R,2R,3R)-3-((tert-butyldimethylsilyl)oxy)-2-((3S,E)-3-((tert-butyldimet hylsilyl)oxy)-4-methyloct-1-en-6-yn-1-yl)-5-methylenecyclopentyl)hept-5-enoate (29.0 g, 42.5 mmole, from Example 24) by following the procedure of Example 20. Yield of the title compound was 14.63 g (57%).

$^1$H-NMR (400 MHz, CDCl$_3$): δ 5.527-5.353 (m, 2H), 5.185 (m, 1H), 4.101-3.937 (m, 1H), 3.762-3.700 (m, 1H), 3.659 (s, 3H), 2.355-1.908 (m, 14H), 1.787 (s, 3H), 1.707-1.653 (m, 3H), 1.224-1.151 (m, 1H), 0.926-0.856 (m, 21H), 0.061--0.007 (m, 12H).

Example 26

(E)-methyl 5-((3aS,4R,5R,6aS)-5-hydroxy-4-((3S,E)-3-hydroxy-4-methyloct-1-en-6-yn-1-yl)hexa hydropentalen-2(1H)-ylidene)pentanoate (from 4b to iloprost methyl ester)

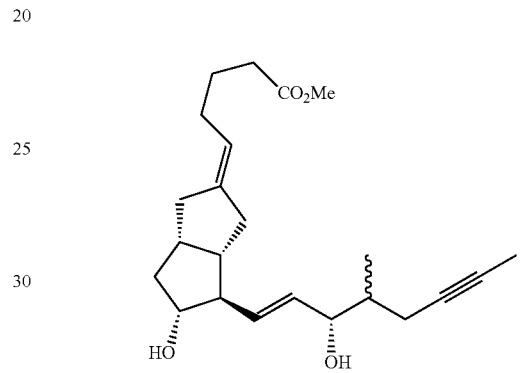

The compound was obtained from (E)-methyl 5-((3aS,4R,5R,6aS)-5-((tert-butyldimethylsilyl)oxy)-4-((3S,E)-3-((tert-butyldimethylsi lyl)oxy)-4-methyloct-1-en-6-yn-1-yl)hexahydropentalen-2(1H)-ylidene)pentanoate (12.0 g, 19.9 mmole, from Example 25) by following the procedure of Example 21. Yield of the title compound was 6.3 g (84%).

$^1$H-NMR (400 MHz, CDCl$_3$): δ 5.539-5.510 (m, 2H), 5.215 (m, 1H), 4.076-3.960 (m, 1H), 3.751-3.685 (m, 1H), 3.661 (s, 3H), 2.450-1.638 (m, 20H), 1.204-1.129 (m, 1H), 0.996-0.930 (m, 3H).

Example 27

(E)-5-((3aS,4R,5R,6aS)-5-hydroxy-4-((3S,E)-3-hydroxy-4-methyloct-1-en-6-yn-1-yl)h exahydropentalen-2(1H)-ylidene)pentanoic acid (iloprst)

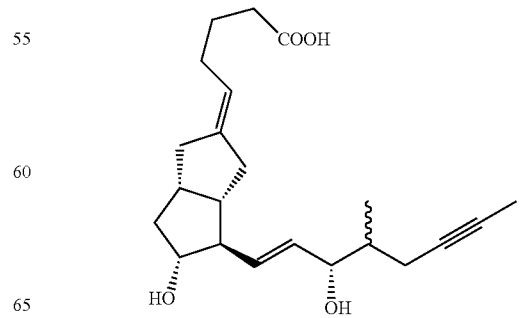

The compound was obtained from (E)-methyl 5-((3aS,4R,5R,6aS)-5-hydroxy-4-((3S,E)-3-hydroxy-4-methyloct-1-en-6-yn-1-yl)hexa hydropentalen-2(1H)-ylidene)pentanoate (3.0 g, 8 mmole, from Example 26) by following the procedure of Example 22. Yield of the title compound was 2.31 g (80%). HPLC analysis of the product showed that 0.41% Z-isomers was found and no 15-epimers was detected.

$^1$H-NMR (400 MHz, CDCl$_3$): δ 5.528-5.499 (m, 2H), 5.220-5.203 (m, 1H), 4.069-3.939 (m, 1H), 3.739-3.674 (m, 1H), 2.457-1.661 (m, 23H), 1.201-1.126 (m, 1H), 1.017-0.935 (m, 3H).

Example 28

(2R,3R,4R)-2-((Z)-2-bromo-7-((tert-butyldimethylsilyl)oxy)hept-2-en-1-yl)-4-((tert-b utyldimethylsi-lyl)oxy)-3-((3S,E)-3-((tert-butyldimethylsilyl)oxy)-4-methyloct-1-en-6-yn-1-yl)cyclo pentanone (from (R)-1f to 2b')

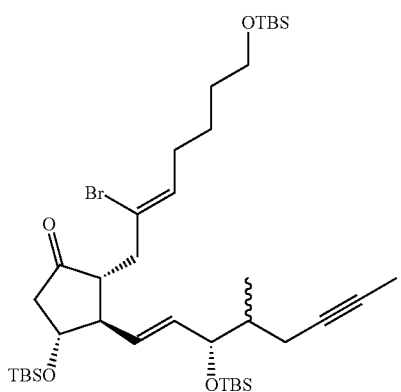 [SMILES: CC#CCC(C)[C@@H](/C=C/[C@H]1[C@H](O[Si](C)(C)C(C)(C)C)CC(=O)[C@@H]1C/C(Br)=C/CCCCO[Si](C)(C)C(C)(C)C)O[Si](C)(C)C(C)(C)C]

The compound was obtained from (R,Z)-2-(2-bromo-7-((tert-butyldimethylsilyl)oxy)hept-2-en-1-yl)-4-((tert-butyldimeth ylsilyl)oxy)cyclopent-2-enone (10.0 g, 19.3 mmole, from Example 13) and tert-butyldimethyl(((3S,E)-4-methyl-1-(tributylstannyl)oct-1-en-6-yn-3-yl)oxy)silane (31.4 g, 58 mmole) by following the procedure of Example 18. Yield of the title compound was 10.41 g (70%).

$^1$H-NMR (400 MHz, CDCl$_3$): δ 5.699 (m, 1H), 5.566-5.462 (m, 2H), 4.158-3.990 (m, 2H), 3.609 (m, 2H), 2.807-1.901 (m, 10H), 1.772 (s, 3H), 1.707-1.418 (m, 5H), 1.040-0.727 (m, 30H), 0.118-0.000 (m, 18H).

Example 29

(((Z)-6-bromo-7-((1R,2R,3R)-3-((tert-butyldimethylsilyl)oxy)-2-((3S,E)-3-((tert-butyl dimethylsi-lyl)oxy)-4-methyloct-1-en-6-yn-1-yl)-5-methylenecyclopentyl)hept-5-en-1-yl)oxy)(te rt-butyl)dimethylsilane (from 2b' to 3b')

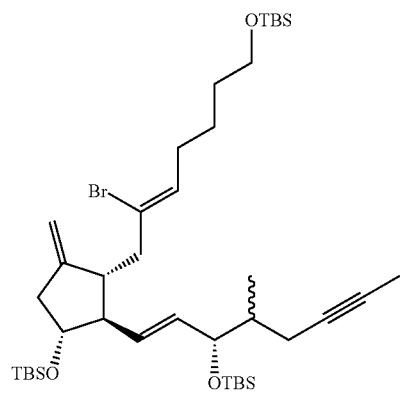 [SMILES: C=C1C[C@@H](O[Si](C)(C)C(C)(C)C)[C@H](/C=C/[C@@H](O[Si](C)(C)C(C)(C)C)C(C)CC#CC)[C@H]1C/C(Br)=C/CCCCO[Si](C)(C)C(C)(C)C]

The compound was obtained from (2R,3R,4R)-2-((Z)-2-bromo-7-((tert-butyldimethylsilyl)oxy)hept-2-en-1-yl)-4-((tert-b utyldimethylsi-lyl)oxy)-3-((3S,E)-3-((tert-butyldimethylsilyl)oxy)-4-methyloct-1-en-6-yn-1-yl)cyclo pentanone (11.0 g, 14.3 mmole, from Example 28) by following the procedure of Example 19. Yield of the title compound was 8.47 g (77%).

$^1$H-NMR (400 MHz, CDCl$_3$): δ 5.660 (t, 1H, J=6.8), 5.463-5.418 (m, 2H), 4.907-4.845 (m, 2H), 4.106-3.894 (m, 2H), 3.627-3.596 (t, 2H, J=5.6 Hz), 2.642-1.263 (m, 15H), 1.778 (s, 3H), 0.927-0.873 (m, 30H), 0.043--0.003 (m, 18H).

Example 30 tert-butyl(((E)-5-((3aS,4R,5R,6aS)-5-((tert-butyldimethylsilyl)oxy)-4-((3S,E)-3-((tert-butyldimethylsilyl)oxy)-4-methyloct-1-en-6-yn-1-yl)hexahydropentalen-2(1H)-ylidene)pentyl)oxy)di methylsilane (from 3b' to 4b')

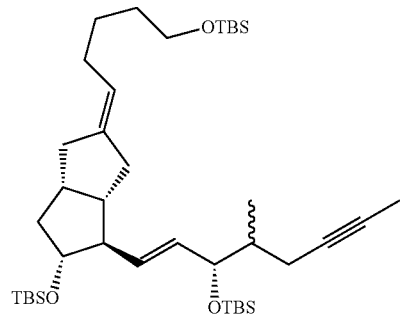 [SMILES: CC#CCC(C)[C@@H](/C=C/[C@@H]1[C@H]2C/C(=C/CCCCO[Si](C)(C)C(C)(C)C)C[C@H]2C[C@H]1O[Si](C)(C)C(C)(C)C)O[Si](C)(C)C(C)(C)C]

The compound was obtained from (((Z)-6-bromo-7-((1R,2R,3R)-3-((tert-butyldimethylsilyl)oxy)-2-((3S,E)-3-((tert-butyl dimethylsi-lyl)oxy)-4-methyloct-1-en-6-yn-1-yl)-5-methylenecyclopentyl)hept-5-en-1-yl)oxy)(te rt-butyl)dimethylsilane (4.0 g, 5.2 mmole, from Example 29) by following the procedure of Example 20. Yield of the title compound was 2.01 g (56%).

$^1$H-NMR (400 MHz, CDCl$_3$): δ5.486-5.397 (m, 2H), 5.217 (m, 1H), 4.094-3.962 (m, 1H), 3.746-3.728 (m, 1H), 3.620-3.587 (m, 2H), 2.331-1.205 (m, 18H), 1.780 (s, 3H), 0.933-0.863 (m, 30H), 0.067--0.001 (m, 18H).

$^{13}$C-NMR (100 MHz, CDCl$_3$): 141.910, 132.824, 132.331, 132.073, 131.549, 121.636, 78.470, 78.379, 76.238, 75.297, 63.168, 56.086, 56.033, 44.594, 44.495, 42.590, 40.146, 39.835, 38.233, 38.173, 37.725, 36.017, 35.987, 32.495, 29.193, 26.104, 25.983, 25.914, 22.430, 22.074, 18.362, 18.187, 18.164, 18.096, 15.424, 14.430, 3.485, 3.454, −4.447, −4.599, 4.978, −5.252.

Example 31

((2S,3R,4R)-2-((Z)-2-bromo-7-((tert-butyldimethyl-silyl)oxy)hept-2-en-1-yl)-4-((tert-b utyldimethylsi-lyl)oxy)-3-((3S,E)-3-((tert-butyldimethylsilyl)oxy)-4-methyloct-1-en-6-yn-1-yl)cyclo pentyl)methanol (from 3b' to 3')

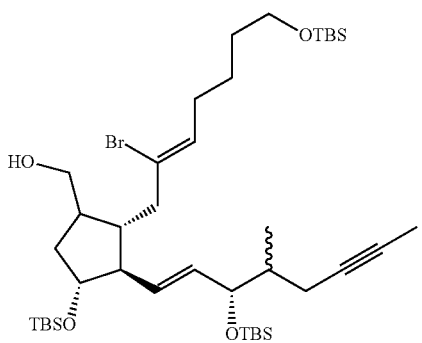 [SMILES: CC#CCC(C)[C@@H](/C=C/[C@H]1[C@H](O[Si](C)(C)C(C)(C)C)CC(CO)[C@@H]1C/C(Br)=C/CCCCO[Si](C)(C)C(C)(C)C)O[Si](C)(C)C(C)(C)C]

To a solution of 9-BBN in THF (0.5M, 242 mL, 121 mmole) was added to a solution of ((Z)-6-bromo-7-((1R,2R,3R)-3-((tert-butyldimethylsilyl)oxy)-2-((3S,E)-3-((tert-butyld imethylsi-lyl)oxy)-4-methyloct-1-en-6-yn-1-yl)-5-methylenecyclopentyl)hept-5-en-1-yl)oxy)te rt-butyl) dimethylsilane(31 g, 40.3 mmole, from Example 29) in THF (310 mL) at 0° C. and the reaction mixture was stirred for 30 minutes at the same temperature. And the reaction mixture was cooled and keep stir at −10° C., then 31% hydrogen peroxide (40.85 mL) were added thereto at −10° C. After 10 minutes, the aqueous sodium hydroxide (3M, 121 mL, 363 mmole) were added thereto at the same temperature. Then the reaction mixture was warmed to 0° C. and keep stir for 30 min. The completion of reaction was confirmed by TLC monitor. The reaction mixture was quenched with 10% aqueous NaCl(1 L) and the reaction mixture was phase separated. The organic layer was collected and dried over anhydrous $Na_2SO_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 17.76 g (56%).

$^1$H-NMR (400 MHz, $CDCl_3$): δ 5.743 (m, 1H), 5.458-5.341 (m, 2H), 4.119-3.999 (m, 2H), 3.769-3.449 (m, 4H), 2.740-2.007 (m, 7H), 1.770 (s, 3H), 1.675-1.420 (m, 9H), 0.945-0.720 (m, 30H), 0.078-−0.013 (m, 18H).

Example 32

((1S,2S,3R,4R)-2-((Z)-2-bromo-7-((tert-butyldim-ethylsilyl)oxy)hept-2-en-1-yl)-4-((ter t-butyldimeth-ylsilyl)oxy)-3-((3S,E)-3-((tert-butyldimethylsilyl)oxy)-4-methyloct-1-en-6-yn-1-yl)cyclopentyl)methyl 4-methylbenzenesulfonate (from 3' to 3")

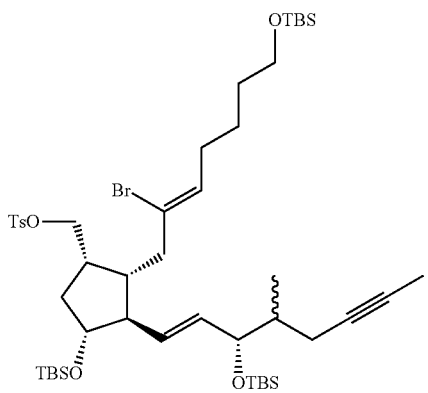 [SMILES: CC#CCC(C)[C@@H](/C=C/[C@@H]1[C@@H](C/C(Br)=C/CCCCO[Si](C)(C)C(C)(C)C)[C@@H](COS(=O)(=O)c2ccc(C)cc2)C[C@H]1O[Si](C)(C)C(C)(C)C)O[Si](C)(C)C(C)(C)C]

((2S,3R,4R)-2-((Z)-2-bromo-7-((tert-butyldimethylsilyl)oxy)hept-2-en-1-yl)-4-((tert-butyldimethylsilyl)oxy)-3-((3S,E)-3-((tert-butyldimethylsilyl)oxy)-4-methyl oct-1-en-6-yn-1-yl)cyclopentyl)methanol (37.34 g, 47.5 mmole, from Example 31) was dissolved with dichloromethane (380 mL). Then triethylamine (14.4 g, 142 mmole) DMAP (0.58g, 47.5 mmole) and 4-toluenesulfonyl chloride (22.64 g, 118.7 mmole) were added thereto. The reaction mixture was heat to reflux. The completion of reaction was confirmed by TLC monitor. The reaction mixture was cool to room temperature and quenched with 10% aqueous $NaHCO_3$ (450 mL) and the reaction mixture was phase separated. The organic layer was collected and dried over anhydrous $Na_2SO_4$. The solid was filtered off and the organic solvent was evaporated off under vacuum to give the 45.51 g of crude compound.

Example 33 tert-butyl(((E)-5-((3aS,4R,5R,6aS)-5-((tert-butyldi-methylsilyl)oxy)-4-((3S,E)-3-((tert-butyldimethylsi-lyl)oxy)-4-methyloct-1-en-6-yn-1-yl)hexahydropen-talen-2(1R)-ylidene)pentyl)oxy)di methylsilane (from 3" to 4')

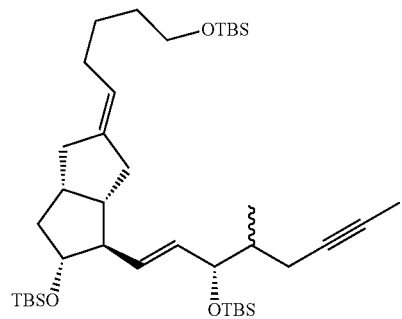 [SMILES: CC#CCC(C)[C@@H](/C=C/[C@@H]1[C@H]2C/C(=C/CCCCO[Si](C)(C)C(C)(C)C)C[C@H]2C[C@H]1O[Si](C)(C)C(C)(C)C)O[Si](C)(C)C(C)(C)C]

((1S,2S,3R,4R)-2-((Z)-2-bromo-7-((tert-butyldimethylsi-lyl)oxy)hept-2-en-1-yl)-4-((tert-butyldimethylsilyl)oxy)-3-

((3S,E)-3-((tert-butyldimethylsilyl)oxy)-4-methyloct-1-en-6-yn-1-yl)cyclopentyl)methyl 4-methylbenzenesulfonate (45.0 g, 47.8 mmole, from Example 32) in dry THF (450 mL) was added dropwise 1.9M (60 mL, 114 mmol) tert-butyllithium in pentane at −70° C. and was stirred for 1 hour at the same temperature. The completion of reaction was confirmed by TLC monitor. The reaction mixture was quenched with saturated aqueous ammonium chloride (450 mL). The reaction mixture was phase separated and the aqueous layer was extracted with ethyl acetate. The organic layers were combined and dried over anhydrous $Na_2SO_4$. The solid was filtered off and the organic solvent was evaporated under vacuum to give the crude title compound. The crude product was purified by chromatography on sili-ca gel using a mixture of hexane and ethyl acetate as a gradient eluent. Yield of the title compound was 24.0 g (73%).

Example 34

(E)-5-((3aS,4R,5R,6aS)-5-((tert-butyldimethylsilyl)oxy)-4-((3S,E)-3-((tert-butyldimet hylsilyl)oxy)-4-methyloct-1-en-6-yn-1-yl)hexahydropentalen-2(1H)-ylidene)pentan-1-ol

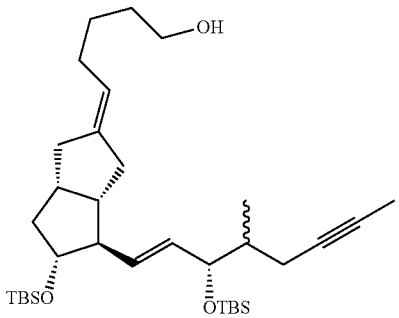 [SMILES: CC#CCC(C)[C@@H](/C=C/[C@@H]1[C@H]2C/C(=C/CCCCO)C[C@H]2C[C@H]1O[Si](C)(C)C(C)(C)C)O[Si](C)(C)C(C)(C)C]

tert-butyl(((E)-5-((3aS,4R,5R,6aS)-5-((tert-butyldimethylsilyl)oxy)-4-((3S, E)-3-((tert-butyldimethylsilyl)oxy)-4-methyloct-1-en-6-yn-1-yl)hexahydropentalen-2(1H)-ylidene)pentyl)oxy)dimethylsilane (2.43 g, 3.5 mmole, from Example 33) was dissolved with n-hexane (370 mL). Then aluminum oxide (250 g, containing $H_2O$) was added thereto. The suspension of reaction mixture was stirred at room temperature. The completion of reaction was confirmed by TLC monitor. The aluminum ox-ide was filtered off and the organic solvent was evaporated off under vacuum to give the crude compound. The crude product was purified by chromatography on silica gel using a mixture of hexane and ethyl acetate as a gradient eluent. Yield of the title compound was 1.6 g (80%).

$^1$H-NMR (400 MHz, $CDCl_3$): δ 5.490-5.391 (m, 2H), 5.209 (m, 1H), 4.089-3.958 (m, 1H), 3.742-3.725 (m, 1H), 3.636-3.606 (m, 2H), 2.209-1.156 (m, 16H), 1.769 (s, 3H), 0.923-0.855 (m, 21H), 0.032-−0.007 (m, 12H).

Example 35

(E)-5-((3aS,4R,5R,6aS)-5-((tert-butyldimethylsilyl)oxy)-4-((3S,E)-3-((tert-butyldimet hylsilyl)oxy)-4-methyloct-1-en-6-yn-1-yl)hexahydropentalen-2(1H)-ylidene) pentanoic acid

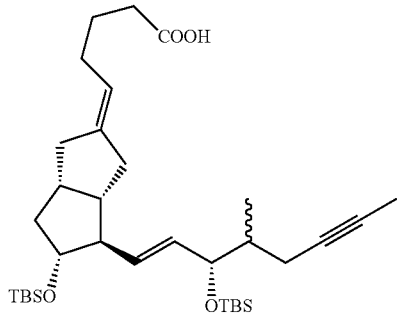 [SMILES: CC#CCC(C)[C@@H](/C=C/[C@@H]1[C@H]2C/C(=C/CCCC(=O)O)C[C@H]2C[C@H]1O[Si](C)(C)C(C)(C)C)O[Si](C)(C)C(C)(C)C]

(E)-5-((3aS,4R,5R,6aS)-5-((tert-butyldimethylsilyl)oxy)-4-((3S,E)-3-((tert-butyldimethylsi-lyl)oxy)-4-methyloct-1-en-6-yn-1-yl)hexahydropentalen-2(1H)-ylidene)pentan-1-ol (1.1 g, 1.9 mmole, from Example 34) was dissolved with dichloromethane (11 mL) and water (11 mL). Then 2,2,6,6-tetramethylpiperidine-1-oxyl (60 mg, 0.38 mmole) and (diacetoxyiodo)benzene (1.54 g, 0.4.8 mmole) were added thereto. The reaction mixture was stirred at room temperature. The completion of reaction was confirmed by TLC monitor. The reaction mixture was quenched with 20% aqueous sodium thiosulfate (22 mL). The reaction mixture was phase separated and the aqueous layer was extracted with ethyl acetate. The organic layers were combined and dried over anhydrous $Na_2SO_4$. The solid was filtered off and the organic solvent was evaporated under vacuum to give the crude title compound. The crude product was purified by chromatography on silica gel using a mixture of hexane and ethyl acetate as a gradient eluent. Yield of the title compound was 0.8 g (72%).

$^1$H-NMR (400 MHz, $CDCl_3$): δ 5.497-5.379 (m, 2H), 5.211-5.195 (m, 1H), 4.144-3.980 (m, 1H), 3.752-3.734 (m, 1H), 2.181-1.612 (m, 17H), 1.777 (s, 3H), 1.269 (m, 1H), 0.931-0.861 (m, 21H), 0.063-−0.001 (m, 12H).

Example 36

(E)-5-((3aS,4R,5R,6aS)-5-hydroxy-4-((3S,E)-3-hydroxy-4-methyloct-1-en-6-yn-1-yl) hexahydropentalen-2(1H)-ylidene)pentanoic acid (iloprost)

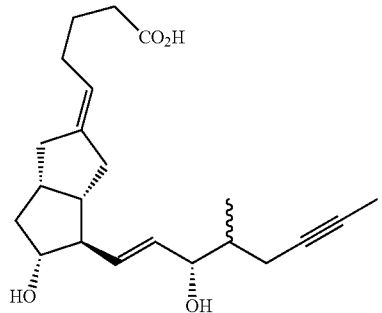 [SMILES: CC#CCC(C)[C@H](O)/C=C/[C@@H]1[C@H]2C/C(=C/CCCC(=O)O)C[C@H]2C[C@H]1O]

(E)-5-(((3aS,4R,5R,6aS)-5-((tert-butyldimethylsilyl)oxy)-4-((3S,E)-3-((tert-butyldimethylsi-lyl)oxy)-4-methyloct-1-en-6-yn-1-yl)hexahydropentalen-2(1H)-ylidene)pentanoic acid (800 mg, 1.35 mmole, from Example 35) was diluted with THF (8 mL), and 1M TBAF solution (5.4 mL, 5.4 mmole) was added thereto. The reaction was stirred at room temperature and the progress of reaction was check by TLC. After the completion of reaction, the mixture was quenched with saturated aqueous ammonium chloride (20 mL), and ethyl acetate (20 mL) was added for extraction. Then the reaction mixture was phase separated. The organic layer was collected and dried over anhydrous $Na_2SO_4$. The solid was filtered off and the organic solvent was evaporated off under vacuum to give the crude compound. The crude product was purified by chromatography on silica gel using a mixture of hexane and ethyl acetate as a gradient eluent. Yield of the title compound was 420 mg (86%).

What is claimed is:

1. A process for preparing compound of Formula 4:

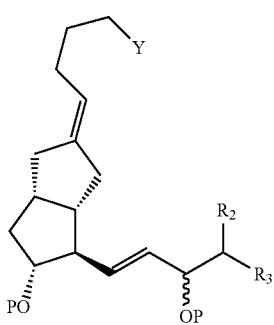

4 wherein Y is —$CH_2OP$ or —$COOR_1$; P is H or a hydroxyl protective group; $R_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy; $R_2$ is H or $C_{1-4}$-alkyl; and $R_3$ is $C_{1-7}$-alkyl, $C_{2-7}$-alkynyl, aryl or aryloxy, each of which is unsubstituted or substituted by $C_{1-4}$-alkyl, halogen, or trihalomethyl, the process comprising the steps of:

(1) reacting a starting compound of Formula 1:

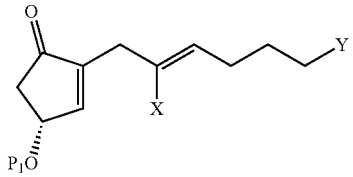

1 wherein X is F, Cl, Br, I, or —OTs; $P_1$ is a hydroxyl protective group; and Y is as defined above, with a starting cuprate derived from a compound of Formula $L_1$, Formula $L_2$, or Formula $L_3$:

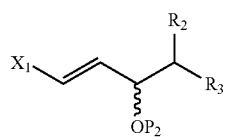

$L_1$

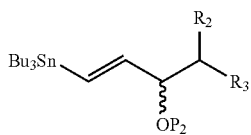

$L_2$

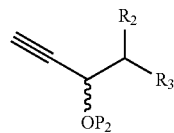

$L_3$ wherein $X_1$ is Cl, Br, or I; $P_2$ is a hydroxyl protective group; and $R_2$ and $R_3$ are as defined above, to form a compound of Formula 2:

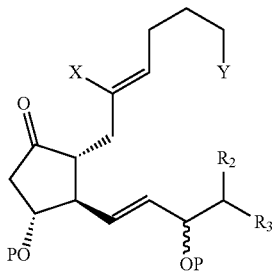

2 wherein P, X, Y, $R_2$ and $R_3$ are as defined above;

(2) methylenation of a ketone radical of the compound of Formula 2 to form a compound of the following formula 3:

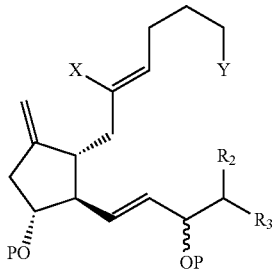

3 wherein P, X, Y, $R_2$ and $R_3$ are as defined above;

(3) performing an intramolecular cyclization reaction to the compound of Formula 3 to form the compound of Formula 4:

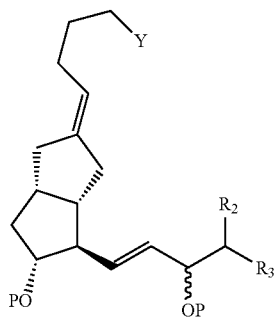

4 wherein P, Y, $R_2$ and $R_3$ are as defined above; and
(4) optionally performing a deprotecting reaction for removing $P_1$ and/or $P_2$.

2. The process according to claim 1, wherein the intramolecular cyclization reaction is an intramolecular Suzuki reaction with a boron reagent using a palladium catalyst and a base to form the compound of Formula 4.

3. The process according to claim 1, wherein the intramolecular cyclization reaction comprises the steps of:
(a) hydrobornation of the compound of Formula 3 with a boron reagent, followed by oxidation with basic hydrogen peroxide to form an alcohol compound of Formula 3':

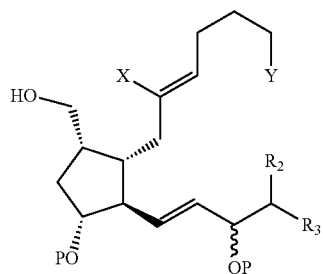

3' wherein P, X, Y, $R_2$ and $R_3$ are as defined in claim 1;
(b) sulfonylation of the compound of Formula 3' in the presence of a base with a sulfonyl donor to form a compound of Formula 3":

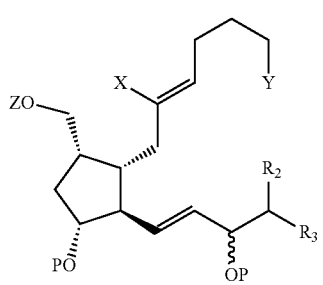

3"

wherein Z is a sulfonyl group; and P X, Y, $R_2$ and $R_3$ are as defined above; and
(c) intramolecular alkylation of the compound of Formula 3" in the presence of a base to form the compound of Formula 4.

4. The process according to claim 1 for preparing a compound of Formula 4a,

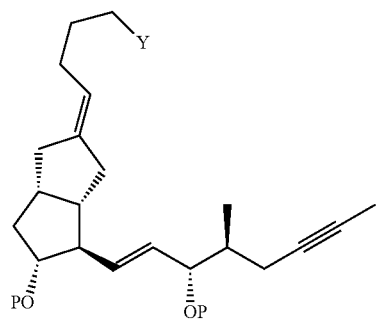

4a wherein Y is —$CH_2OP$ or —$COOR_1$; P is H or a hydroxyl protective group; and $R_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy, the process comprising the steps of:

(1') reacting an optically enriched compound of Formula (R)-1:

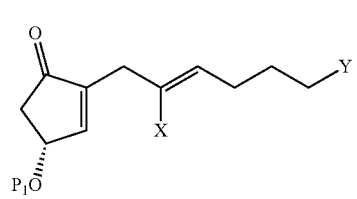

(R)-1 wherein X is F, Cl, Br, I, or —OTs; $P_1$ is a hydroxyl protective group; and Y is as defined above, with a cuprate derived from a compound of Formula $L_{1a}$, Formula $L_{2a}$, or Formula $L_{3a}$:

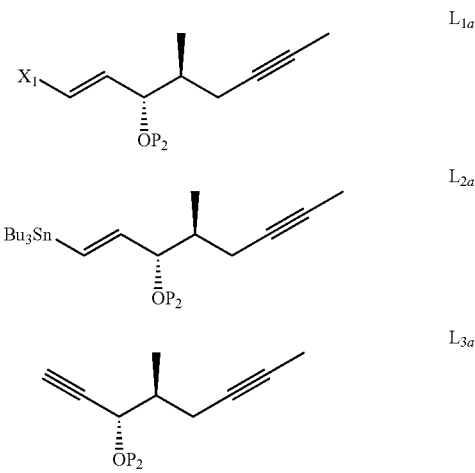

wherein $X_1$ is Cl, Br, or I; and $P_2$ is a hydroxyl protective group, to form a compound of Formula 2a:

2a

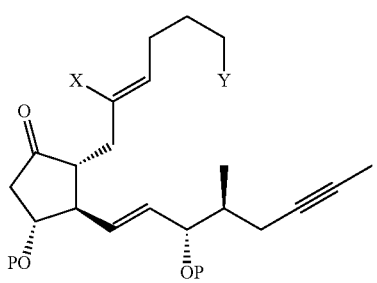

wherein P, X, and Y are as defined above;
(2')methylenation of a ketone radical of the compound of Formula 2a to form a compound of Formula 3a:

3a

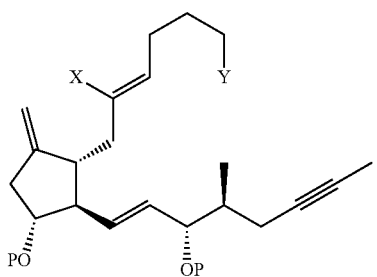

wherein P, X and Y are as defined above;
(3') performing an intramolecular cyclization reaction to the compound of Formula 3a to form the compound of Formula 4a:

4a

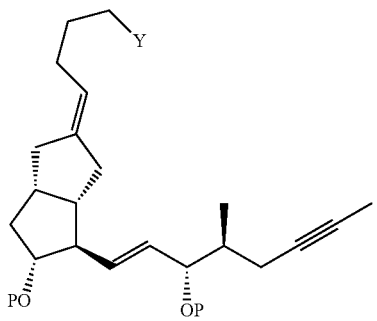

wherein P and Y are as defined above; and
(4')optionally performing a deprotecting reaction for removing $P_1$ and/or $P_2$.

5. The process according to claim 4, wherein the intramolecular cyclization reaction is an intramolecular Suzuki reaction with a boron reagent using a palladium catalyst and a base to form the compound of Formula 4a.

6. The process according to claim 4, wherein the intramolecular cyclization reaction comprises the steps of:
   (a) hydrobornation of the compound of Formula 3a with a boron reagent, followed by oxidation with basic hydrogen peroxide to form an alcohol compound of Formula 4a-1:

4a-1

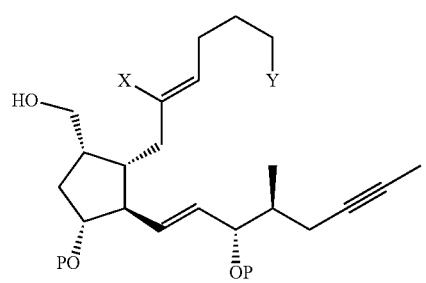

wherein P, X and Y are as defined in claim 4;
(b) sulfonylation of the compound of Formula 4a-1 in the presence of a base with a sulfonyl donor to form a compound of Formula 4a-2:

4a-2

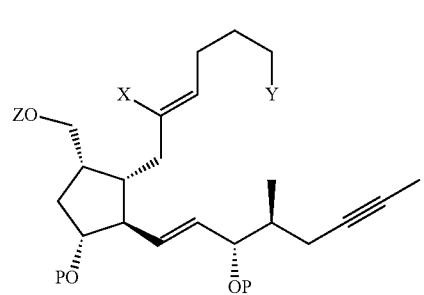

wherein Z is a sulfonyl group; and P, X and Y are as defined above; and
(c) intramolecular alkylation of the compound of Formula 4a-2 in the presence of a base to form the compound of Formula 4a.

7. The process according to claim 1 for preparing compound of Formula 4b:

4b

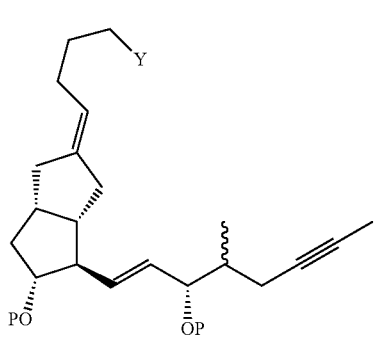

wherein Y is —$CH_2OP$ or —$COOR_1$; P is H or a hydroxyl protective group; and $R_1$ is $C_{1-7}$-alkyl, aryl or aralkyl, each of which is unsubstituted or substituted by $C_{1-4}$-alkyl, $C_{2-7}$-alkenyl, $C_{2-7}$-alkynyl, nitro, halogen or alkoxy, the process comprising the steps of:
(1") reacting an optically enriched compound of Formula (R)-1:

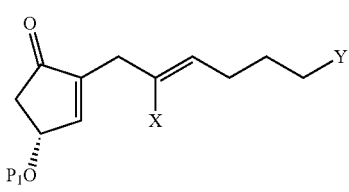

(R)-1 wherein X is F, Cl, Br, I, or —OTs; $P_1$ is a hydroxyl protective group; and Y is as defined above, with a cuprate derived from a compound of Formula $L_{1b}$, Formula $L_{2b}$, or Formula $L_{3b}$,

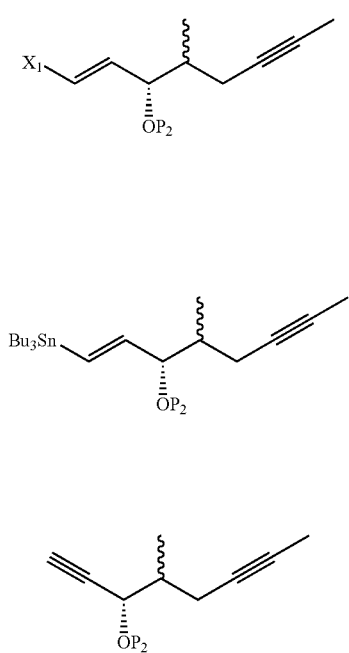

$L_{1b}$ $L_{2b}$ $L_{3b}$ wherein $X_1$ is Cl, Br, or I; and $P_2$ is a hydroxyl protective group, to form a compound of Formula 2b:

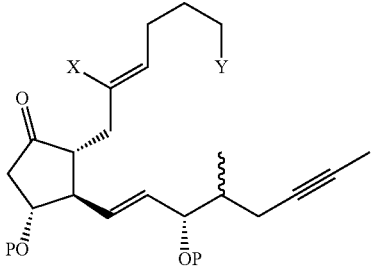

2b wherein P, X and Y are as defined above;

(2''') methylenation of a ketone radical of the compound of Formula 2b to form a compound of Formula 3b:

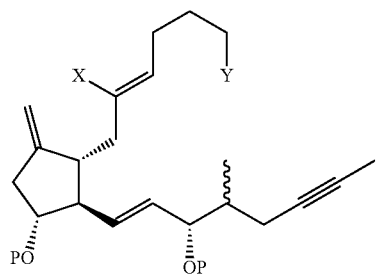

3b wherein P, X and Y are as defined above;

(3''') performing an intramolecular cyclization reaction to the compound of Formula 3b to form a compound of Formula 4b:

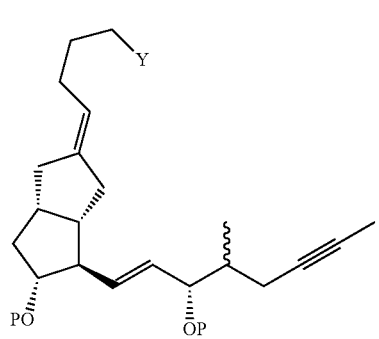

4b wherein P and Y are as defined above; and (4''') optionally performing a deprotecting reaction for removing $P_1$ and/or $P_2$.

8. The process according to claim 7, wherein the intramolecular cyclization reaction is an intramolecular Suzuki reaction with a boron reagent using a palladium catalyst and a base to form the compound of Formula 4b.

9. A process according to claim 7, wherein the intramolecular cyclization reaction comprises the steps of:

(a) hydroboration of the compound of Formula 3b with a boron reagent, followed by oxidation with basic hydrogen peroxide to form a compound of Formula 4b-1:

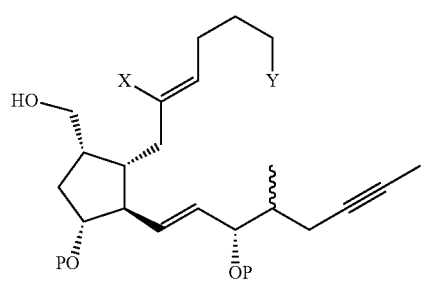

4b-1 wherein P, X and Y are as defined in claim 7;

(b) sulfonylation of the compound of Formula 4b-1 in the presence of a base with a sulfonyl donor to form a compound of Formula 4b-2:

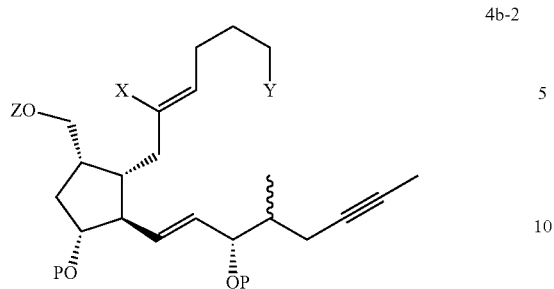
4b-2
wherein Z is a sulfonyl group; and P, X and Y are as defined above; and
(c) intramolecular alkylation of the compound of Formula 4b-2 in the presence of a base to form the compound of Formula 4b.
* * * * *